(12) United States Patent
Nakai et al.

(10) Patent No.: US 11,459,558 B2
(45) Date of Patent: Oct. 4, 2022

(54) METHODS FOR USING TRANSCRIPTION-DEPENDENT DIRECTED EVOLUTION OF AAV CAPSIDS

(71) Applicant: Oregon Health & Science University, Portland, OR (US)

(72) Inventors: Hiroyuki Nakai, Portland, OR (US); Samuel Huang, Portland, OR (US); Kei Adachi, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 17/337,341

(22) Filed: Jun. 2, 2021

(65) Prior Publication Data

US 2021/0348160 A1   Nov. 11, 2021

Related U.S. Application Data

(63) Continuation of application No. PCT/US2020/016273, filed on Jan. 31, 2020.

(60) Provisional application No. 62/799,603, filed on Jan. 31, 2019.

(51) Int. Cl.
| | | |
|---|---|---|
| *C12N 15/11* | (2006.01) | |
| *C12N 7/00* | (2006.01) | |
| *C12N 15/86* | (2006.01) | |

(52) U.S. Cl.
CPC ............ *C12N 15/11* (2013.01); *C12N 7/00* (2013.01); *C12N 15/86* (2013.01); *C12N 2310/11* (2013.01); *C12N 2320/33* (2013.01); *C12N 2750/14123* (2013.01); *C12N 2830/008* (2013.01)

(58) Field of Classification Search
CPC .... C07K 14/005; C07K 14/008; C12N 15/11; C12N 15/86; C12N 2310/11; C12N 2320/33; C12N 2750/14143
USPC ........... 435/6.1, 6.11, 91.1, 91.31, 455, 458; 536/23.1, 24.5
See application file for complete search history.

(56) References Cited

U.S. PATENT DOCUMENTS

| | | | |
|---|---|---|---|
| 5,866,552 A | 2/1999 | Wilson et al. | |
| 5,871,982 A | 2/1999 | Wilson et al. | |
| 6,174,527 B1 | 1/2001 | Wilson et al. | |
| 6,251,677 B1 | 6/2001 | Wilson et al. | |
| 6,258,595 B1 | 7/2001 | Gao et al. | |
| 6,274,354 B1 | 8/2001 | Wilson et al. | |
| 6,387,368 B1 | 5/2002 | Wilson et al. | |
| 6,475,769 B1 | 11/2002 | Wilson et al. | |
| 6,482,634 B1 | 11/2002 | Wilson et al. | |
| 6,485,966 B2 | 11/2002 | Gao et al. | |
| 6,759,237 B1 | 7/2004 | Wilson et al. | |
| 6,943,019 B2 | 9/2005 | Wilson et al. | |
| 6,953,690 B1 | 10/2005 | Gao et al. | |
| 7,022,519 B2 | 4/2006 | Gao et al. | |
| 7,105,345 B2 | 9/2006 | Wilson et al. | |
| 7,186,552 B2 | 3/2007 | Wilson et al. | |
| 7,198,951 B2 | 4/2007 | Gao et al. | |
| 7,235,393 B2 | 6/2007 | Gao et al. | |
| 7,238,526 B2 | 7/2007 | Wilson et al. | |
| 7,282,199 B2 | 10/2007 | Gao et al. | |
| 7,319,002 B2 | 1/2008 | Wilson et al. | |
| 7,344,872 B2 | 3/2008 | Gao et al. | |
| 7,491,508 B2 | 2/2009 | Roy et al. | |
| 7,588,772 B2 | 9/2009 | Kay et al. | |
| 7,790,449 B2 | 9/2010 | Gao et al. | |
| 7,906,111 B2 | 3/2011 | Wilson et al. | |
| 8,067,014 B2 | 11/2011 | Kay et al. | |
| 8,129,510 B2 | 3/2012 | Kay et al. | |
| 8,231,880 B2 | 7/2012 | Roy et al. | |
| 8,318,480 B2 | 11/2012 | Gao et al. | |
| 8,394,386 B2 | 3/2013 | Wilson | |
| 8,445,454 B2 | 5/2013 | Wu et al. | |
| 8,470,310 B2 | 6/2013 | Roy et al. | |
| 8,524,219 B2 | 9/2013 | Roy et al. | |
| 8,524,446 B2 | 9/2013 | Gao et al. | |
| 8,574,583 B2 | 11/2013 | Kay et al. | |
| 8,603,459 B2 | 12/2013 | Wilson et al. | |
| 8,637,255 B2 | 1/2014 | Wilson et al. | |
| 8,685,387 B2 | 4/2014 | Roy et al. | |
| 8,834,863 B2 | 9/2014 | Roy et al. | |
| 8,846,031 B2 | 9/2014 | Roy et al. | |
| 8,906,387 B2 | 12/2014 | Kay et al. | |
| 8,906,675 B2 | 12/2014 | Gao et al. | |
| 8,940,290 B2 | 1/2015 | Roy et al. | |
| 8,962,330 B2 | 2/2015 | Gao et al. | |
| 8,962,332 B2 | 2/2015 | Gao et al. | |
| 8,999,678 B2 | 4/2015 | Vandenberghe et al. | |
| 9,150,882 B2 | 10/2015 | Kay et al. | |
| 9,163,260 B2 | 10/2015 | Wilson et al. | |
| 9,169,299 B2 | 10/2015 | Lisowski et al. | |

(Continued)

FOREIGN PATENT DOCUMENTS

| | | | |
|---|---|---|---|
| WO | WO-2017197355 A2 | 11/2017 | |
| WO | WO-2018119330 A2 | 6/2018 | |

(Continued)

OTHER PUBLICATIONS

ScienceDirect Topics.*
Adachi et al (Nature Communications, Jan. 7, 2014, pp. 1-14).*
Adachi et al.: A New Recombinant Adeno-Associated Virus (AAV)-Based Random Peptide Display Library System: Infection-Defective AAV1.9-3 as a Novel Detargeted Platform for Vector Evolution. Gene Therapy and Regulation. 5(1):31-55 (2010) doi: 10.1142/S1568558610000197.

(Continued)

*Primary Examiner* — Jane J Zara
(74) *Attorney, Agent, or Firm* — Wilson Sonsini Goodrich & Rosati

(57) ABSTRACT

Disclosed are methods for performing transcription-dependent directed evolution (TRADE) and novel AAV capsids selected using such methods.

20 Claims, 43 Drawing Sheets

Specification includes a Sequence Listing.

(56) References Cited

U.S. PATENT DOCUMENTS

| | | |
|---|---|---|
| 9,198,984 B2 | 12/2015 | Lock et al. |
| 9,315,825 B2 | 4/2016 | Wilson et al. |
| 9,359,618 B2 | 6/2016 | Roy et al. |
| 9,382,551 B2 | 7/2016 | Roy et al. |
| 9,493,788 B2 | 11/2016 | Gao et al. |
| 9,567,607 B2 | 2/2017 | Wilson et al. |
| 9,587,250 B2 | 3/2017 | Gao et al. |
| 9,593,346 B2 | 3/2017 | Roy et al. |
| 9,597,363 B2 | 3/2017 | Roy et al. |
| 9,617,561 B2 | 4/2017 | Roy et al. |
| 9,677,089 B2 | 6/2017 | Gao et al. |
| 9,719,106 B2 | 8/2017 | Wilson et al. |
| 9,737,618 B2 | 8/2017 | Wilson et al. |
| 9,770,011 B2 | 9/2017 | Wilson et al. |
| 9,783,824 B2 | 10/2017 | Kay et al. |
| 9,790,472 B2 | 10/2017 | Gao et al. |
| 9,856,469 B2 | 1/2018 | Lisowski et al. |
| 9,884,071 B2 | 2/2018 | Wilson et al. |
| 9,890,365 B2 | 2/2018 | Wang et al. |
| 10,041,090 B2 | 8/2018 | Gao et al. |
| 10,113,182 B2 | 10/2018 | Roy et al. |
| 10,137,176 B2 | 11/2018 | Wilson et al. |
| 10,138,295 B2 | 11/2018 | Wilson et al. |
| 10,149,873 B2 | 12/2018 | Roy et al. |
| 10,155,931 B2 | 12/2018 | Lock et al. |
| 10,167,454 B2 | 1/2019 | Wang et al. |
| 10,179,176 B2 | 1/2019 | Kay et al. |
| 10,265,417 B2 | 4/2019 | Wilson et al. |
| 10,266,846 B2 | 4/2019 | Gao et al. |
| 10,301,648 B2 | 5/2019 | Vandenberghe et al. |
| 10,301,650 B2 | 5/2019 | Gao et al. |
| 10,308,958 B2 | 6/2019 | Gao et al. |
| 10,335,466 B2 | 7/2019 | Kotin et al. |
| 10,385,119 B2 | 8/2019 | Wilson et al. |
| 10,385,320 B2 | 8/2019 | Kay et al. |
| 10,406,173 B2 | 9/2019 | Wilson et al. |
| 10,406,244 B2 | 9/2019 | Kay et al. |
| 10,485,883 B2 | 11/2019 | Wilson et al. |
| 10,501,757 B2 | 12/2019 | Roy et al. |
| 10,508,286 B2 | 12/2019 | Gao et al. |
| 10,526,617 B2 | 1/2020 | Gao et al. |
| 10,532,111 B2 | 1/2020 | Kay et al. |
| 10,544,432 B2 | 1/2020 | Gao et al. |
| 10,570,395 B2 | 2/2020 | Hou et al. |
| 10,577,627 B2 | 3/2020 | Kotin et al. |
| 10,584,337 B2 | 3/2020 | Sah et al. |
| 10,590,435 B2 | 3/2020 | Gao et al. |
| 10,597,660 B2 | 3/2020 | Sah et al. |
| 10,612,041 B2 | 4/2020 | Barzel et al. |
| 10,626,382 B2 | 4/2020 | Wang et al. |
| 10,626,415 B2 | 4/2020 | Vandenberghe et al. |
| 10,647,758 B2 | 5/2020 | Wilson et al. |
| 10,647,998 B2 | 5/2020 | Wilson et al. |
| 10,695,441 B2 | 6/2020 | Wilson et al. |
| 10,722,598 B2 | 7/2020 | Wilson et al. |
| 2004/0132042 A1 | 7/2004 | Frankard et al. |
| 2005/0148076 A1 | 7/2005 | Allen |
| 2010/0260800 A1 | 10/2010 | Bartlett et al. |
| 2013/0035472 A1 | 2/2013 | Horlick et al. |
| 2013/0296409 A1 | 11/2013 | Miller et al. |
| 2013/0323226 A1 | 12/2013 | Wilson et al. |
| 2016/0333375 A1 | 11/2016 | Chen |
| 2017/0067908 A1 | 3/2017 | Nakai et al. |

FOREIGN PATENT DOCUMENTS

| | | |
|---|---|---|
| WO | WO-2019079496 A2 | 4/2019 |
| WO | WO-2020072683 A1 | 4/2020 |
| WO | WO-2020160508 A1 | 8/2020 |

OTHER PUBLICATIONS

Adachi et al.: Adeno-associated virus-binding antibodies detected in cats living in the Northeastern United States lack neutralizing activity. Sci Rep. 10(1):10073 (2020) doi: 10.1038/s41598-020-66596-4.

Adachi et al.: Drawing a high-resolution functional map of adeno-associated virus capsid by massively parallel sequencing. Nat Commun. 5:3075 (2014) doi: 10.1038/ncomms4075.

Cabanes-Creus et al.: Codon-Optimization of Wild-Type Adeno-Associated Virus Capsid Sequences Enhances DNA Family Shuffling while Conserving Functionality. Mol Ther Methods Clin Dev. 12:71-84 (2018) doi: 10.1016/j.omtm.2018.10.016.

Deverman, et al. Cre-dependent selection yields AAV variants for widespread gene transfer to the adult brain. Nature biotechnology34.2 (Feb. 2016): 204.

Dong et al.: Characterization of genome integrity for oversized recombinant AAV vector. Mol Ther. 18(1):87-92 (2010) doi: 10.1038/mt.2009.258.

Earley et al.: Adeno-associated Virus (AAV) Assembly-Activating Protein Is Not an Essential Requirement for Capsid Assembly of AAV Serotypes 4, 5, and 11. J Virol. 91(3):e01980-16 (2017) doi: 10.1128/JVI.01980-16.

Earley et al.: Identification and characterization of nuclear and nucleolar localization signals in the adeno-associated virus serotype 2 assembly-activating protein. J Virol. 89(6):3038-48 (2015) doi: 10.1128/JVI.03125-14 Epub Dec. 31, 2014.

Fischer et al.: Direct injection into the dorsal root ganglion: technical, behavioral, and histological observations. J Neurosci Methods. 199(1):43-55 (2011) doi: 10.1016/j.jneumeth.2011.04.021.

Grimm et al.: Liver transduction with recombinant adeno-associated virus is primarily restricted by capsid serotype not vector genotype. J Virol. 80(1):426-439 (2006) doi: 10.1128/JVI.80.1.426-439.2006.

Grimm et al.: Preclinical in vivo evaluation of pseudotyped adeno-associated virus vectors for liver gene therapy. Blood. 102(7):2412-2419 (2003).

Huang et al.: Cell Type-Specific TRAnscription-Dependent Directed Evolution (TRADE) Identifies Novel AAV Capsids Capable of Enhanced Neuronal Transduction in Mice and Non-Human Primates. Molecular Therapy. 27(4S1):24-25 (2019).

Inagaki et al.: The role of DNA-PKcs and artemis in opening viral DNA hairpin termini in various tissues in mice. J Virol. 81(20):11304-21 (2007) doi: 10.1128/JVI.01225-07.

Kawano et al.: An experimental and computational evolution-based method to study a mode of co-evolution of overlapping open reading frames in the AAV2 viral genome. PLoS One. 8(6):e66211 (2013) doi: 10.1371/journal.pone.0066211.

Kay et al.: Looking into the safety of AAV vectors. Nature. 424(6946):251 (2003) doi: 10.1038/424251b.

Kotchey et al.: A potential role of distinctively delayed blood clearance of recombinant adeno-associated virus serotype 9 in robust cardiac transduction. Mol Ther. 19(6):1079-89 (2011) doi: 10.1038/mt.2011.3.

Kotterman, et al. Engineering adeno-associated viruses for clinical gene therapy. Nature reviews Genetics 15.7 (2014): 445-451.

Manno et al.: Successful transduction of liver in hemophilia by AAV-Factor IX and limitations imposed by the host immune response. Nature Medicine. 12(3):342-347 (2006).

McCaffrey et al.: The host response to adenovirus, helper-dependent adenovirus, and adeno-associated virus in mouse liver. Mol Ther. 16(5):931-41 (2008) doi: 10.1038/mt.2008.37.

Nakai et al.: A limited number of transducible hepatocytes restricts a wide-range linear vector dose response in recombinant adeno-associated virus-mediated liver transduction. J Virol. 76(22):11343-9 (2002) doi: 10.1128/jvi.76.22.11343-11349.2002.

Nakai et al.: AAV serotype 2 vectors preferentially integrate into active genes in mice. Nat Genet. 34(3):297-302 (2003) doi: 10.1038/ng1179.

Nakai et al.: Helper-independent and AAV-ITR-independent chromosomal integration of double-stranded linear DNA vectors in mice. Mol Ther. 7(1):101-11 (2003) doi: 10.1016/s1525-0016(02)00023-0.

Ohashi et al.: Modified infusion procedures affect recombinant adeno-associated virus vector type 2 transduction in the liver. Hum Gene Ther. 16(3):299-306 (2005) doi: 10.1089/hum.2005.16.299.

(56) References Cited

OTHER PUBLICATIONS

PCT/US2020/016273 aInternational Search Report and Written Opinion dated Jun. 23, 2020.
Powers et al.: A Quantitative Dot Blot Assay for AAV Titration and Its Use for Functional Assessment of the Adeno-associated Virus Assembly-activating Proteins. J Vis Exp. (136):56766 (2018). doi: 10.3791/56766.
Wang et al.: AAV vectors containing rDNA homology display increased chromosomal integration and transgene persistence. Mol Ther. 20(10):1902-11 (2012) doi: 10.1038/mt.2012.157.
Yu et al.: Intraganglionic AAV6 results in efficient and long-term gene transfer to peripheral sensory nervous system in adult rats. PLoS One. 8(4):e61266 (2013) doi: 10.1371/journal.pone.0061266.
PCT/US2020/016273 International Preliminary Report on Patentability dated Aug. 12, 2021.

\* cited by examiner

Anti-GFP

GFP      Anti-HuC/D

6. Recover and sequence hSynI-driven transcripts

ATGGCTGCCGATGGTTATCTTCCAGATTGGCTCGAGGACAACCTTAGTGAAGG
AATTCGCGAGTGGTGGGCTTTGAAACCTGGAGCCCCTCAACCCAAGGCAAATC
AACAACATCAAGACAACGCTCGAGGTCTTGTGCTTCCGGGTTACAAATACCTTG
GACCCGGCAACGGACTCGACAAGGGGGAGCCGGTCAACGCAGCAGACGCGG
CGGCCCTCGAGCACGACAAGGCCTACGACCAGCAGCTCAAGGCCGGAGACAA
CCCGTACCTCAAGTACAACCACGCCGACGCCGAGTTCCAGGAGCGGCTCAAAG
AAGATACGTCTTTTGGGGGCAACCTCGGGCGAGCAGTCTTCCAGGCCAAAAAG
AGGCTTCTTGAACCTCTTGGTCTGGTTGAGGAAGCGGCTAAGACGGCTCCTGG
AAAGAAGAGGCCTGTAGAGCAGTCTCCTCAGGAACCGGACTCCTCCGCGGGTA
TTGGCAAATCGGTGCACAGCCCGctaaaaagagactcaatttcggtcagactggcgacacagag
tcagtcccagaccctcaaccaatcggagaacctcccgcagcccctcaggtgtgggatctcttacaatggcttcaggt
ggtggcgcaccagtggcagacaataacgaaggtgccgatggagtgggtagttcctcgggaaattggcattgcgattc
ccaatggctgggggacagagtcatcaccaccagcacccgaacctgggccctgcccacctacaacaatcacctcta
caagcaaatctccaacagcacatctggaggatcttcaaatgacaacgcctacttcggctacagcacccctgggggt
attttgacttcaacagattccactgccacttctcaccacgtgactggcagcgactcatcaacaacaactggggattccg
gcctaagcgactcaacttcaagctcttcaacattcaggtcaaagaggttacggacaacaatggagtcaagaccatcg
ccataaccttaccagcacggtccaggtcttcacggactcagactatcagctcccgtacgtgctcgggtcggctcacg
agggctgcctcccgccgttcccagcggacgttttcatgattcctcagtacgggtatctgacgcttaatgatggaagcca
ggccgtgggtcgttcgtccttttactgcctggaatatttcccgtcgcaaatgctaagaacgggtaacaacttccagttcag
ctacgagtttgagaacgtacctttccatagcagctacgctcacagccaaagcctggaccgactaatgaatccactcat
cgaccaatacttgtactatctctcaaagactattaacggttctggacagaatcaacaaacgctaaaattcagtgtggcc
ggacccagcaacatggctgtccagggaagaaactacatacctggacccagctaccgacaacaacgtgtctcaacc
actgtgactcaaaacaacaacagcgaatttgcttggcctggagcttcttcttgggctctcaatggacgtaatagcttgat
gaatcctggacctgctatgccagccacaaagaaggagaggaccgtttctttcctttgtctggatctttaatttttggcaa
acaaggaactggaagagacaacgtggatgcggacaaagtcatgataaccaacgaagaagaaattaaaactact
aacccggtagcaacggagtcctatggacaagtggccacaaaccaccagagtgcccaagcacaggcgcagaccg
gctgggttcaaaaccaaggaatacttccgggtatggtttggcaggacagagatgtgtacctgcaaggacccatttggg
ccaaaattcctcacacggacggcaactttcacccttctccgctgatgggagggtttggaatgaagcacccgcctcctc
agatcctcatcaaaaacacacctgtacctgcggatcctccaacggccttcaacaaggacaagctgaactctttcatca
cccagtattctactggccaagtcagcgtggagatcgagtgggagctgcagaaggaaaacagcaagcgctggaac
ccggagatccagtacacttccaactattacaagtctaataatgttgaatttgctgttaatactgaaggtgtatatagtgaac
cccgccccattggcaccagatacCTGACTCGTAATCTGTAA

FIG. 5

Splice acceptor

Splice donor

ATGGCTGCTGACGGTTATCTTCCAGATTGGCTCGAGGACAACCTTTCTGAAGGC
ATTCGTGAGTGGTGGGCTCTGAAACCTGGAGTCCCTCAACCCAAAGCGAACCA
ACAACACCAGGACAACCGTCGGGGTCTTGTGCTTCCGGGTTACAAATACCTCG
GACCCGGTAACGGACTCGACAAAGGAGAGCCGGTCAACGAGGCGGACGCGGC
AGCCCTCGAACACGACAAAGCTTACGACCAGCAGCTCAAGGCCGGTGACAACC
CGTACCTCAAGTACAACCACGCCGACGCCGAGTTTCAGGAGCGTCTTCAAGAA
GATACGTCTTTTGGGGGCAACCTTGGCAGAGCAGTCTTCCAGGCCAAAAAGAG
GATCCTTGAGCCTCTTGGTCTGGTTGAGGAAGCAGCTAAAACGGCTctggaaaga
agaggcctgtagatcagtctcctcaggaaccggactcatcatctggtgttggcaaatcgggcaaacagcctgccaga
aaaagactaaatttcggtcagactggcgactcagagtcagtccagaccctcaacctctcggagaaccaccagcag
cccccacaagtttgggatctaatacaatggcttcaggcggtggcgcaccaatggcagacaataacgagggtgccga
tggagtgggtaattcctcaggaaattggcattgcgattcccaatggctgggcgacagagtcatcaccaccagcacca
gaacctgggccctgcccacttacaacaaccatctctacaagcaaatctccagccaatcaggagcttcaaacgacaa
ccactactttggctacagcacccttggggtatttgactttaacagattccactgccacttctcaccacgtgactggca
gcgactcattaacaacaactggggattccggcccaagaaactcagcttcaagctcttcaacatccaagttaaagagg
tcacgcagaacgatggcacgacgactattgccaataaccttaccagcacggttcaagtgtttacggactcggagtatc
agctcccgtacgtgctcgggtcggcgcaccaaggctgtctcccgccgtttccagcggacgtcttcatggtccctcagtat
ggatacctcaccctgaacaacggaagtcaagcggtgggacgctcatccttttactgcctggagtacttcccttcgcaga
tgctaaggactggaaataacttccaattcagctataccttcgaggatgtaccttttcacagcagctacgctcacagcca
gagtttggatcgcttgatgaatcctcttattgatcagtatctgtactacctgaacagaacgcaaggaacaacctctggaa
caaccaaccaatcacggctgcttttagccaggctgggcctcagtctatgtctttgcaggccagaaattggctacctgg
gccctgctaccggcaacagagactttcaaagactgctaacgacaacaacaacagtaactttccttggacagcggcc
agcaaatatcatctcaatggccgcgactcgctggtgaatccaggaccagctatggccagtcacaaggacgatgaag
aaaaatttttccctatgcacggcaatctaatatttggcaaagaagggacaacggcaagtaacgcagaattagataat
gtaatgattacggatgaagaagagattcgtaccaccaatcctgtggcaacagagcagtatggaactgtggcaaata
acttgcagagctcaaatacagctcccacgactagaactgtcaatgatcaggggccttacctggcatggtgtggcaa
gatcgtgacgtgtaccttcaaggacctatctgggcaaagattcctcacacggatggacactttcatccttctcctctgatg
ggaggctttggactgaaacatccgcctcctcaaatcatgatcaaaaatactccggtacCGGCAAATCCTCC
GACGACTTTCAGCCCGGCCAAGTTTGCTTCATTTATCACTCAGTACTCCACTGG
ACAGGTCAGCGTGGAAATTGAGTGGGAGctacagaaagaaaacagcaaacgttggaatccag
agattcagtacacttccaactacaacaagtctgttaatgtggactttactgtagacactaatggtgtttatagtgaacctcg
ccctattggaacccggtatctcacACGAAACTTGTAA

FIG. 7A

ATGGCTGCTGACGGTTATCTTCCAGATTGGCTCGAGGACAACCTTTCTGAAGGC
ATTCGTGAGTGGTGGGCTCTGAAACCTGGAGTCCCTCAACCCAAAGCGAACCA
ACAACACCAGGACAACCGTCGGGGTCTTGTGCTTCCGGGTTACAAATACCTCG
GACCCGGTAACGGACTCGACAAAGGAGAGCCGGTCAACGAGGCGGACGCGGC
AGCCCTCGAACACGACAAAGCTTACGACCAGCAGCTCAAGGCCGGTGACAACC
CGTACCTCAAGTACAACCACGCCGACGCCGAGTTTCAGGAGCGTCTTCAAGAA
GATACGTCTTTTGGGGGCAACCTTGGCAGAGCAGTCTTCCAGGCCAAAAAGAG
GATCCTTGAGCCTCTTGGTCTGGTTGAGGAAGCAGCTAAAACGGCTctggaaaga
agaggcctgtagatcagtctcctcaggaaccggactcatcatctggtgttggcaaatcgggcaaacagcctgccaga
aaaagactaaatttcggtcagactggcgactcagagtcagtcccagaccctcaacctctcggagaaccaccagcag
cccccacaagtttgggatctaatacaatggcttcaggcggtggcgcaccaatggcagacaataacgagggtgccga
tggagtgggtaattcctcaggaaattggcattgcgattcccaatggctgggcgacagagtcatcaccaccagcacca
gaacctgggccctgcccacttacaacaaccatctctacaagcaaatctccagccaatcaggagcttcaaacgacaa
ccactactttggctacagcaccccttgggggtattttgactttaacagattccactgccacttctcaccacgtgactggca
gcgactcattaacaacaactggggattccggcccaagaaactcagcttcaagctcttcaacatccaagttaaagagg
tcacgcagaacgatggcacgacgactattgccaataaccttaccagcacggttcaagtgtttacggactcggagtatc
agctcccgtacgtgctcgggtcggcgcaccaaggctgtctcccgccgtttccagcggacgtcttcatggtccctcagtat
ggatacctcaccctgaacaacggaagtcaagcggtgggacgctcatccttttactgcctggagtacttcccttcgcaga
tgctaaggactggaaataacttccaattcagctataccttcgaggatgtaccttttcacagcagctacgctcacagcca
gagtttggatcgcttgatgaatcctcttattgatcagtatctgtactacctgaacagaacgcaaggaacaacctctggaa
caaccaaccaatcacggctgcttttttagccaggctgggcctcagtctatgtctttgcaggccagaaattggctacctgg
gccctgctaccggcaacagagactttcaaagactgctaacgacaacaacaacagtaactttccttggacagcggcc
agcaaatatcatctcaatggccgcgactcgctggtgaatccaggaccagctatggccagtcacaaggacgatgaag
aaaaattttccctatgcacggcaatctaatatttggcaaagaagggacaacggcaagtaacgcagaattagataat
gtaatgattacggatgaagaagagattcgtaccaccaatcctgtggcaacagagcagtatggaactgtggcaaata
acttgcagagctcaaatacagctcccacgactagaactgtcaatgatcagggggccttacCTGGCATGGTGT
GGCAAGATCGTGACGTGTACCTTCAAGGACCTATCTGGGCAAAGATTCCTCACA
CGGATGGACACTTTCATCCTTCTCCTCTGATGGGAGGCTTTGGACTGAAACATC
CGCCTCCTCAAATCATGATCAAAATACTCCGGTACCGGCAAATCCTCCGACGA
CTTTCAGCCCGGCCAAGTTTGCTTCATTTATCACTCAGTACTCCACTGGACAGG
TCAGCGTGGAAATTGAGTGGAGctacagaaagaaaacagcaaacgttggaatccagagattcag
tacacttccaactacaacaagtctgttaatgtggactttactgtagacactaatggtgtttatagtgaacctcgccctattg
gaacccggtatctcacACGAAACTTGTAA

FIG. 9B atggctgccgatggttatcttccagattggctcgaggacaacctctctgagggcattcgcgagtggtgggacttgaaac
ctggagccccgaagcccaaagccaaccagcaaaagcaggacgacggccggggtctggtgcttcctggctacaag
tacctcggaccccttcaacggactcgacaaggggagcccgtcaacgcggcggacgcagcggccctcgagcacg
acaaggcctacgaccagcagctcaaagcgggtgacaatccgtacctgcggtataaccacgccgacgccgagtttc
aggagcgtCTgcaagaagatacgtcttttgggggcaacctcgggcgagcagtcttccaggccaagaagcgggttc
tcgaacctctcggtctggttgaggaaggcgctaagacggctcCTgaaagaaacgtccggtagagcagtcgccac
aagagccagactcctcctcgggcatcggcaagacaggccagcagcccgCTaaaagagactcaattttggtcag
actggcgactcagagtcagtccccgatccacaacctctcggagaacctccagcaaccccgctgctgtgggaccta
ctacaatggcttcaggcggtggcgcaccaatggcagacaataacgaaggcgccgacggagtgggtaatgcctcag
gaaattggcattgcgattccacatggctgggcgacagagtcatcaccaccagcacccgcacctgggccttgcccac
ctacaataaccacctctacaagcaaatctccagtgcttcaacgggggccagcaacgacaaccactcttcggctac
agcacccctggggggtattttgatttcaacagattccactgccacttttcaccacgtgactggcagcgactcatcaacaa
caattggggattccggcccaagagactcaacttcaaactcttcaacatccaagtcaaggaggtcacgacgaatgatg
gcgtcacaaccatgctaataacctttACcagcacggttcaagtcttctcggactcggagtaccagcttccgtacgtcct
cggctctgcgcaccagggctgcctccctccgttcccggcggacgtgttcatgattccgcaatacggctacctgacgctc
aacaatggcagccaagccgtgggacgttcatcctttactgcCTggaatatttcccttctcagatgctgagaacgggc
aacaacttACcttcagctacacctttgaggaagtgcctttccacagcagctacgcgcacagccagagcctggaccg
gctgatgaatcctctcatcgaccaatacctgtattACCTgaacagaactcaaaatcagtccggaagtgcccaaaac
aaggacttgctgtttagccgtgggtctccagctggcatgtctgttcagcccaaaaactggctACctggaccctgttatcg
gcagcagcgcgtttCTaaaacaaaaacagacaacaacaacagcaatttACctggactggtgcttcaaaatataa
cctcaatgggcgtgaatccatcatcaaccctggcactgctatggcctcacacaaagacgacgaagacaagttcttcc
catgagcggtgtcatgattttggaaaagagagcgccggagcttcaaacaCTgcattggacaatgtcatgattacag
acgaagaggaaattaaagccactaaccctgtggccaccgaaagatttgggaccgtggcagtcaatttccagagca
gcagcacagaccctgcgaccggagatgtgcatgctatgggagcattACctggcatggtgtggcaagatagagacg
tgtACctgcagggtcccatttgggccaaaattcctcacacagatggacactttcacccgtctcctcttatgggcggcttt
ggactcaagaacccgcctcctcagatcctcatcaaaaacacgcctgttcctgcgaatcctccggcggagttttcagct
acaaagtttgcttcattcatcacccaatactccacaggacaagtgagtgtggaaattgaatgggagCTgcagaaag
aaaacagcaagcgctggaatcccgaagtgcagtacacatccaattatgcaaaatctgccaacgttgattttactgtgg
acaacaatggactttatactgagcctcgccccattggcacccgttACcttACccgtcccctgtaa

FIG. 10

METHODS FOR USING TRANSCRIPTION-DEPENDENT DIRECTED EVOLUTION OF AAV CAPSIDS

RELATED CASES

This application is a continuation of International Patent Application No. PCT/US2020/016273 filed on Jan. 31, 2020, and entitled "METHODS FOR USING TRANSCRIPTION-DEPENDENT DIRECTED EVOLUTION OF AAV CAPSIDS," which claims priority to U.S. Provisional Patent Application No. 62/799,603, filed on Jan. 31, 2019, and entitled "TRANSCRIPTION-DEPENDENT DIRECTED EVOLUTION OF AAV CAPSIDS," each of which are hereby incorporated by reference in their entireties.

STATEMENT REGARDING FEDERALLY SPONSORED RESEARCH

This invention was made with government support under Grant No. NS088399 awarded by the National Institutes of Health/National Institute of Neurological Disorders and Stroke. The government has certain rights in the invention.

SEQUENCE LISTING

The instant application contains a Sequence Listing which has been submitted electronically in ASCII format and is hereby incorporated by reference in its entirety. Said ASCII copy, created on Jun. 2, 2021, is named 60255-701.301-Sequence-Listing.txt and is 108,980 bytes in size.

TECHNICAL FIELD

This disclosure relates to viral vectors used in gene delivery. More specifically, this disclosure relates to a method for transcription-dependent directed evolution and adeno-associated virus ("AAV") vectors that are selected by using this method.

BACKGROUND

Recombinant adeno-associated virus ("AAV") vectors are among the most promising for in vivo gene delivery. The usefulness of AAV vectors has been expanded since a number of naturally occurring new serotypes and subtypes were isolated from human and non-human primate tissues. Gao et al., *J Virol* 78, 6381-6388 (2004) and Gao et al., *Proc Natl Acad Sci USA* 99, 11854-11859 (2002). Among the newly-identified AAV isolates, AAV serotype 8 (AAV8) and AAV serotype 9 (AAV9) have gained attention because AAV vectors derived from these two serotypes can transduce a variety of organs including the liver, heart, skeletal muscles and central nervous system with high efficiency following systemic administration. Ghosh et al., *Mol Ther* 15, 750-755 (2007); Pacak et al., *Circ Res* 99, 3-9 (2006); Inagaki et al., *Mol Ther* 14, 45-53 (2006); Zhu et al., *Circulation* 112, 2650-2659 (2005); Wang et al., *Nat Biotechnol* 23, 321-328 (2005); Nakai et al., *J Virol* 79, 214-224 (2005); and Foust et al., *Nature Biotechnol* 23, 321-328 (2009). This robust transduction by AAV8 and 9 vectors has been ascribed to strong tropism for these cell types, efficient cellular uptake of vectors, and/or rapid uncoating of virion shells in cells. Thomas et al., *J Virol* 78, 3110-3122 (2004). In addition, emergence of capsid-engineered AAV vectors with better performance has significantly broadened the utility of AAV as a vector toolkit. Asokan et al., *Mol Ther* 20, 699-708 (2012).

A proof-of-concept using AAV-mediated gene therapy has been shown in many preclinical animal models of human diseases. Phase I/II clinical studies have shown promising results for the treatment for hemophilia B (Nathwani et al., *N Engl J Med* 71, 1994-2004 (2014)), lipoprotein lipase deficiency (Carpentier et al., *J Clin Endocrinol Metab* 97, 1635-1644 (2012)), Leber congenital amaurosis (Jacobson et al., *Arch Ophthalmol* 130, 9-24 (2012) and Pierce and Bennett, *Cold Spring Harb Perspect Med* 5, a017285 (2015)), among others (reviewed in Mingozzi and High, *Nat Rev Genet* 12, 341-355 (2011) and Wang et al., *Nat Rev Drug Discov* 18, 358-378 (2019)).

Despite this promise, human studies have also revealed unexpected issues and potential challenges in AAV-mediated gene therapy. Manno et al., *Nat Med* 12, 342-347 (2006). In addition, despite rapid progress in our understanding of AAV biology and capsid-phenotype relationships (Adachi et al., *Nat Commun* 5, 3075, (2014); Grimm et al., *Hum Gene Ther* 28, 1075-1086, (2017); and Ogden et al., *Science* 366, 1139-1143, (2019)), there remain many desirable properties for clinical AAV vectors that we cannot rationally design.

To this end, high throughput screening methods for identifying novel AAV capsids with such desirable phenotypes have been employed. In particular, the development of in vivo AAV library selection strategies have produced a variety of designer AAV variants capable of highly efficient transduction of previously refractory cell types (reviewed in Kotterman and Schaffer, *Nat Rev Genet* 15, 445-451 (2014) and Grimm et al., *Mol Ther* 23, 1819-1831 (2015)).

The earliest attempts at in vivo library selection (1st Generation) relied on recovery of vector genome DNA from dissected tissue. Theoretically, this strategy results in recovery of both effective AAV variants, as well as AAV variants that mediate some, but not all of the steps required for vector-mediated transgene expression (FIG. 1). Thus, screening a diverse library of synthetic AAV variants potentially leads to a high background recovery of AAV variants that are completely ineffective gene therapy vectors. Furthermore, targeting a specific cell type requires further processing, such as fluorescence-activated cell sorting or laser capture microdissection. Nonetheless, there have been several reports of successfully employing this technology. Excoffon et al., *Proc Natl Acad Sci USA* 106, 3865-3870 (2009); Grimm et al., *J Virol* 82, 5887-5911 (2008); Lisowski et al., *Nature* 506, 382-386 (2014); and Dalkara et al., *Sci Transl Med* 5, 189ra176 (2013). However, a landmark study in 2016 by Deverman et al. showed that this process could be greatly improved upon by using a Cre-dependent selection strategy (2nd Generation). Deverman et al., *Nat Biotechnol* 34, 204-209 (2016). Cre-dependent library selection takes advantage of the selective ability of Cre recombinase to act on double-stranded DNA, but not single-stranded DNA, in order to invert vector genome DNA containing a primer binding sequence. Inversion of this sequence allows for direction-selective PCR to specifically amplify viral DNA delivered to cells by AAV variants that are able to undergo the late stage of transduction at which double stranded DNA is formed from single-stranded AAV genomes. In addition, the use of Cre driver lines facilitates selective expression of Cre recombinase in a cell type-specific manner, allowing for selection of novel AAV variants that efficiently transduce. Indeed, the use of Cre-dependent selection allowed the authors to develop an AAV9 variant, AAV-PHP.B, that is capable of 40 times greater transduction than the parental AAV9 following systemic administration in C57BL/6J mice. Deverman et al., *Nat Biotechnol* 34, 204-209 (2016). Unfortunately, it has recently become clear that the enhancement exhibited by AAV-PHP.B in mice does not translate to the non-human primate context (Matsuzaki et al. 2018 and Hordeaux et al. 2019). Surprisingly, the enhancement does not even extend to all commonly used mouse strains (Matsuzaki et al. 2018 and Hordeaux et al. 2019). There is, therefore, a strong impetus to accelerate the development of clinically relevant AAV vectors by performing AAV library selection experiments in primate models. However, unlike the AAV variant selection in mice where a plethora of cell type-specific transgenic Cre driver lines are already established, Cre-dependent selection is not tractable in clinically relevant large animals, including non-human primates, because Cre transgenic animals are not readily available.

We therefore sought to develop a next-generation selection strategy (3rd Generation) with similar or better selective stringency as that provided by Cre-dependent selection, but without the need for Cre recombinase. In order to accomplish this goal, we developed the TRAnscription-dependent Directed Evolution system, or TRADE. In the transcription-dependent selection, we express the AAV cap gene as a non-coding antisense mRNA driven by a cell type-specific enhancer-promoter. Recovery of this antisense transcript by RT-PCR allows for stringent recovery of AAV cap genes at the level of vector-mediated mRNA expression in a specific cell type without the use of Cre recombinase. Targeting of different cell types merely requires cloning of a different cell type-specific enhancer-promoter into the plasmid construct. Thus, TRADE is a highly flexible system that can be applied in a wide variety of contexts, including the non-human primate context for development of enhanced AAV vectors for clinical gene therapy. Note that the same principle can be used for expressing AAV cap gene in an sense orientation. However, the sense strand approach results in expression of immunogenic capsid proteins in target cells and is therefore less ideal than the antisense strand approach employed by the TRADE system.

SUMMARY

This disclosure provides a next-generation directed evolution strategy, termed TRAnscription-dependent Directed Evolution ("TRADE"), that selects for AAV capsid transduction at the level of cell type-specific or ubiquitous mRNA expression. The method described herein provides the following advantages over Cre recombination-based AAV targeted evolution ("CREATE"), the most contemporary methods for AAV capsid directed evolution reported in the literature. Deverman et al., *Nat Biotech* 34, 204-209 (2016). First, the CREATE system requires Cre expression, which can be attained either by exogenously-delivered Cre expression or by the use of Cre-transgenic animals. In contrast, the TRADE system does not require Cre-transgenic animals; therefore, it can be applied to animals and cultured cells derived from any animal species and can be readily adapted to large animals, including non-human primates. Second, unlike the CREATE system, in which the cell-type specific selection is applied at the level of AAV viral genome conversion from single-stranded DNA to double-stranded DNA, TRADE allows for cell type-specific selection at the level of AAV genome transcription. Therefore, the TRADE system can provide greater selective pressure than the CREATE system. Third, multiple directed evolution schemes (e.g., neuron-specific, astrocyte-specific, oligodendrocyte-specific, and microglia-specific) can be integrated into one AAV capsid library and selection for AAV vectors targeting each cell type can be performed in a single animal. Fourth, any cell type-specific or tissue/organ-specific enhancers/promoters or ubiquitous enhancers/promoters can be readily used for AAV capsid directed evolution aimed at identification of cell type-specific or ubiquitous novel AAV capsids with enhanced potency. Fifth, the TRADE methodology is not limited to the genus Dependoparvovirus, including the common AAVs that have been used for gene delivery, but can also be applied more broadly to the family Parvoviridae, including in the genera Bocaparvoviruses and Erythroparvoviruses other than AAV (e.g., bocaviruses), and even more broadly to an DNA virus.

This disclosure also provides novel AAV capsid mutants. TRADE technology was used to identify novel AAV vectors that mediate neuronal transduction in the brain following intravenous administration. Application of TRADE in C57BL/6J mice and a rhesus macaque resulted in the identification of new AAV capsids that can transduce neurons more efficiently and more specifically than AAV9 in the mouse and non-human primate brain following intravenous administration. In addition, we identified a novel AAV capsid that can transduce an undefined cell population or populations, that reside in the lung and are potentially of neuronal origin, 5 to 18 times better than the AAV9.

The present disclosure also provides a method to prevent splicing of antisense mRNA of the AAV capsid gene. Antisense pre-mRNA transcribed from the AAV cap gene open reading frame ("ORF") can be spliced making (a) truncated mRNA species. To our knowledge, this is a new discovery that has never previously been reported. Such splicing has the potential to hinder effective recovery of full-length antisense mRNA of the AAV cap ORF, which is essential for TRADE when a wide region of the cap ORF is mutagenized. This disclosure provides a novel strategy to prevent splicing of antisense mRNA of the cap gene.

The TRADE system described herein uses antisense mRNA to recover capsid sequence information, TRADE using sense strand mRNA (i.e., sense strand TRADE) is also feasible using the same principle. However, it should be noted that the sense strand TRADE approach results in expression of immunogenic capsid proteins in target cells and therefore is presumably less ideal than the antisense strand approach.

BRIEF DESCRIPTION OF THE FIGURES

(FIG. 2A) A map of the AAV vector genome in a TRADE configuration (AAV-TRADE). A cell type-specific enhancer-promoter is placed in an antisense orientation to drive AAV cap gene transcription expression as antisense mRNA. A polyadenylation signal (pA) derived from the simian virus 40 (SV40) genome is placed within the AAV genome intron in an antisense orientation to terminate antisense AAV cap gene mRNA transcription. The eGFP open-reading frame (ORF) can be placed as depicted to serve as a reporter or facilitate enrichment of transduced cells by FACS; however, such a marker gene is not strictly necessary for TRADE. A ubiquitous promoter such as the CAG promoter can be also used in TRADE in placed of cell type-specific enhancers-promoters to identify AAV capsids that can transduce a variety of cell types. A cell type-specific enhancer-promoter can be placed upstream of the AAV cap gene ORF to drive expression of the AAV cap gene mRNA transcripts in a sense orientation (i.e., sense strand TRADE). However, this approach may not be ideal for TRADE because AAV capsid protein would be expressed in target cells, which may result in undesired biological consequences in the directed evolution process. (FIG. 2B) During AAV vector production in HEK293 cells, and in the presence of the adenoviral helper functions, the AAV2 viral p40 promoter drives cap gene expression (forward transcription) and cell type-specific transcripts are suppressed, leading to successful production of recombinant AAV vectors containing the AAV-TRADE vector genome. Following transduction of a specific cell type, the cell type-specific enhancer-promoter is activated, driving expression of eGFP and the antisense cap mRNA sequence, while the transcriptional activity of the p40 promoter remains inactive in transduced cells due to a lack of adenoviral helper functions. The entire cap gene ORF can be recovered by reverse transcription (RT)-PCR using antisense cap gene mRNA as a template that is expressed in a cell type-specific manner. We have observed that recombinant AAV vectors can be produced successfully at high levels even in the presence of antisense mRNA transcripts expressed due to leaky expression from the human synapsin I gene (hSynI) enhancer-promoter in HEK293 cells. We have also observed that recombinant AAV vectors can be produced successfully at high titers even when we use the CAG promoter that drives expression of antisense AAV cap mRNA transcripts at high levels.

(FIG. 3A) A map of the AAV-PHP.B-hSynI-GFP-TRADE vector genome. (FIG. 3B) To verify the TRADE system, this AAV vector genome was packaged into the AAV-PHP.B capsid as a single-stranded DNA genome and the resulting AAV vector was injected into two 8-week-old C57BL/6J mice intravenously at a dose of $3\times10^{11}$ vector genomes (vg) per mouse. Brain tissue was harvested 12 days post-injection. The brain tissue from one animal was fixed with 4% paraformaldehyde and used for immunofluorescence microscopy and the brain tissue from the other animal was unfixed and used for molecular analysis of AAV vector genome DNA and RNA. (FIG. 3C) Immunofluorescence microscopy image of brain sections stained with anti-GFP antibody confirmed expression of the cell type-specific enhancer-promoter-driven transcript. (FIG. 3D) hSynI enhancer-promoter-driven GFP expression was observed specifically in neurons (anti-HuC/D+). (FIG. 3E) RT-PCR was used to recover the full-length cap ORF sequence (RT+). RT−, a no reverse transcriptase control; Plas, a positive control obtained with DNA-PCR using a plasmid template containing the AAV-PHP.B-hSynI-GFP-TRADE vector genome sequence; NT, a no template PCR control. (FIG. 3F) Sanger sequencing of the RT-PCR product revealed expected splicing of the MVM intron in the antisense transcripts expressed by the hSynI enhancer-promoter (SEQ ID NO:190). The exon-exon junction is highlighted with gray. (FIG. 3G) Sanger sequencing confirmed the insertion of the PHP.B peptide (highlighted with gray) (SEQ ID NO:191).

FIG. 5 An intron identified in antisense mRNA derived from the AAV9 cap gene (SEQ ID NO:192). When the AAV-PHP.B cap gene sequence was transcribed in an antisense orientation in HEK293 cells or Neuro2a cells under the control of the neuron-specific human synapsin I (hSynI) enhancer-promoter, a splicing event was identified with cryptic splice donor and splice acceptor sites (please refer to FIGS. 6A-6F as well). The underlined sequence indicates the intron found within the AAV9 cap ORF. This splicing event was not observed in mouse brain neurons. It should be noted that (1) although the hSynI enhancer-promoter has been used as a neuron-specific element, it has been shown to drive leaky expression in HEK293 cells; and (2) the AAV9 cap ORF sequence used for the intron splicing experiment had the following silent mutations near the C-terminus:

Figure 1:
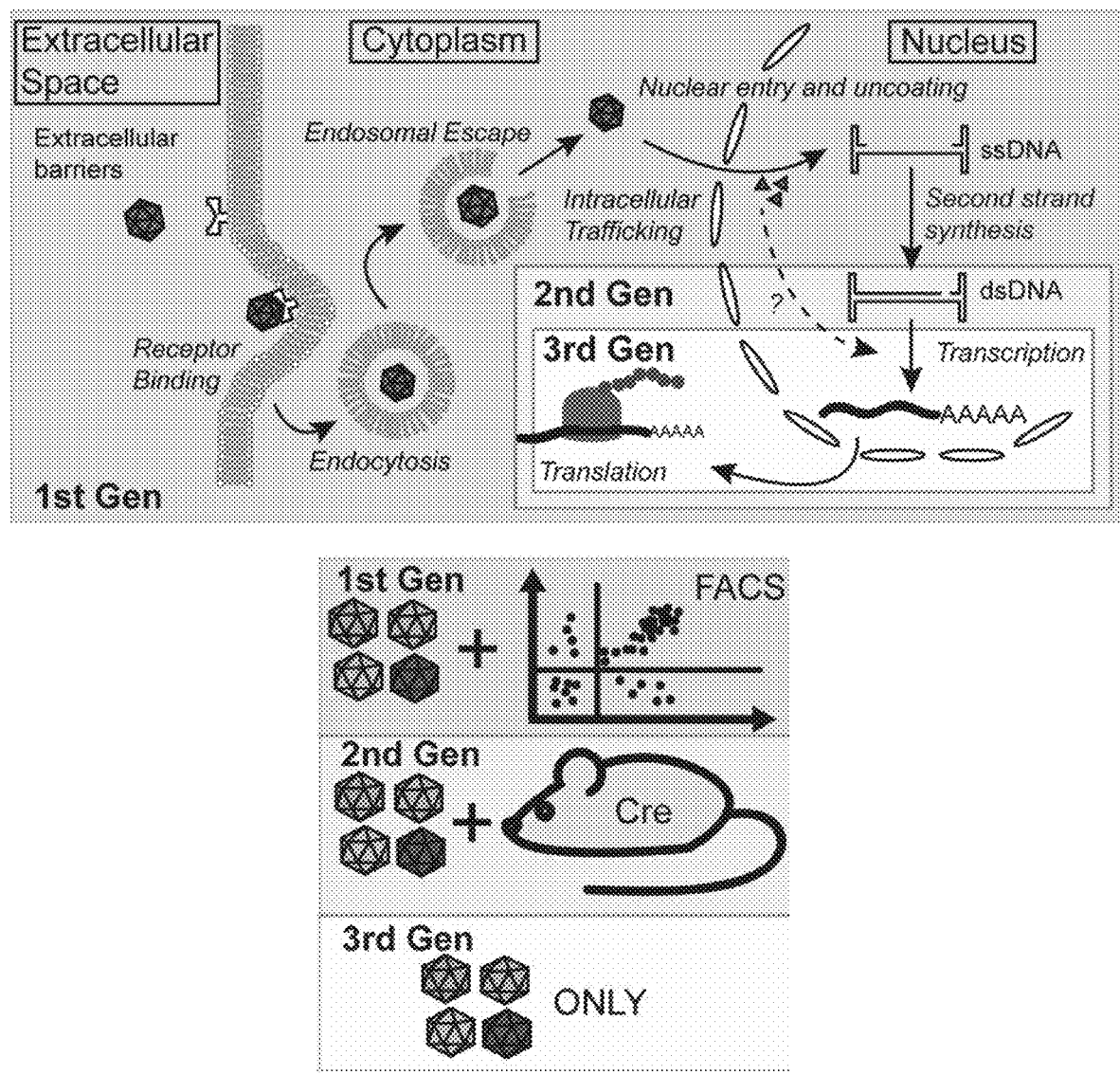
FIG. 1 An overview of in vivo library selection strategies utilized for directed evolution of the AAV capsid. AAV vector-mediated transduction is a multi-step process that requires the virion to overcome extracellular barriers, bind receptors on the target cell, enter the cell via endocytosis, escape the endosome, traffic to the nucleus, uncoat, achieve a double-stranded DNA configuration, and finally undergo transcription/translation. The earliest strategies for in vivo library selection ($1^{st}$ Gen) recovered all vector genome DNA from a tissue sample. Theoretically, this strategy would recover both effective AAV variants, as well as AAV variants that mediate some, but not all of the steps required for vector-mediated transgene expression. In addition, this strategy would also recover AAV vector genome DNA from AAV vector particles that do not enter cells and stay in the extracellular matrix. Thus, screening a diverse library of synthetic AAV variants would lead to a relatively high background recovery of AAV variants that are completely ineffective gene therapy vectors. Furthermore, focusing on a specific cell type requires further processing, such as fluorescence-activated cell sorting (FACS) or laser capture microdissection (LCM). The second generation of library selection ($2^{nd}$ Gen) substantially increased selection stringency by utilizing Cre-dependent recovery of only those AAV variants that are able to achieve the double-strand DNA stage of transduction. Furthermore, driving the expression of Cre with a cell type-specific enhancer-promoter allows for targeting of a specific cell type while retaining the benefits of processing bulk tissue samples. The third generation of library selection ($3^{rd}$ Gen) further builds on AAV directed evolution technology by employing transcription-dependent recovery of AAV variants that are able to mediate transgene mRNA expression from a cell type-specific enhancer-promoter, without the requirement of Cre expression.

```
                                        (SEQ ID NO: 1)
gaaccccgccccattggcacGCgTtacCTGACTCGTAATCTGTAA.
```

The intron sequence is underlined, and the silent mutations that have been introduced into the intron to create an MluI (ACGCGT) recognition site are indicated in uppercase.

FIGS. 6A-6F: Cryptic splice donor (SD) and splice acceptor (SA) sites with the common features of exon-intron junctions present in the AAV cap ORFs in an antisense orientation. Nucleotide sequences of the cap genes derived from 122 naturally occurring AAV strains (serotypes and variants) are aligned using a multiple sequence alignment program (SEQ ID NO 223-316). The exon-intron junctions identified in the AAV9 cap ORF-derived antisense mRNA are indicated with solid lines. The dashed line in the splice acceptor region indicates putative splice acceptor sites in the AAV cap ORFs devoid of the splice acceptor AG/TC sequence at the position expected from the sequence conservation. The dashed line in the splice donor region indicates the splice donor site identified in the AAV3 cap ORF-derived antisense mRNA (please refer to FIGS. 7A-7B). The GT/CA splice donor sites and the AG/TC splice acceptor motifs, followed by a stretch of T's, are the common features of exon-intron junctions and are very well-conserved across many AAV strains. The splice donor and acceptor sites identified in the AAV9 cap ORF shown in this figure have also been identified in the AAV1 cap ORF. For serotypes other than AAV1, 3, 5 and 9, splicing events in antisense mRNA of the AAV cap ORFs are currently under investigation. The highlighted variants are common AAV serotypes.

FIGS. 7A-7B: Introns identified in antisense mRNA derived from the AAV3 cap gene. pAAV3-hnLSP-MCS-TRADE2 is a plasmid carrying the wild-type AAV3 cap ORF placed under a liver-specific enhancer-promoter with an MVM intron (hnLSP). The nucleotide sequence of the AAV3 cap ORF is the same as that of the naturally identified AAV3. HepG2 cells, a human hepatoma cell line, were transfected with plasmid pAAV3-hnLSP-MCS-TRADE2. Antisense mRNA derived from the AAV3 cap ORF was then analyzed by RT-PCR. Sequences of two truncated RT-PCR products were determined by Sanger sequencing following blunt-end TOPO cloning of the PCR products, which revealed introns found within the antisense AAV3 cap ORF (Panels A and B, SEQ ID NO:193). Intron sequences are in lowercase letters with underline. The most upstream splice donor site is found to be only 3 bp away from the splice donor site identified in the AAV9 cap ORF, which is indicated in a dashed line in FIGS. 6B-6F. The most downstream splice acceptor site is found approximately 80 bp upstream of that of the AAV9 cap ORF. Please note that all the splice donor and acceptor sites identified in the AAV3 cap ORF have also been identified in the AAV1 cap ORF.

Figure 8D:
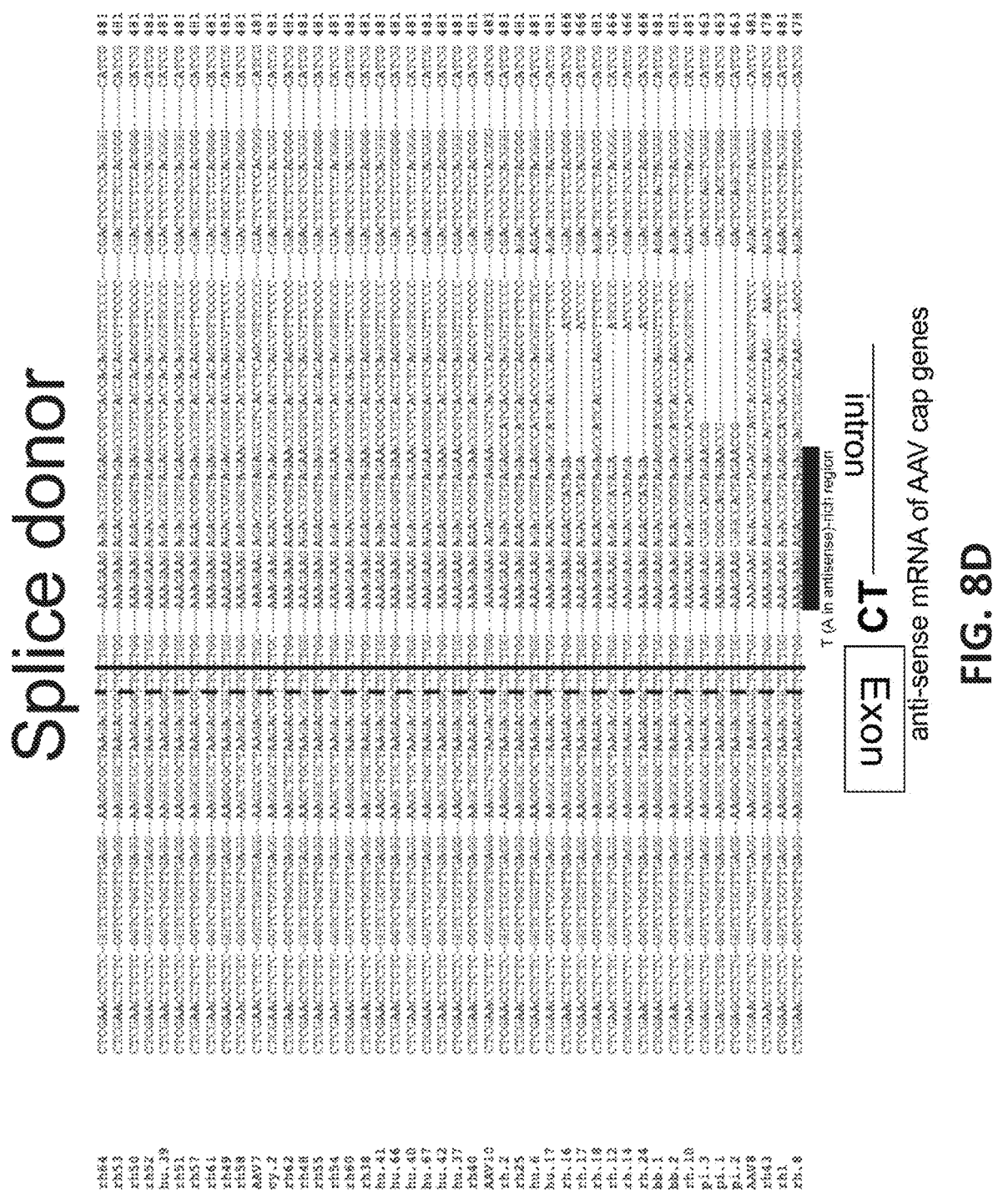
Figure 8E:
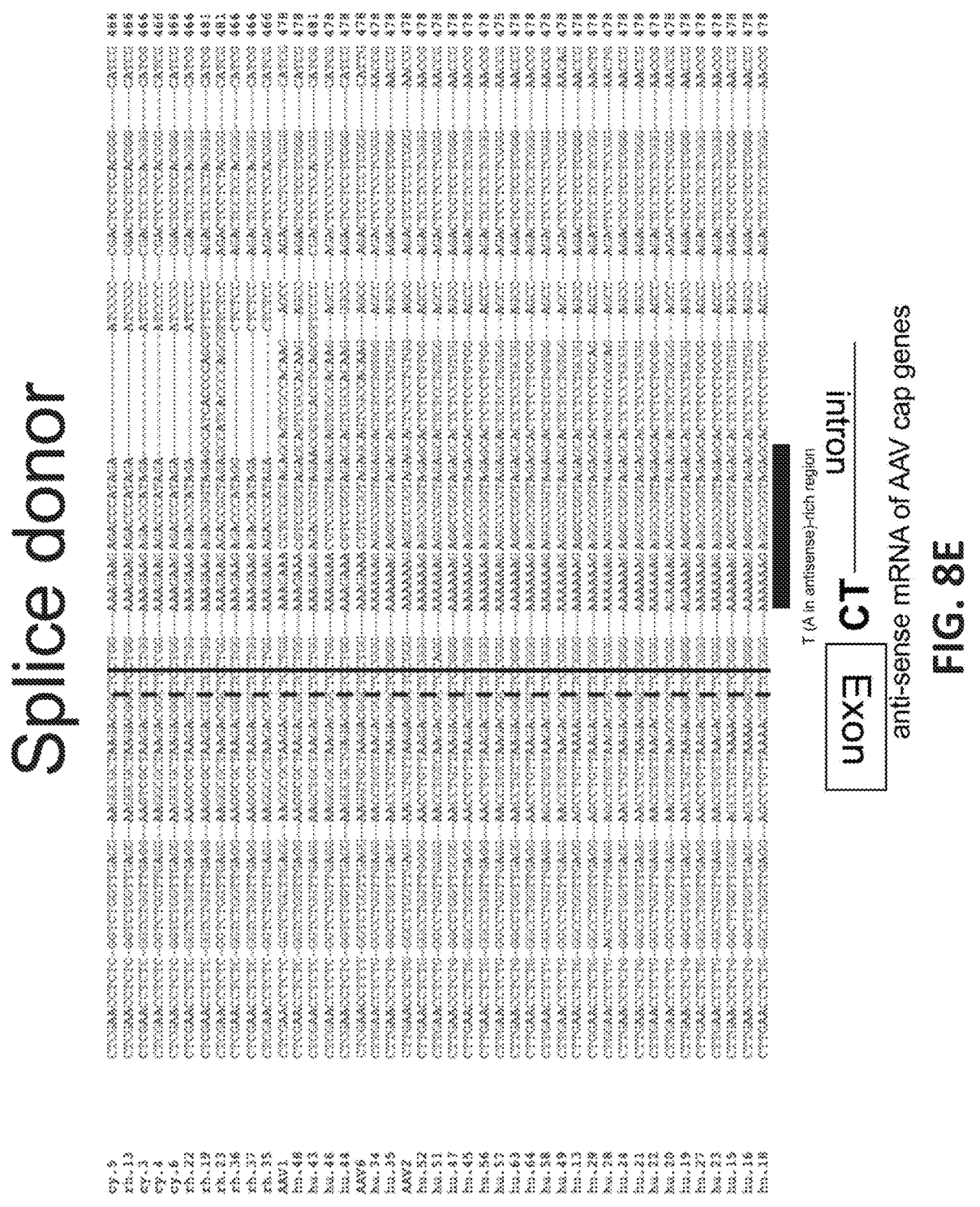
Figure 8F:
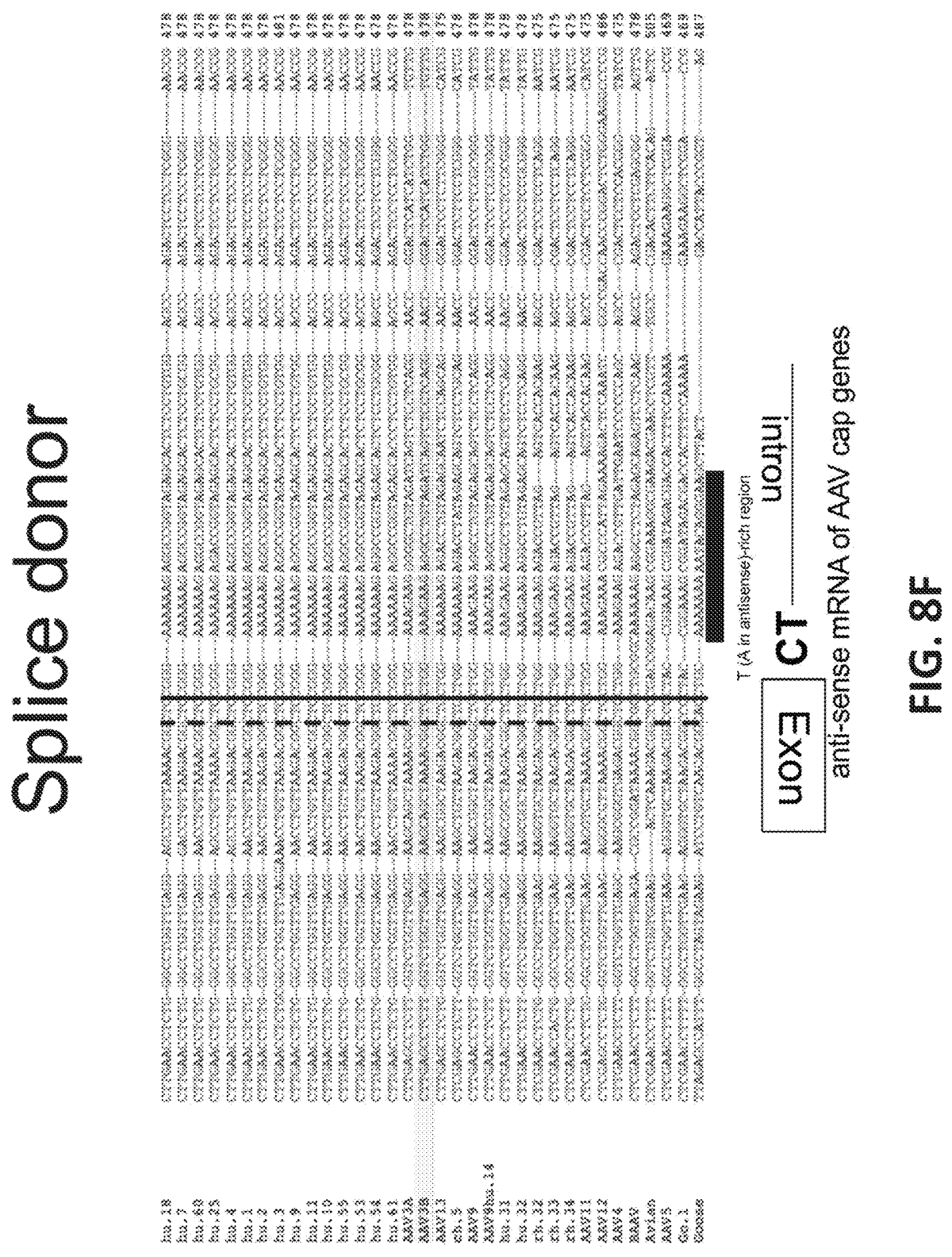

FIGS. 8A-8F. Additional cryptic splice acceptor sites present in the AAV cap ORFs. (FIG. 8A, FIG. 8B, FIG. 8C, FIG. 8D, FIG. 8E, and FIG. 8F) Nucleotide sequences of the cap genes derived from 122 naturally occurring AAV strains (serotypes and variants) are aligned using a multiple sequence alignment program (SEQ ID NO:317-420). The exon-intron junctions at the splice acceptor sites identified in the AAV3 cap ORF-derived antisense mRNA are indicated with solid thin lines. The dashed line in Panel A indicates alternative putative splice acceptor sites near the experimentally determined splice acceptor site. The AG/TC splice acceptor sites, followed by a stretch of T's, are a common feature of exon-intron junctions at splice acceptor sites and are very well conserved across many AAV strains. The AAV3 cap ORF is highlighted. The splice acceptor sites identified in the AAV3 cap ORF shown in Panels A and B have also been identified in the AAV1 cap ORF. As for the AAV5 cap ORF, no splicing events have been observed at any sites in antisense mRNA transcription. For serotypes other than AAV1, 3, 5 and 9, splicing events in antisense mRNA of the AAV cap ORFs are currently under investigation.

Figure 9A:
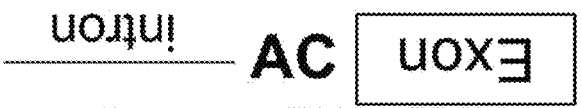
Figure 9B:
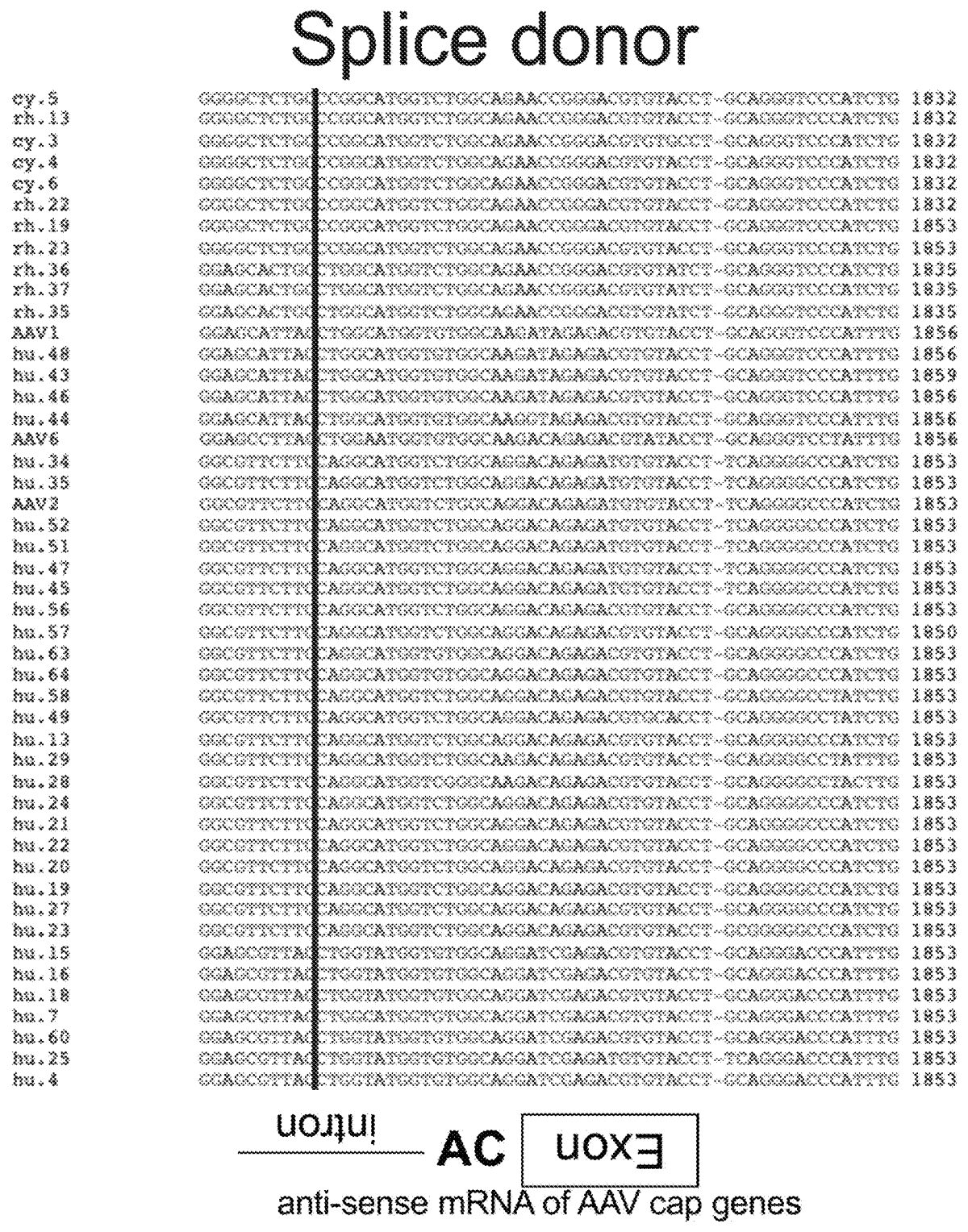
Figure 9C:

FIGS. 9A-9C: Additional potential splice donor sites present in the AAV cap ORFs. Nucleotide sequences of the cap genes derived from 122 naturally occurring AAV strains (serotypes and variants) are aligned using a multiple sequence alignment program (SEQ ID NO:421-461). The exon-intron junctions at the splice donor sites identified in the AAV3 cap ORF-derived antisense mRNA are indicated with a solid line. The GT/CA splice donor consensus sequence at this position is retained by only half of AAV strains. This splice donor site has been identified in the AAV1 cap ORF.

FIG. 10 Splice donor and splice acceptor sites identified in the AAV1 cap ORF. The nucleotide sequence of the AAV1 cap ORF is shown (SEQ ID NO:194). The AAV1 cap ORF was expressed by the hSynI enhancer-promoter in human embryonic kidney (HEK) 293 cells or Neuro2a cells in an antisense orientation. Antisense mRNA derived from the AAV1 cap ORF was then analyzed by RT-PCR. Sequences of RT-PCR products were determined by Sanger sequencing following blunt-end TOPO cloning of the PCR products, which revealed introns found within the AAV1 cap ORF. Exon-intron junctions identified in antisense AAV1 cap mRNA are indicated with AG/TC for the splice donor sites and GT/CA for the splice acceptor sites. AG/TC and GT/CA in uppercase are the consensus two nucleotides at the 5' end and the 3' end of an intron, respectively. Since the splicing occurs in antisense mRNA of the ORF, intron sequences are between CT (splice acceptor) and AC (splice donor) in various combinations in the above sequence. The detailed information about the observed combinations of the splice donors and acceptors is not shown. The two conserved nucleotides at exon-intron junctions (CT or AC) indicated in boldface are those that are highly conserved across different AAV serotypes. The two conserved nucleotides at exon-intron junctions (CT or AC) that are underlined are those that have also been identified in antisense AAV3 or AAV9 cap mRNA transcripts.

Figure 11:
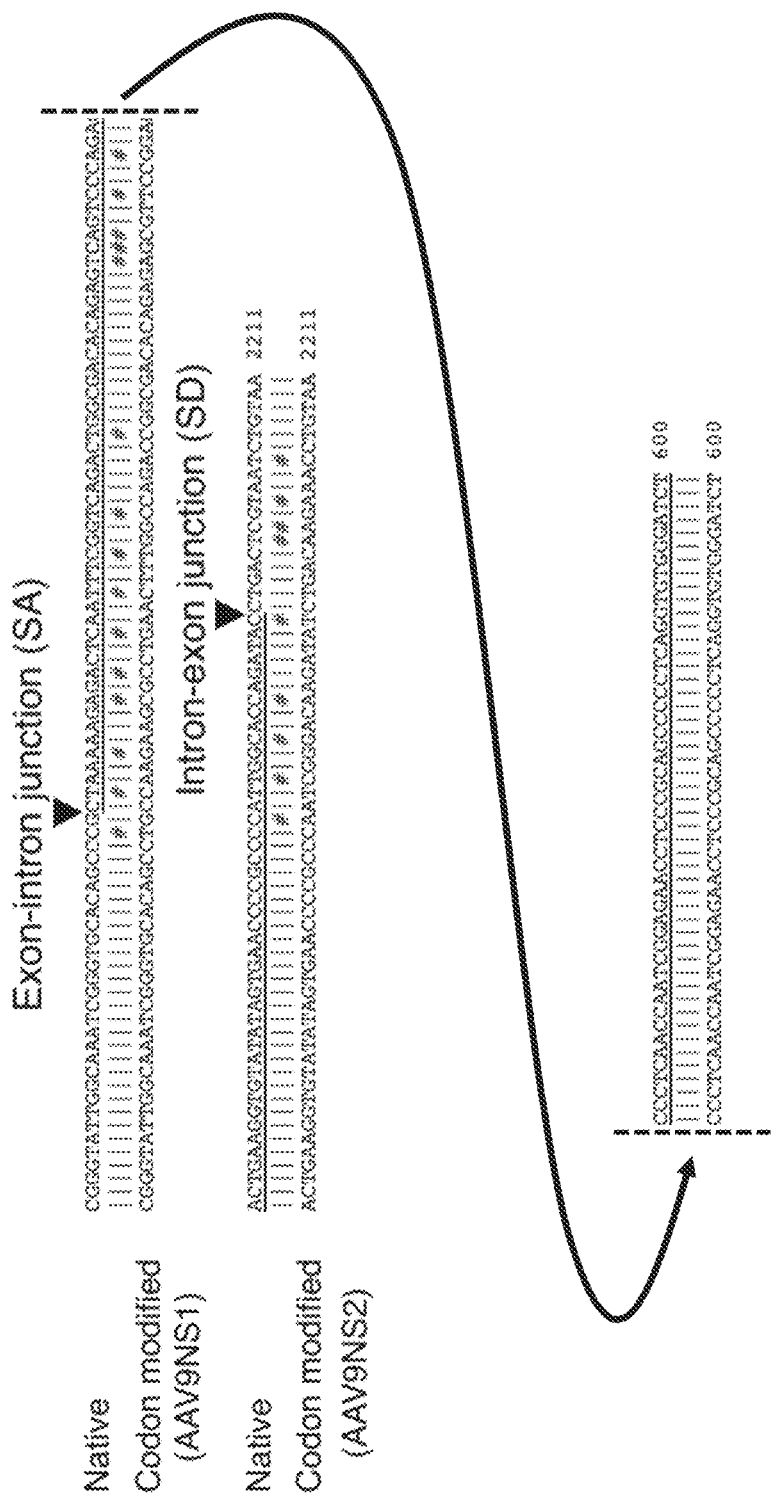

FIG. 11 Splicing-suppressing mutagenesis of the AAV9 cap ORF. Silent mutations are introduced around the splice acceptor (SA) site and/or the splice donor (SD) site in the AAV9 cap ORF to suppress the splicing observed on the antisense mRNA transcripts. The spliced-out intron from the native sequence (SEQ ID NO:195, SEQ ID NO:196) is indicated with underlines. The AAV9NS1 genome (SEQ ID NO:197) has a set of mutations around the SA site while the AAV9NS2 genome (SEQ ID NO:198) has a set of mutations around the SD site. The AAV9NS3 genome has both sets of mutations. The numbers to the right indicate the nucleotide position relative to the first nucleotide of the AAV9 cap ORF.

Figure 4:
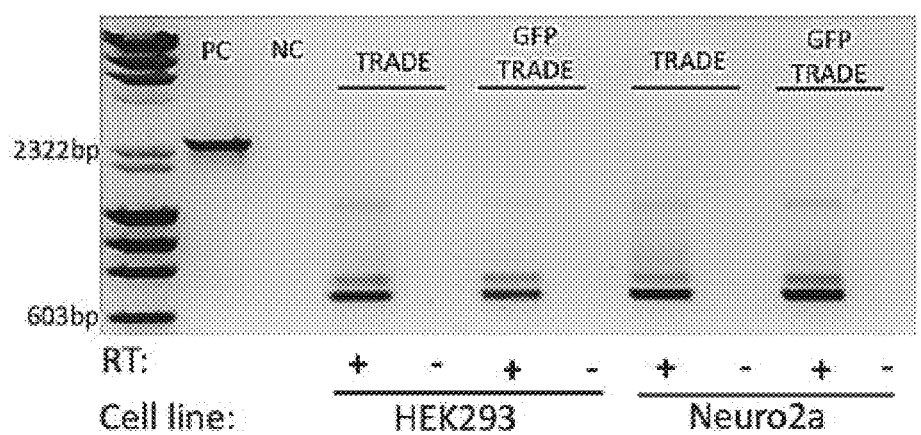
FIG. 4 Splicing of the antisense mRNA of the AAV9 cap ORF. Two cell lines, HEK293 and Neuro2a, were transfected with plasmids containing the AAV9 cap ORF in the TRADE configuration, with or without a GFP reporter. They are indicated as "GFP TRADE" and "TRADE", respectively, in the figure. Cells were harvested 3 days post-transfection, RNA was extracted, and RT-PCR was performed with a set of PCR primers that amplify the full cap ORF sequence. Instead of recovering the expected amplicon size of 2.4 kb as shown in the positive control (PC) lane, we consistently recovered amplicons of approximately 0.7 kb. Sanger sequencing of these RT-PCR products identified a truncation consistent with splicing of a 1.7 kb region of the AAV9 cap ORF indicated in FIG. 5. PC, a positive control using a plasmid template containing the AAV-PHP.B-hSynI-GFP-TRADE vector genome sequence; NC, a no template PCR control.
Figure 6A:
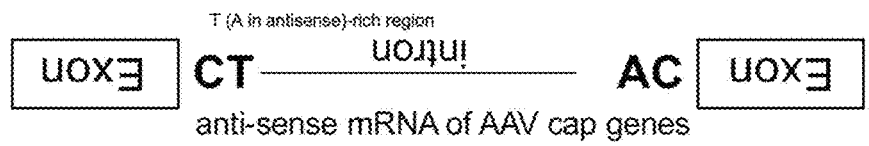
Figure 6B:
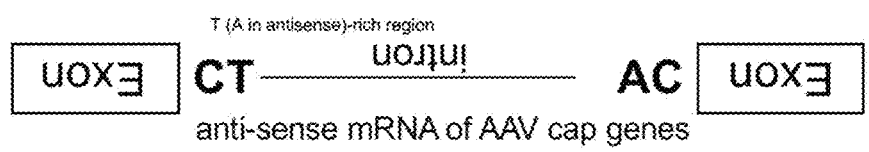
Figure 6C:
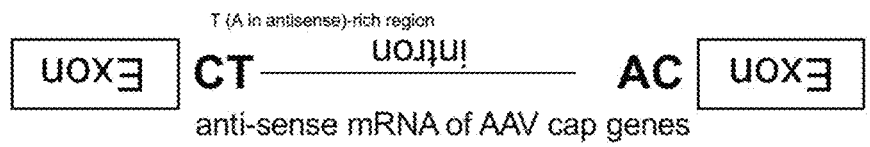
Figure 6D:
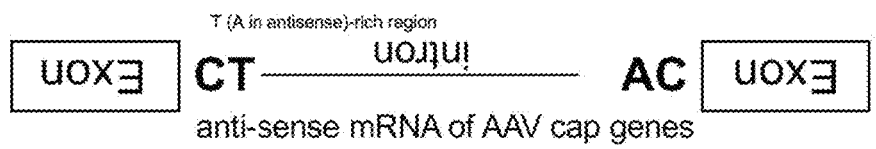
Figure 6E:
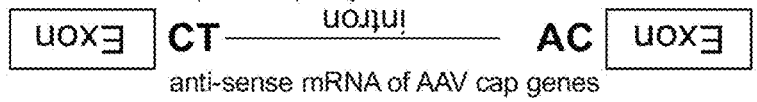
Figure 6F:
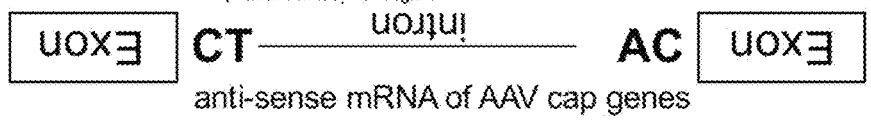
Figure 8A:
Figure 8B:
Figure 8C:
Figure 12:
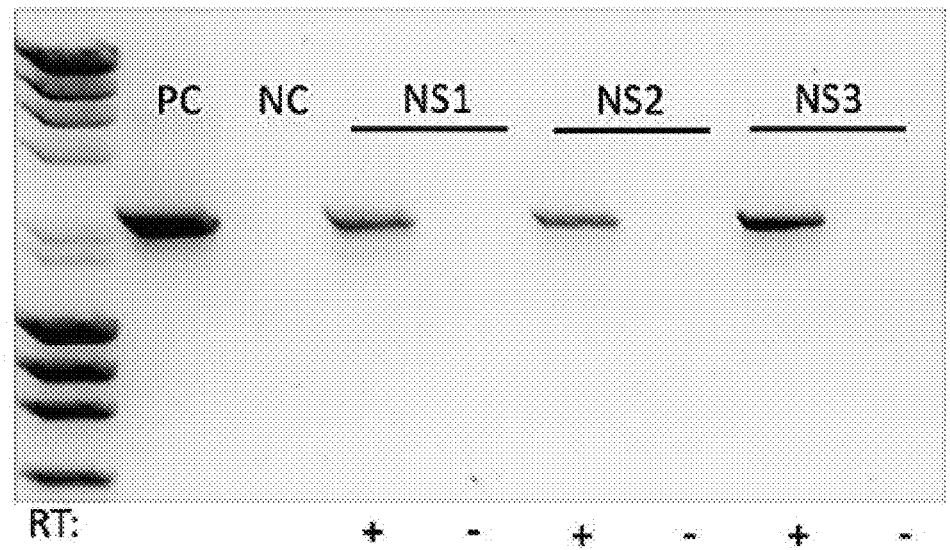

FIG. 12 Mutations introduced around the splice donor and/or accepter site(s) effectively suppress the splicing of antisense mRNA derived from the AAV9 cap ORF. Neuro2a cells were transfected with plasmids containing the AAV9 cap ORF and various potentially splicing-suppressing mutations in the TRADE configuration (NS1-3). RNA was harvested 3 days post-transfection and RT-PCR was performed with a set of PCR primers that can recover the full cap ORF sequence. In stark contrast to results seen in FIG. 4, full-length amplicons were successfully recovered. NS1, the AAV9-TRADE vector genome with a codon-modified splice acceptor. NS2, the AAV9-TRADE vector genome with a codon-modified splice donor. NS3, the AAV9-TRADE vector genome with codon-modified splice acceptor and splice-donor. PC, a positive control using a plasmid template containing the AAV-PHP.B-hSynI-GFP-TRADE vector genome sequence; NC, a no template PCR control.

Figure 13A:
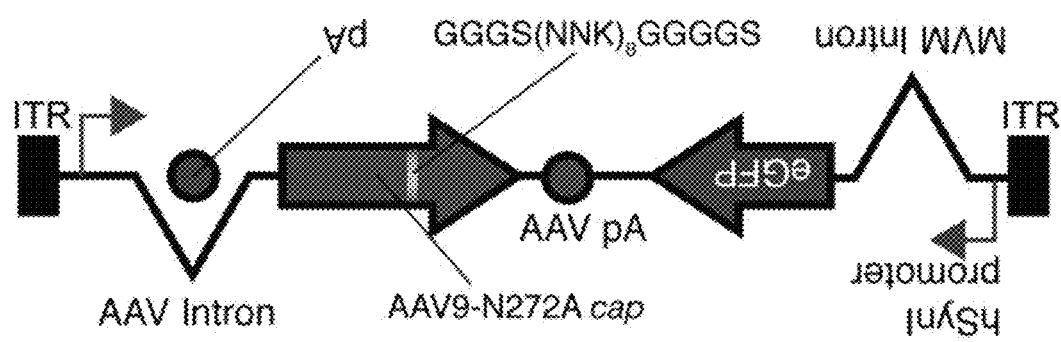
Figure 13B:
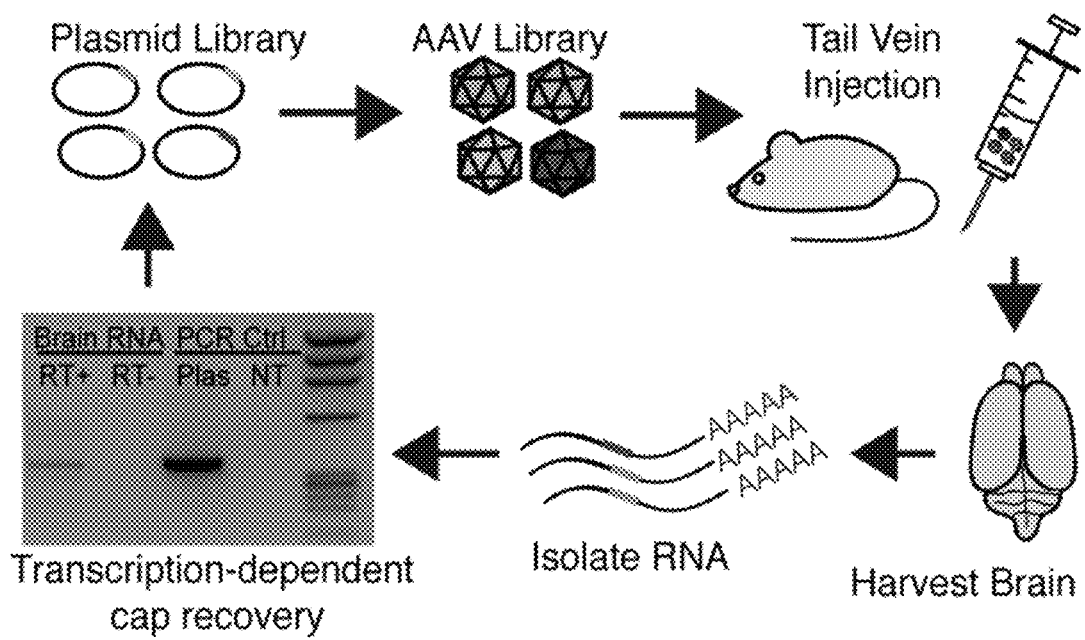

FIGS. 13A-13B: Study design for application of TRADE to identify enhanced AAV variants for brain neuron transduction following systemic AAV vector injection. (A) A map of the AAV9-N272A-hSynI-GFP-TRADE-PepLib vector genome. The hSynI enhancer-promoter is utilized to drive expression specifically in neurons. The liver-detargeted AAV9-N272A cap (PCT/US2017/068050) serves as the platform for AAV library generation. A randomized 8 amino acid peptide encoded by (NNK)s and flanked by glycine-serine linkers (SEQ ID NO:2) was substituted for Q588 of the AAV9-N272A cap sequence (SEQ ID NO:222). (B) The plasmid library was used to produce an AAV library using a triple transfection protocol. The library was purified through PEG precipitation and two rounds of CsCl ultracentrifugation, then injected via tail vein at a dose of $3\times10^{11}$ vg/mouse. Brain tissue was harvested 12 days post-injection. RNA was recovered using TRIzol and RT-PCR was used to recover a fragment of cap containing the peptide insertion, which was subsequently cloned back into the AAV vector plasmid backbone. This was repeated for 3 rounds of selection in C57BL/6J mice. In parallel, a single round of selection was performed in rhesus macaque using a dose of $2.7\times10^{12}$ vg/kg.

FIGS. 14A-14D: Validation of neuronal transduction of the 26 novel AAV capsids in mice and a nonhuman primate by AAV RNA Barcode-Seq. (FIG. 14A) A map of the double-stranded (ds) AAV-hSynI-GFP-BC vector. A pair of two 12 nucleotide-long DNA barcodes (VBCx-L and VBCx-R) are placed under the human synapsin I (hSynI) gene enhancer-promoter. These two virus barcodes (VBCs) can be expressed as transcripts specifically in cells where the hSynI enhancer-promoter is active (i.e., neurons). (FIG. 14B) Neuronal transduction of 26 novel AAV variants, HN1 to HN26, identified by TRADE (5 variants identified in mice and 21 variants identified in a non-human primate) and 3 control AAV capsids (AAV9, AAV9-N272A and AAV-PHP.B) in C57BL/6J and BALB/cJ mice. A DNA/RNA-barcoded dsAAV-hSynI-GFP-BC library (dsAAV-hSynI-GFP-BCLib) containing 26 novel AAV variants identified by TRADE (5 variants identified by TRADE in mice and 21 variants identified by TRADE in a non-human primate) and control AAV capsids (AAV9, AAV9-N272A and AAV-PHP.B) was injected intravenously into three adult male C57BL/6J mice and three adult male BALB/cJ mice at a dose of $5\times10^{11}$ vg per mouse. Two weeks post-injection, various tissues were harvested and analyzed for transduction at AAV vector genome transcripts levels by AAV RNA Barcode-Seq. Transduction levels are expressed as phenotypic difference (PD) values relative to the reference control, AAV9. For the AAV capsid amino acid sequence information of the HN1 to HN26 variants, please refer to Table 3. (FIG. 14C) Neuronal transduction of the 26 novel AAV variants and 3 control AAV capsids in the hippocampus of a rhesus macaque. The same DNA/RNA-barcoded AAV library was injected intravenously into one juvenile male rhesus macaque at a dose of $2\times10^{13}$ vg/kg. Two weeks post-injection, various brain regions were harvested and analyzed for transduction by AAV RNA Barcode-Seq. (FIG. 14D) Relative neuronal transduction efficiencies of 3 TRADE variants, HN1, HN2 and HN3, and AAV-PHP.B were analyzed by AAV RNA Barcode-Seq in 12 different brain regions in the single rhesus macaque used for Panel C. In Panels B, C and D, dashed lines indicate the PD value of AAV9 (i.e., 1.0).

Figure 15A:
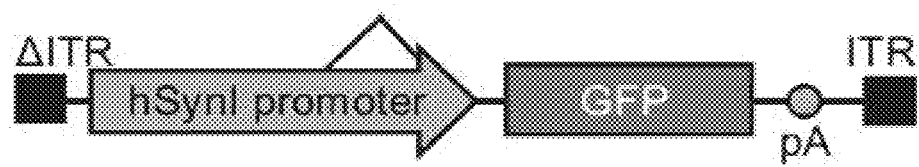
Figure 15B:
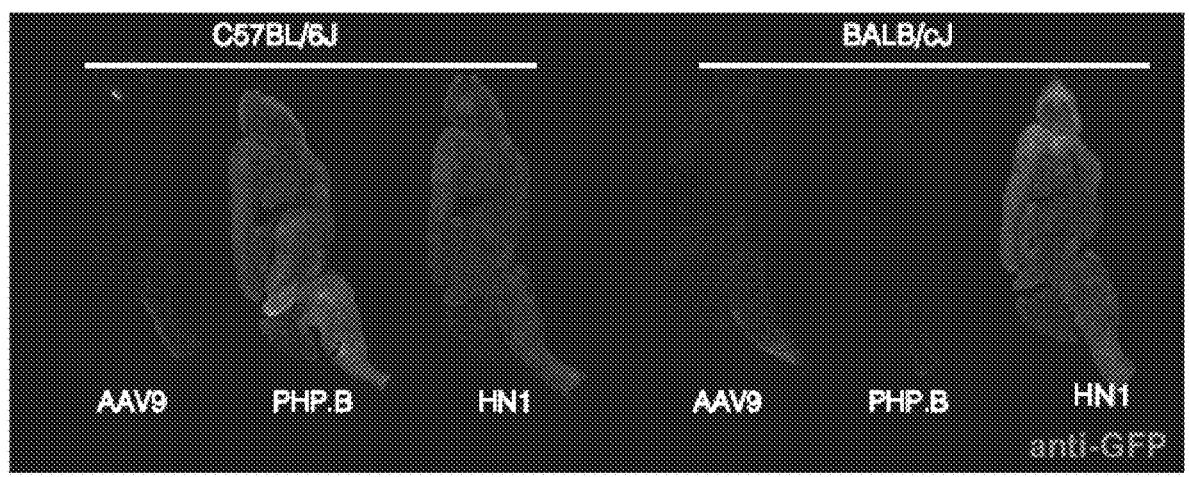
Figure 15C:
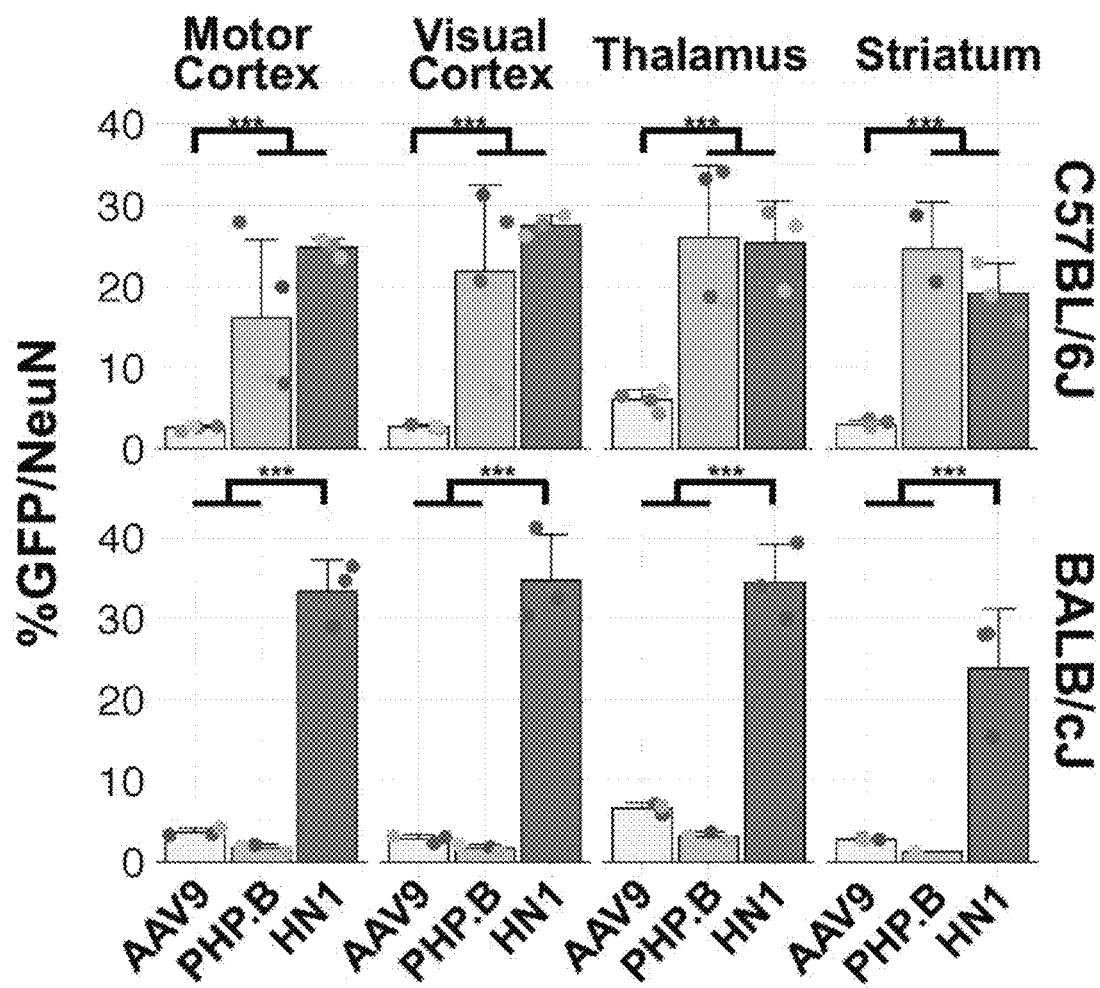
Figure 15D:
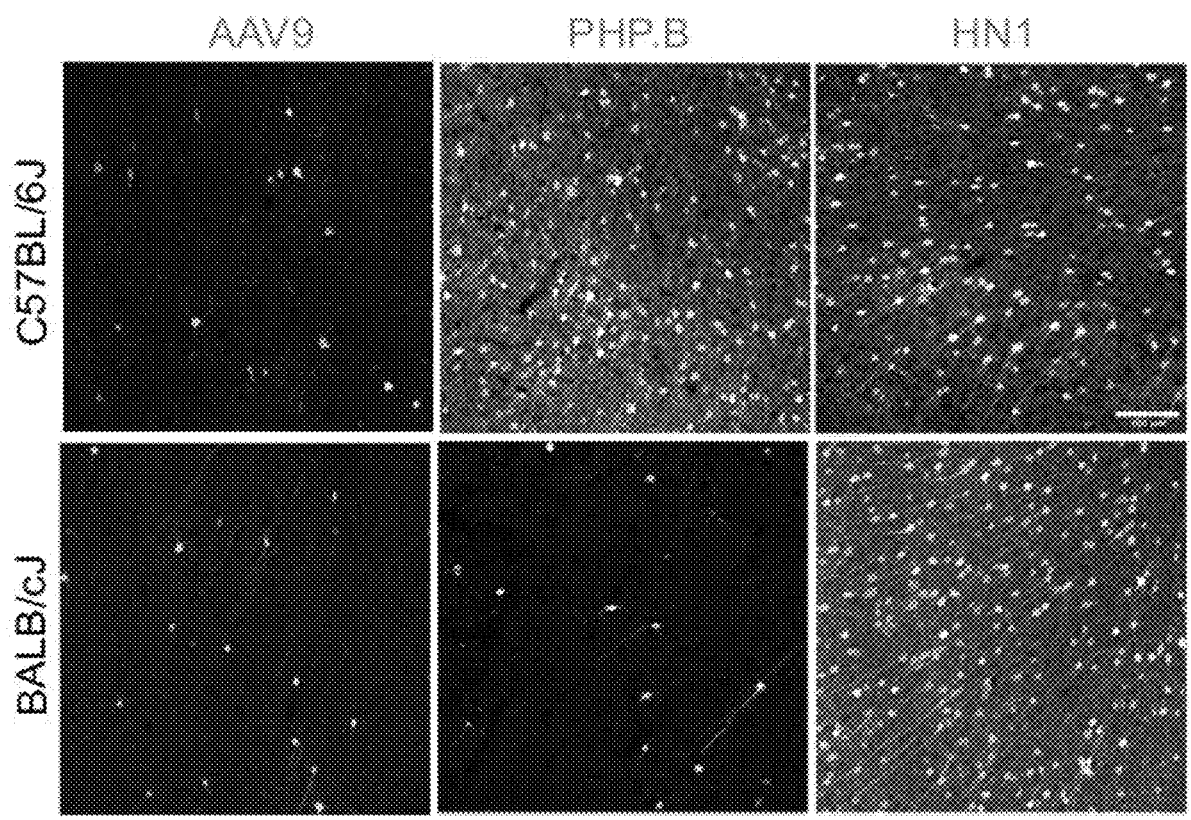
Figure 15E:
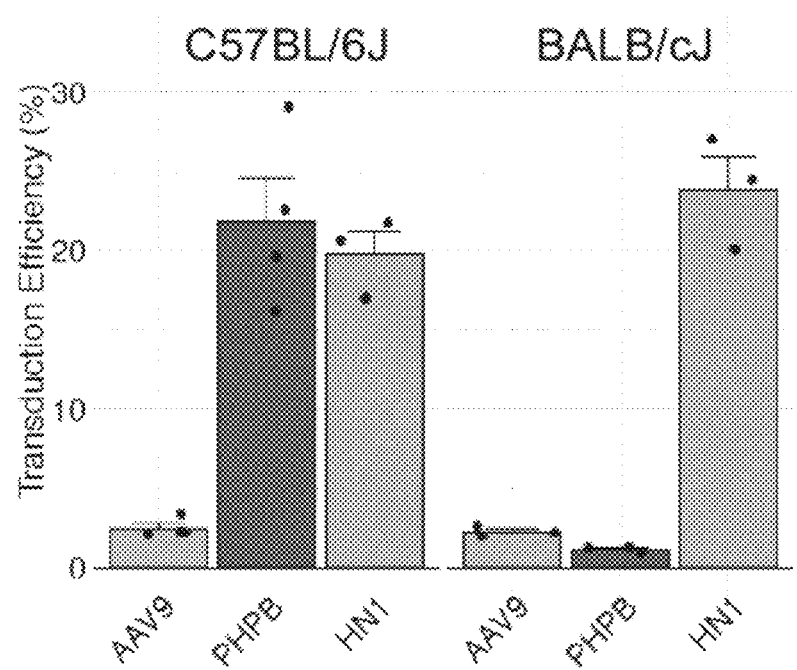

FIGS. 15A-15E: Validation of enhanced neuronal transduction of AAV9-N272A-HN1 in mice using conventional eGFP reporter vectors and histological quantification. We produced AAV9, AAV-PHP.B, and AAV9-N272A-HN1 vectors containing self-complementary AAV genomes expressing eGFP under the control of the hSynI enhancer-promoter (dsAAV-hSynI-eGFP). Purified vectors were administered via the tail vein at a dose of $3\times10^{11}$ vg/mouse into 8-week old male C57BL/6J or BALB/cJ mice (n=4 mice/vector/mouse strain). Three weeks post-injection, mice were transcardially perfused with 4% paraformaldehyde and brain tissue was processed for immunohistochemistry. (FIG. 15A) A map of the self-complementary hSynI-eGFP vector genome. (FIG. 15B) Representative tilescan images of sagittal sections stained with anti-GFP antibody. (FIG. 15C) Quantification of neuronal transduction in (FIG. 15B) based on automated counts of cells expressing eGFP and NeuN in four brain regions. (FIG. 15D) Validation of the automated counting process in (FIG. 15B) and (FIG. 15C). Representative 20× confocal images from visual cortex are shown. Scale bar=100 µm. (FIG. 15E) Quantification of neuronal transduction in (FIG. 15D) based on hand counts of cells expressing eGFP and NeuN by a blinded observer. Error bars represent mean+/−SEM. ***$p<0.001$.

Figure 16A:
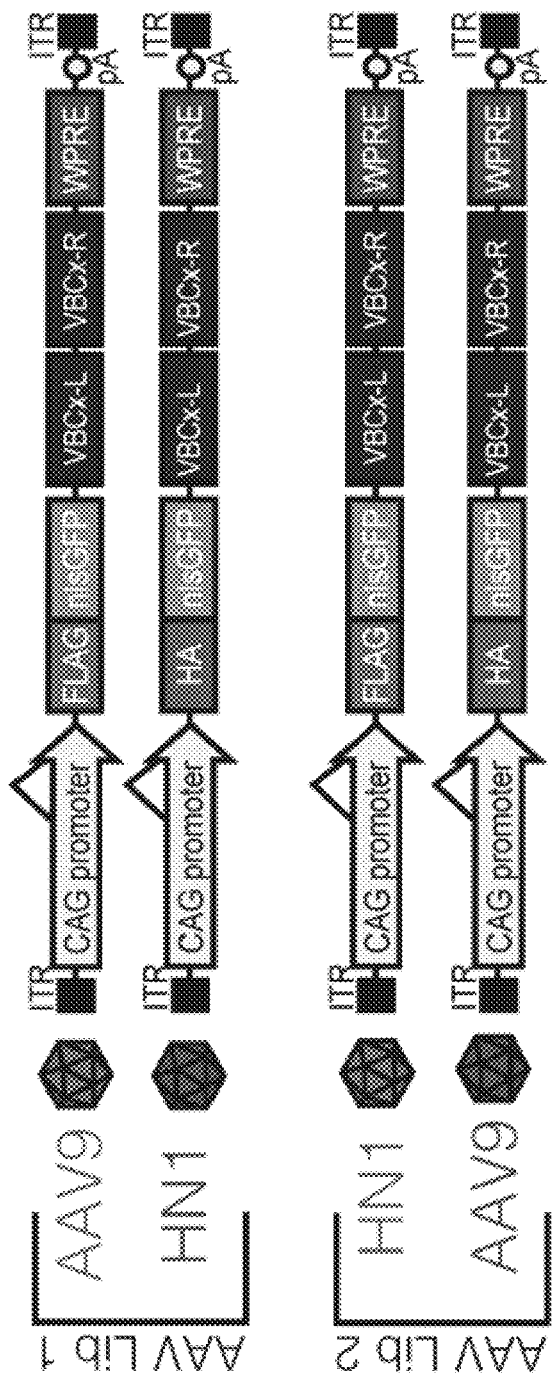
Figure 16B:
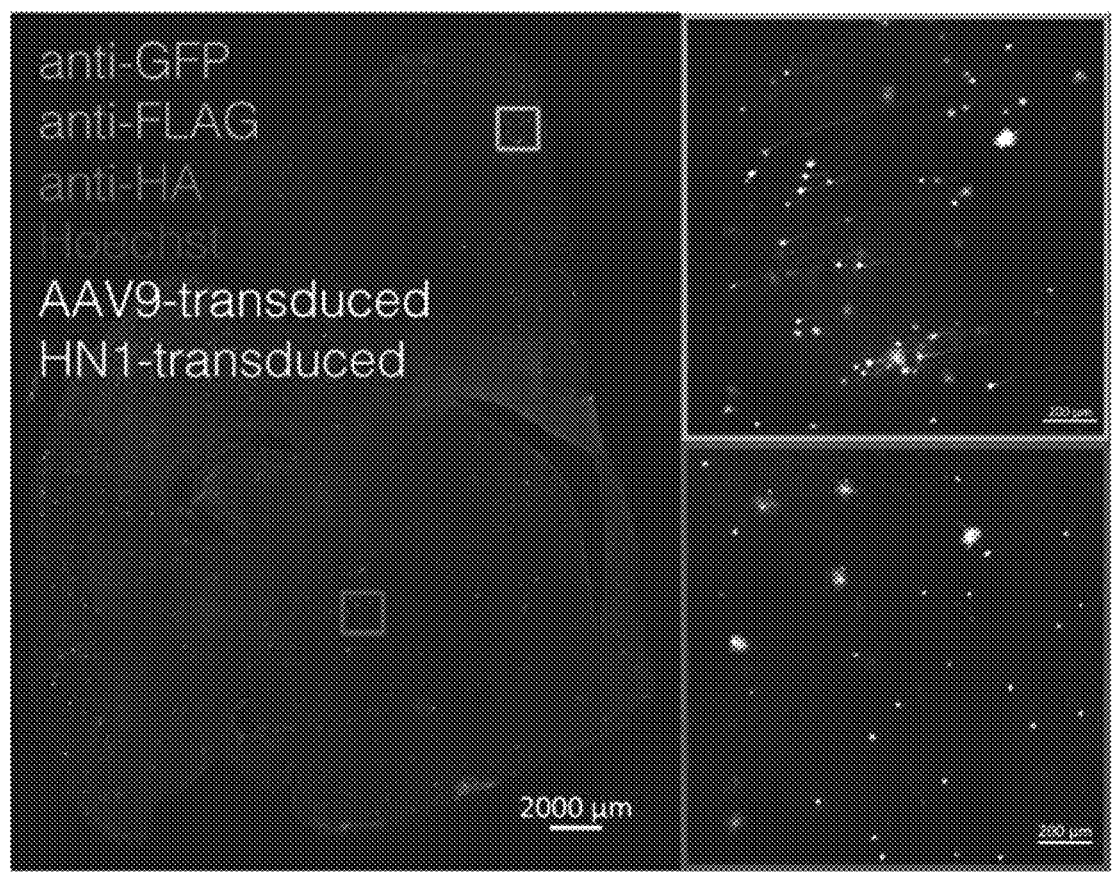

FIGS. 16A-16B: Validation of enhanced AAV9-N272A-HN1 transduction relative to AAV9 in rhesus macaques using epitope-tagged eGFP reporter vectors. (FIG. 16A) AAV-CAG-nIsGFP vectors used for this study. We produced 4 AAV vectors: AAV9-CAG-FLAGnIsGFP-BCLib, AAV9-CAG-HAnIsGFP-BCLib, AAV9-N272A-HN1-CAG-FLAGnIsGFP-BCLib and AAV9-N272A-HN1-CAG-HAnIsGFP-BCLib. The nIsGFP (eGFP with the nuclear localization signal derived from the SV40 large T antigen) was tagged with either the FLAG tag or the HA tag at the N-terminus. Each vector was a DNA/RNA-barcoded library containing an approximately 1 to 1 mixture of 9 different DNA/RNA-barcoded viral clones; however, this feature was not used in this study. The two vectors in the top half depicted in Panel A were mixed at a ratio of 1:1 to make AAV Library 1 (AAVLib1) and the two vectors in the bottom half were mixed at a ratio of 1:1 to make AAV Library 2 (AAVLib2). In this experimental scheme, AAVLib1 and AAVLib2 each contain AAV9 and AAV9-N272A-HN1 vectors expressing epitope-tagged nIsGFP at a ratio of 1:1, but the capsid-epitope relationship is inverted in order to avoid potential antibody bias in downstream analyses. (FIG. 16B) Representative tile-scanned brain section from one animal receiving AAVLib. Each AAV library was administered intravenously into a juvenile rhesus macaque at a dose of $3\times10^{13}$ vg/kg. Tissue was harvested 3-weeks post-injection, cut into 4mm slabs, fixed in 4% paraformaldehyde, and processed for immunohistochemical analysis with anti-GFP, anti-FLAG and anti-HA antibodies. eGFP expression indicates that a cell was transduced by either AAV9 or AAV9-N272A-HN1 or both. FLAG staining indicates that the AAV9 capsid mediated transduction, while HA staining indicates that AAV9-N272A-HN1 mediated transduction. Top-right inset, motor cortex; bottom-right inset, putamen. This experiment revealed that AAV9-N272A-HN1 transduced the brain cells better than AAV9 by several fold with strong neuronal tropism compared to AAV9. Therefore, as far as neuronal transduction is concerned, AAV9-N272A-HN1 mediates much higher neuronal transduction than AAV9.

FIGS. 17A-17D: Biodistribution of AAV9-N272A-HN1 to major peripheral organs following systemic delivery in mice and rhesus macaques. We used AAV DNA Barcode-Seq to determine relative abundance of AAV vector genome DNAs in each peripheral organ, delivered by each AAV capsid contained in the dsAAV-hSynI-GFP-BCLib library (Panels FIG. 17A, FIG. 17B and FIG. 17C). As explained earlier, the dsAAV-hSynI-GFP-BCLib library contained 26 AAV variants identified by TRADE in mice and in a non-human primate together with the controls, AAV9, AAV9-N272A and AAV-PHP.B. DNA was extracted from various tissues following administration of the dsAAV-hSynI-GFP-BCLib library (see Table 3) and subjected to AAV DNA Barcode-Seq analysis. We also used AAV RNA Barcode-Seq to determine relative transduction efficiency compared to AAV9 in each peripheral organ of rhesus macaques intravenously injected with the ssAAV-CAG-nIsGFP-BCLib library depicted in FIG. 16A (Panel D). (FIG. 17A) Biodistribution of AAV9, AAV9-N272A, AAV-PHP.B, and TRADE variants to the liver, relative to AAV9, in C57BL/6J mice, BALB/cJ mice and rhesus macaques. (FIG. 17B) Biodistribution of AAV9-N272A-HN1 to major peripheral organs besides the liver in C57BL/6J mice and BALB/cJ mice (n=3 mice/strain). (FIG. 17C) Biodistribution of AAV9-N272A-HN1 to major peripheral organs besides the liver in a rhesus macaque (n=1) based on dsAAV-hSynI-GFP-BC analysis. For this experiment, AAV DNA Barcode-Seq analysis was performed on the samples collected from one rhesus macaque injected with the dsAAV-hSynI-GFP-BCLib library shown in FIG. 14D. (FIG. 17D) Biodistribution of AAV9-N272A-HN1 to major peripheral organs besides the liver in rhesus (n=2) based on ssAAV-CAG-nIsGFP-BC analysis. For this experiment, AAV RNA Barcode-Seq analysis was performed on the samples collected from rhesus macaques injected with the ssAAV-GAG-nIsGFP-BCLib vectors shown in FIG. 16A. Error bars represent mean+/−SEM. AAV9-N272A-HN1 capsid transduced peripheral organs to a lesser degree compared to AAV9 capsid.

Figure 18A:
Figure 18B:
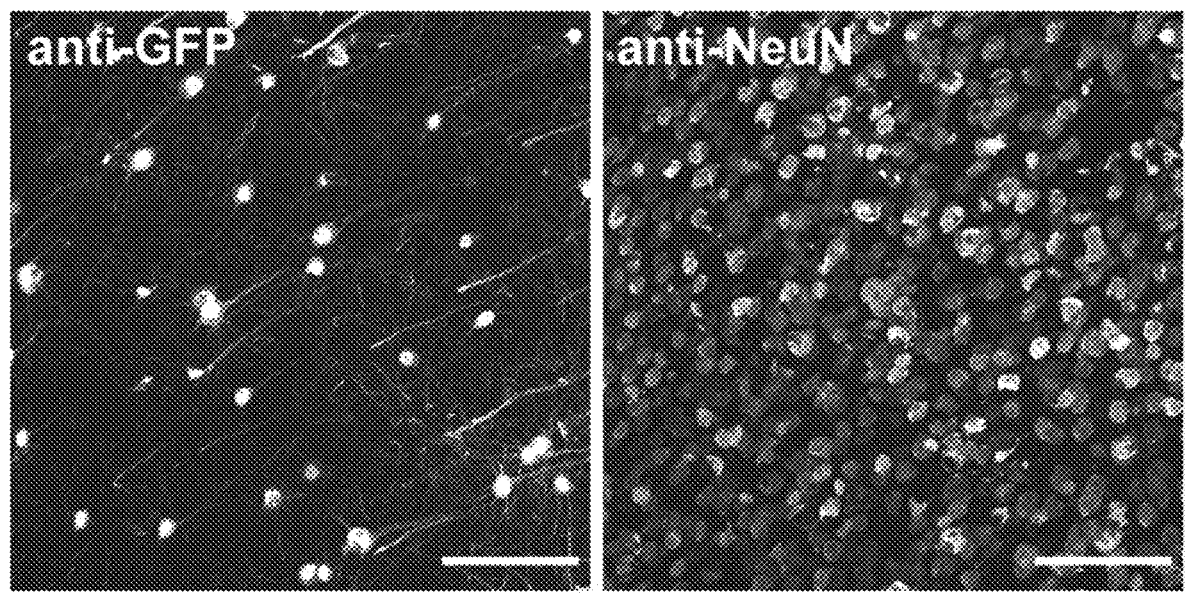
Figure 18C:
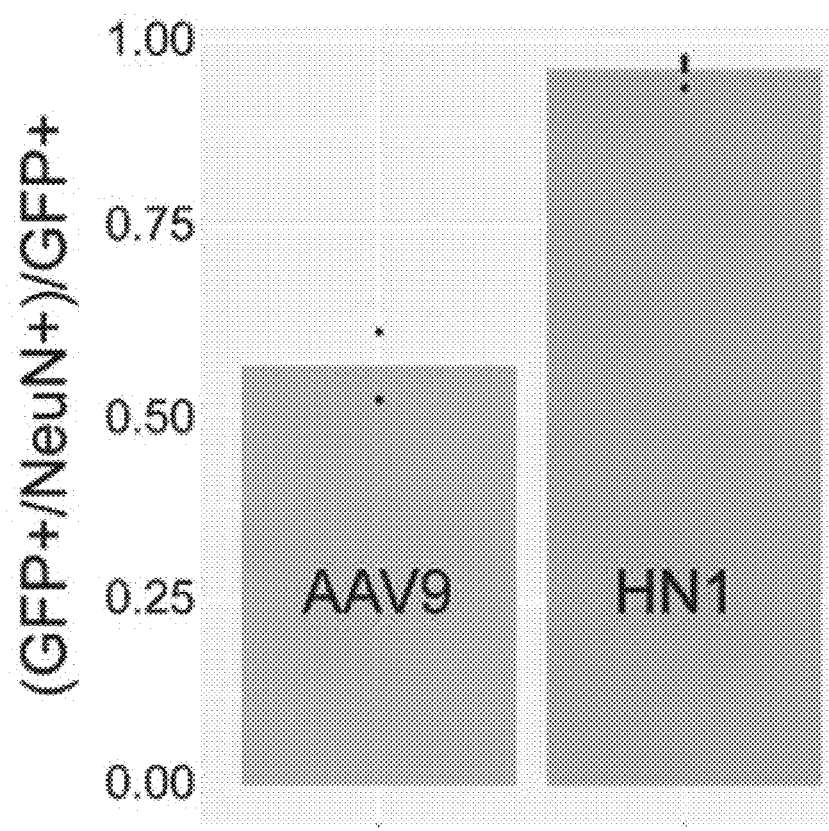

FIGS. 18A-18C: AAV9-N272A-HN1 is highly neurotropic following systemic administration in mice. AAV9 and AAV9-N272A-HN1 vectors expressing nIsGFP under the control of the strong, ubiquitous CAG promoter were injected intravenously into 8-week old male BALB/cJ mice at a dose of $3 \times 10^{11}$ vg/mouse. Tissues were harvested 12 days post-injection and analyzed by immunostaining with anti-GFP and anti-NeuN antibodies. (FIG. 18A) A map of the single-stranded (ss) AAV-CAG-nIsGFP vector genomes used in this study. (FIG. 18B) Representative image from mouse cerebral cortex transduced with AAV9-N272A-HN1-CAG-nIsGFP. The vast majority of cells transduced with AAV9-N272A-HN1-CAG-nIsGFP are also positive for the neuronal marker NeuN. Scale bar=100μm. (FIG. 18C) Neuronal specificity of AAV9 and AAV9-N272A-HN1 capsids. Quantification of neuronal specificity was determined by dividing the number of double-positive cells (eGFP+/NeuN+) by the total number of GFP+ cells. AAV9-N272A-HN1 is highly specific to neurons (96%) compared to AAV9 (56%).

DETAILED DESCRIPTION

In some embodiments, the present disclosure provides a TRADE system that allows directed evolution of the AAV capsid using antisense mRNA of the cap ORF expressed in a cell type-specific or ubiquitous manner. Such a system does not require Cre-transgenic animals. Therefore, it can be applied to cell type-specific AAV capsid evolution in large animals, including non-human primates, for which Cre-transgenic strains are not readily available. Any cell type-specific or tissue/organ-specific enhancers/promoters or ubiquitous enhancers/promoters can be readily applied to the system with no requirement of transgenesis. The cell type-specific selection is given at the mRNA level. In certain embodiments, multiple directed evolution schemes may be combined into one directed evolution scheme. For example, selection of neuron-specific AAV capsids, astrocyte-specific AAV capsids, oligodendrocyte-specific AAV capsids and microglia-specific AAV capsids based on cell type-specific transgene mRNA expression can be performed simultaneously in a single animal.

In some embodiments, the present disclosure provides a sense strand TRADE system that allows directed evolution of the AAV capsid using mRNA of the cap ORF expressed in a cell type-specific or ubiquitous manner that is capable of expressing AAV capsid proteins in target cells. The sense strand TRADE has the same advantages of those antisense strand TRADE presented with data here in that it does not require Cre-transgenic animals, cell type-specific selection is given at the mRNA level, and it is capable of combining multiple directed evolution schemes into one directed evolution round done in a single animal. However, the possible disadvantage is that immunogenic AAV capsid proteins may be unavoidably expressed persistently in target cells, which may result in undesired consequences in the capsid selection process.

In some embodiments, the present disclosure also provides novel AAV capsids. In certain embodiments, these novel AAV capsids can transduce brain neurons several times better than AAV9 in C57BL/6J mice following intravenous injection. In certain embodiments, the novel AAV capsids transduced up to 8 times better than AAV9 in C57BL/6J mice following intravenous injection. The neuronal transduction levels may be greatly enhanced compared to AAV9 although they may not attain the levels obtained with AAV PHP.B. In certain embodiments, the novel AAV capsids may transduce brain neurons more efficiently than AAV PHP.B.

In some embodiments, this disclosure provides novel AAV capsids that can transduce brain neurons several times better than AAV9 following intravenous injection in BALB/cJ mice. In certain embodiments, the novel AAV capsids can transduce brain neurons up to 7 times better than AAV9 following intravenous injection in BALB/cJ mice. The transduction levels are much higher than AAV PHP.B.

In some embodiments, this disclosure provides novel AAV capsids that can transduce brain neurons several times better than AAV9 in rhesus macaques following intravenous injection. In certain embodiments, the novel AAV capsids can transduce brain neurons up to 4 times better than AAV9 in rhesus macaques following intravenous injection. These transduction levels are better than AAV PHP.B.

In some embodiments, the disclosure provides AAV capsids that can transduce the pulmonary cells with neuronal cell marker expression several times better than AAV9. In certain embodiments, the AAV capsids can transduce such cells up to 17 times better than AAV9.

In some embodiments, the novel AAV capsids exhibit a liver-detargeting phenotype.

In some embodiments, the disclosure provides codon-modified AAV cap sequences that are not spliced when expressed in an antisense direction. We have observed that unmodified AAV cap ORFs are spliced when expressed in an antisense direction (e.g., AAV1, AAV3 and AAV9). In contrast, some of the codon-modified AAV cap ORFs described in this disclosure are not spliced. Based on the knowledge we have developed about the putative splice donor and acceptor sites, it has become possible to design such non-spliced versions of AAV cap ORFs. The use of such non-spliced cap ORFs may be used for directed evolution using the TRADE system when mutagenesis of the cap gene takes place over a wide region of the cap ORF.

The term "AAV vector" as used herein means any vector that comprises or derives from components of AAV and is suitable to infect mammalian cells, including human cells, of any of a number of tissue types, such as brain, heart, lung, skeletal muscle, liver, kidney, spleen, or pancreas, whether in vitro or in vivo. The term "AAV vector" may be used to refer to an AAV type viral particle (or virion) comprising at least a nucleic acid molecule encoding a protein of interest.

Additionally, the AAVs disclosed herein may be derived from various serotypes, including combinations of serotypes (e.g., "pseudotyped" AAV) or from various genomes (e.g., single-stranded or self-complementary). In particular embodiments, the AAV vectors disclosed herein may comprise desired proteins or protein variants. A "variant" as used herein refers to an amino acid sequence that is altered by one or more amino acids. The variant may have "conservative" changes, wherein a substituted amino acid has similar structural or chemical properties, e.g., replacement of leucine with isoleucine. Alternatively, a variant may have "nonconservative" changes, e.g., replacement of a glycine with a tryptophan. Analogous minor variations may also include amino acid deletions or insertions, or both.

Nucleotide sequences, such as polynucleotides, encoding proteins of the present disclosure are provided herein. The nucleotides of the present disclosure can be composed of either RNA or DNA. The disclosure also encompasses those polynucleotides that are complementary in sequence to the polynucleotides disclosed herein.

Because of the degeneracy of the genetic code, a variety of different polynucleotide sequences can encode the proteins of the present disclosure. In addition, it is well within the skill of a person trained in the art to create alternative polynucleotide sequences encoding the same, or essentially the same, proteins disclosed herein. These variant or alternative polynucleotide sequences are within the scope of the current disclosure. As used herein, references to "essentially the same sequence" refers to one or more sequences that encode amino acid substitutions, deletions, additions, or insertions that do not eliminate the detectability of the polypeptide encoded by the polynucleotides of the present disclosure.

The current disclosure also includes variants of the polynucleotides and polypeptides disclosed herein. Variant sequences include those sequences wherein one or more peptides or nucleotides of the sequence have been substituted, deleted, and/or inserted.

Polynucleotide and polypeptide sequences of the current disclosure can also be defined in terms of particular identity and/or similarity with certain polynucleotides and polypeptides described herein. The sequence identity will typically be greater than 60%, preferably greater than 75%, more preferably greater than 80%, even more preferably greater than 90%, and can be greater than 95%. The identity and/or similarity of a sequence can be 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical as compared to a sequence disclosed herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990).

BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used.

Methods of producing AAV vectors as disclosed herein are well known in the art, including methods, for example, of using packaging cells, auxiliary viruses or plasmids, and/or baculovirus systems. See, e.g., Samulski et al., *J. Virology* 63, 3822 (1989); Xiao et al., *J. Virology* 72, 2224 (1998); Inoue et al., *J. Virology* 72, 7024 (1998); WO1998/022607; and WO2005/072364.

Methods of producing pseudotyped AAV vectors are also known (see, e.g., WO00/28004), as well as various modifications or formulations of AAV vectors, to reduce their immunogenicity upon in vivo administration (see, e.g., WO01/23001; WO00/73316; WO04/112727; WO05/005610; and WO99/06562). In some embodiments, AAV vectors may be prepared or derived from various serotypes of AAVs which may be mixed together or mixed with other types of viruses to produce chimeric (e.g., pseudotyped) AAV viruses.

In particular embodiments, the AAV vector may be a human serotype AAV vector. In such embodiments, a human AAV may be derived from any known serotype, e.g., from any one of serotypes 1-11, for instance from AAV1, AAV2, AAV4, AAV6, or AAV9.

The AAV vectors disclosed herein may include a nucleic acid encoding a protein of interest. In various embodiments, the nucleic acid also may include one or more regulatory sequences allowing expression and, in some embodiments, secretion of the protein of interest, such as e.g., a promoter, enhancer, polyadenylation signal, an internal ribosome entry site ("IRES"), a sequence encoding a protein transduction domain ("PTD"), a 2A peptide, and the like. Thus, in some embodiments, the nucleic acid may comprise a promoter region operably linked to the coding sequence to cause or improve expression of the protein of interest in infected cells. Such a promoter may be ubiquitous, cell- or tissue-specific, strong, weak, regulated, chimeric, etc., for example, to allow efficient and stable production of the protein in the infected tissue. The promoter may be homologous to the encoded protein, or heterologous, although generally promoters of use in the disclosed methods are functional in human cells. Examples of regulated promoters include, without limitation, Tet on/off element-containing promoters, rapamycin-inducible promoters, tamoxifen-inducible promoters, and metallothionein promoters. Other promoters that may be used include promoters that are tissue specific for tissues such as kidney, spleen, and pancreas. Examples of ubiquitous promoters include viral promoters, particularly the CMV promoter, the RSV promoter, the SV40 promoter, etc., and cellular promoters such as the phosphoglycerate kinase (PGK) promoter and the β-actin promoter.

In some embodiments of the AAV vectors disclosed herein, one or more feedback elements may be used to dampen over-expression of the protein of interest. For example, some embodiments of the AAV vectors may include one or more siRNA sequences that would target the exogenous transcript. In other embodiments, the AAV vector may include one or more additional promoters that may be recognized by inhibitory transcription factors. In various embodiments, the AAV vectors disclosed herein may comprise a construct that may create a homoeostatic feedback loop that may maintain expression levels of the protein of interest at a physiological level.

In some embodiments of the AAV vectors disclosed herein, genome editing machinery may be used to genetically modify cellular genome DNA or mRNA transcripts at a site-specific manner. Komor et al., Cell 168, 20-36 (2017); and Katrekar et al., Nature Methods 16:239-242, 2019. For example, some embodiments of the AAV vectors may include a CRISPR-associated enzyme such as Cas9, a DNA base editor, an RNA editase and/or guide RNA (gRNA) to modify nucleic acid in cells in a site-specific manner. In addition, AAV vectors may contain a homology repair template (HDR) for genome editing.

In various embodiments, the AAV vectors disclosed herein can comprise a nucleic acid that may include a leader sequence allowing secretion of the encoded protein. In some embodiments, fusion of the transgene of interest with a sequence encoding a secretion signal peptide (usually located at the N-terminal of secreted polypeptides) may allow the production of the therapeutic protein in a form that can be secreted from the transduced cell. Examples of such signal peptides include the albumin, the β-glucuronidase, the alkaline protease or the fibronectin secretory signal peptides.

As described herein, effective and long-term expression of therapeutic proteins of interest in brain, heart, lung, skeletal muscle, kidney, spleen, or pancreas can be achieved with non-invasive techniques, through peripheral administration of certain AAV vectors, such as a non-AAV9 vector with AAV9 sequences. Such peripheral administration may include any administration route that does not necessitate direct injection into brain, heart, lung, skeletal muscle, kidney, spleen, or pancreas. More particularly, peripheral administration may include systemic injections, such as intramuscular, intravascular (such as intravenous,) intraperitoneal, intra-arterial, or subcutaneous injections. In some embodiments, peripheral administration also may include oral administration (see, e.g., WO96/40954), delivery using implants, (see, e.g., WO01/91803), or administration by instillation through the respiratory system, e.g., using sprays, aerosols or any other appropriate formulations.

In various embodiments, the desired doses of the AAV vectors may be adapted by the skilled artisan, e.g., depending on the disease condition, the subject, the treatment schedule, etc. In some embodiments, from $10^5$ to $10^{12}$ viral genomes are administered per dose, for example, from $10^6$ to $10^{11}$, from $10^7$ to $10^{11}$, or from $10^8$ to $10^{11}$. In other embodiments, exemplary doses for achieving therapeutic effects may include virus titers of at least about $10^5$, $10^6$, $10^7$, $10^8$, $10^9$, $10^{10}$ or $10^{11}$ viral genomes or more. Virus titer may also be expressed in terms of transducing units, which may be readily calculated by those of skill in the art.

In various embodiments, the AAV vectors disclosed herein may be administered in any suitable form, for instance, either as a liquid solution or suspension, as a solid form suitable for solution or suspension in liquid prior to injection, as a gel or as an emulsion. The vectors may be formulated with any appropriate and pharmaceutically acceptable excipient, carrier, adjuvant, diluent, etc. For instance, for injection, a suitable carrier or diluent may be an isotonic solution, a buffer, sterile and pyrogen-free water, or, for instance, a sterile and pyrogen-free phosphate-buffered saline solution. For inhalation, the carrier may be in particulate form.

The vectors may be administered in a "therapeutically-effective" amount, e.g., an amount that is sufficient to alleviate (e.g., decrease, reduce) at least one of the symptoms associated with a disease state, or to provide improvement in the condition of the subject. In some embodiments, repeated administrations may be performed, for instance using the same or a different peripheral administration route and/or the same vector or a distinct vector.

Enumerated Embodiments

Embodiment 1: A nucleic acid comprising: a Parvoviridae genome flanked by ITR sequences, wherein the Parvoviridae genome comprises a Parvoviridae intron, a Parvoviridae cap gene, and a first polyadenylation signal in a first orientation; a first promoter in the first orientation that drives expression of the Parvoviridae cap gene in the presence of adenoviral helper functions; and a second promoter and a second polyadenylation signal in a second orientation that is antisense with respect to the first orientation, and wherein the second polyadenylation signal is located at a position that causes termination of antisense mRNA transcription of the Parvoviridae cap gene.

Embodiment 2: The nucleic acid of embodiment 1, wherein the second promoter is a cell type-specific promoter.

Embodiment 3: The nucleic acid of embodiment 1, wherein the second promoter is a ubiquitous promoter.

Embodiment 4: The nucleic acid of any of embodiments 1-3, wherein the Parvoviridae genome is an AAV genome comprising an AAV intron and an AAV cap gene Embodiment 5: The nucleic acid of embodiment 4, wherein the AAV cap gene is a wild-type AAV cap gene.

Embodiment 6: The nucleic acid of embodiment 5, wherein the AAV cap gene sequence is the AAV1, AAV2, AAV3, AAV4, AAV5, AAV6, AAV7, AAV8, AAV9, AAV10, AAV11, AAV12, AAV13 or other natural AAV isolate cap gene sequence.

Embodiment 7: The nucleic acid of embodiment 4, wherein the AAV cap gene is an engineered AAV cap gene.

Embodiment 8: The nucleic acid of embodiment 4, wherein the AAV cap gene is one of a library of diverse AAV cap genes.

Embodiment 9: A nucleic acid library comprising a plurality of nucleic acids of embodiment 4, wherein the nucleic acids comprise a plurality of unique AAV cap gene sequences.

Embodiment 10: The nucleic acid library of embodiment 9, wherein the nucleic acid library comprises greater than about $10^2$, $10^3$, $10^4$, $10^5$, $10^6$, $10^7$ or $10^8$ unique AAV cap gene sequences.

Embodiment 11: The nucleic acid of any of embodiments 1-8, further comprising a gene of interest in the second orientation.

Embodiment 12: The nucleic acid of any of embodiments 4-8 or 11, wherein the second polyadenylation signal is located within the AAV intron.

Embodiment 13: The nucleic acid of any of embodiments 4-8 or 11, wherein the second polyadenylation signal is located such that the cap gene is correctly translated into a full-length capsid protein in the first orientation and the cap gene is correctly transcribed into anti-sense mRNA that contains a full-length AAV cap gene coding sequence.

Embodiment 14: A method for identifying an AAV vector with a cap gene sequence that has increased ability to transduce cells from a tissue of interest when compared to at least one other AAV vector with a different cap gene sequence, the method comprising: Preparing a first-round AAV TRADE vector library by introducing the nucleic acid library of embodiment 9 or 10 into an AAV packaging cell line and recovering the first round AAV TRADE vector library from the packaging cell line; Injecting one or more animals with the first-round AAV TRADE vector library; Recovering cap gene sequences of AAV vectors that are enriched in cells of the tissue of interest in the animals; Preparing a second-round AAV TRADE nucleic acid library comprising recovered cap gene sequences of the enriched AAV vectors and introducing this library into an AAV packaging cell line and recovering the second round AAV TRADE vector library from the packaging cell line; Performing a second round of enrichment by injecting one or more animals with the second-round AAV TRADE vector library and recovering cap gene sequence that are enriched in cells of the tissue of interest in the animals; and Identifying enriched AAV cap gene sequences after the first-round enrichment, after the second-round enrichment, and after any subsequent rounds of enrichment.

Embodiment 15: A method for producing an AAV TRADE vector or an AAV TRADE vector library comprising: Introducing the nucleic acid of any of embodiments 4-8 or 11-13, or the nucleic acid library of embodiment 9 or 10, into an AAV packaging cell line and recovering the AAV TRADE vector or AAV TRADE vector library from the packaging cell line.

Embodiment 16: A method for determining a sequence of a novel cap gene of an AAV vector that has increased ability to transduce cells from a tissue of interest comprising: Identifying the AAV vector according to the method of embodiment 14; Recovering antisense mRNA comprising the cap gene sequence; and determining the novel cap gene sequence.

Embodiment 17: The method of embodiment 16, wherein the antisense mRNA is recovered using RT-PCR.

Embodiment 18: The method of either embodiment 16 or 17, further comprising the step of determining the cap gene sequence Embodiment 19: An AAV vector comprising the nucleic acid of any of embodiments 4-8 or 11-13.

Embodiment 20: A nucleic acid comprising: a Parvoviridae genome flanked by ITR sequences, wherein the Parvoviridae genome comprises a Parvoviridae intron, a Parvoviridae cap gene, and a first polyadenylation signal in a first orientation; a first promoter in the first orientation that drives expression of the Parvoviridae cap gene in the presence of adenoviral helper functions; and a second promoter in the first orientation that drives expression of the Parvoviridae cap gene in the absence of adenoviral helper functions.

Embodiment 21: The nucleic acid of embodiment 20, wherein the second promoter is a cell type-specific promoter.

Embodiment 22: The nucleic acid of embodiment 20, wherein the second promoter is a ubiquitous promoter.

Embodiment 23: The nucleic acid of any of embodiments 20-22, wherein the Parvoviridae cap gene is a wild-type AAV cap gene.

Embodiment 24: The nucleic acid of embodiment 23, wherein the AAV cap gene sequences is the AAV1, AAV2, AAV3, AAV4, AAV5, AAV6, AAV7, AAV8, AAV9, AAV10, AAV11, AAV12, AAV13 or other natural AAV isolate cap gene sequence.

Embodiment 25: The nucleic acid of any of embodiments 20-22, wherein the Parvoviridae cap gene is an engineered AAV cap gene.

Embodiment 26: The nucleic acid of any of embodiments 20-25, wherein the Parvoviridae cap gene is one of a library of diverse AAV cap genes.

Embodiment 27: A nucleic acid library comprising a plurality of nucleic acids of embodiment 20, wherein the nucleic acids comprise a plurality of unique Parvoviridae cap gene sequences.

Embodiment 28: The nucleic acid library of embodiment 27, wherein the nucleic acid library comprises greater than about $10^2$, $10^3$, $10^4$, $10^5$, $10^6$, $10^7$ or $10^8$ unique AAV cap gene sequences.

Embodiment 29: The nucleic acid of any of embodiments 20-26, further comprising a gene of interest.

Embodiment 30: A method for identifying an AAV vector with a cap gene sequence that has increased ability to transduce cells from a tissue of interest when compared to at least one other AAV vector with a different cap gene sequence, the method comprising: Preparing a first-round AAV TRADE vector library by introducing the nucleic acid library of embodiment 27 or 28 into an AAV packaging cell line and recovering the first round AAV TRADE vector library from the packaging cell line; Injecting one or more animals with the first-round AAV TRADE vector library; Recovering cap gene sequences of AAV vectors that are enriched in cells of the tissue of interest in the animals; preparing a second-round AAV TRADE nucleic acid library comprising recovered cap gene sequences of the enriched AAV vectors and introducing this library into an AAV packaging cell line and recovering the second round AAV TRADE vector library from the packaging cell line; Performing a second round of enrichment by injecting one or more animals with the second-round AAV TRADE vector library and recovering cap gene sequence that are enriched in cells of the tissue of interest in the animals; and Identifying enriched AAV cap gene sequences after the first-round enrichment, after the second-round enrichment, and after any subsequent rounds of enrichment.

Embodiment 31: A method for producing an AAV TRADE vector or an AAV TRADE vector library comprising: Introducing the nucleic acid of any of embodiments 23-26 or 29, or the nucleic acid library of embodiment 27 or 28, into an AAV packaging cell line and recovering the AAV TRADE vector or AAV TRADE vector library from the packaging cell line.

Embodiment 32: A method for determining a sequence of a novel cap gene of an AAV vector that has increased ability to transduce cells from a tissue of interest comprising: Identifying the AAV vector according to the method of embodiment 30; Recovering sense mRNA comprising the cap gene sequence; and Determining the novel cap gene sequence.

Embodiment 33: The method of embodiment 32, wherein the sense mRNA is recovered using RT-PCR.

Embodiment 34: The method of either embodiment 32 or 33, further comprising the step of determining the cap gene sequence.

Embodiment 35: An AAV vector comprising the nucleic acid of any of embodiments 23-26 or 29.

Embodiment 36: The nucleic acid of any of embodiments 1-8 or 11-13, further comprising at least one mRNA splicing suppressing mutation in the second orientation.

Embodiment 37: The nucleic acid of embodiment 36, wherein the at least one mRNA splicing suppressing mutation comprises an alteration of one or more nucleotides located within ten nucleotides of the splice donor and/or splice acceptor site.

Embodiment 38: The nucleic acid of embodiment 36 or 37, wherein the alteration does not change the amino acid sequence encoded by the AAV cap gene.

Embodiment 39: An AAV cap ORF sequence comprising one or more following mutations in the exon-intron junctions at splicing donor sites:

```
                                         (SEQ ID NO: 199)
AAV1 VP1 cap ORF 1009-CTTAC(junction)CAGCA-1018*

(SEQ ID NO: 199)
AAV3 VP1 cap ORF 1006-CTTAC(junction)CAGCA-1015*

(SEQ ID NO: 200)
AAV1 VP1 cap ORF 1228-TTTAC(junction)CTTCA-1237

(SEQ ID NO: 201)
AAV3 VP1 cap ORF 1237-TATAC(junction)CTTCG-1246

(SEQ ID NO: 202)
AAV1 VP1 cap ORF 1331-ATTAC(junction)CTGAA-1340

(SEQ ID NO: 203)
AAV1 VP1 cap ORF 1434-GCTAC(junction)CTGGA-1443

(SEQ ID NO: 204)
AAV1 VP1 cap ORF 1502-TTTAC(junction)CTGGA-1510

(SEQ ID NO: 205)
AAV1 VP1 cap ORF 1803-ATTAC(junction)CTGGC-1812

(SEQ ID NO: 206)
AAV3 VP1 cap ORF 1803-CTTAC(junction)CTGGC-1812

(SEQ ID NO: 207)
AAV1 VP1 cap ORF 1835-TGTAC(junction)CTGCA-1844

(SEQ ID NO: 208)
AAV1 VP1 cap ORF 2189-GTTAC(junction)CTTAC-2198

(SEQ ID NO: 209)
AAV9 VP1 cap ORF 2189-GATAC(junction)CTGAC-2198

(SEQ ID NO: 210)
AAV1 VP1 cap ORF 2194-CTTAC(junction)CCGTC-2203

(SEQ ID NO: 211)
AAV3 VP1 cap ORF 2194-CTCAC(junction)ACGAA-2203.
(*Although the nucleotide numbers are different,
they are corresponding nucleotides of the AAV
cap ORFs in sequence alignment.)
```

Embodiment 40: An AAV cap ORF sequence comprising one or more following mutations in the exon-intron junctions at splicing donor sites:

```
                                         (SEQ ID NO: 212)
AAV1 VP1 cap ORF 305-AGCGT(junction)CTGCA-314

(SEQ ID NO: 213)
AAV1 VP1 cap ORF 414-GGCTC(junction)CTGGA-423

(SEQ ID NO: 213)
AAV3 VP1 cap ORF 414-GGCTC(junction)CTGGA-423

(SEQ ID NO: 214)
AAV1 VP1 cap ORF 495-GCCCG(junction)CTAAA-504

(SEQ ID NO: 214)
AAV9 VP1 cap ORF 495-GCCCG(junction)CTAAA-504

(SEQ ID NO: 215)
AAV3 VP1 cap ORF 1133-TCACC(junction)CTGAA-1142

(SEQ ID NO: 216)
AAV1 VP1 cap ORF 1181-ACTGC(junction)CTGGA-1190

(SEQ ID NO: 202)
AAV1 VP1 cap ORF 1331-ATTAC(junction)CTGAA-1340**

(SEQ ID NO: 217)
AAV3 VP1 cap ORF 1328-ACTAC(junction)CTGAA-1337**

(SEQ ID NO: 218)
AAV1 VP1 cap ORF 1464-CGTTT(junction)CTAAA-1473

(SEQ ID NO: 219)
AAV1 VP1 cap ORF 1653-AAACA(junction)CTGCA-1662

(SEQ ID NO: 220)
AAV1 VP1 cap ORF 2054-GGGAG(junction)CTGCA-2063

(SEQ ID NO: 463)
AAV3 VP1 cap ORF 2054-GGGAG(junction)CTACA-2063
(**Although the nucleotide numbers are different,
they are corresponding nucleotides of the AAV
cap ORFs in sequence alignment.)
```

Embodiment 41: An AAV cap ORF sequence comprising one or more following mutations in the exon-intron junctions at splicing donor or splicing acceptor sites:

```
Splice donors
                                         (SEQ ID NO: 199)
AAV1 VP1 cap ORF 1009-CTTAC(junction)CAGCA-1018*

(SEQ ID NO: 199)
AAV3 VP1 cap ORF 1006-CTTAC(junction)CAGCA-1015*

(SEQ ID NO: 200)
AAV1 VP1 cap ORF 1228-TTTAC(junction)CTTCA-1237

(SEQ ID NO: 201)
AAV3 VP1 cap ORF 1237-TATAC(junction)CTTCG-1246

(SEQ ID NO: 202)
AAV1 VP1 cap ORF 1331-ATTAC(junction)CTGAA-1340

(SEQ ID NO: 203)
AAV1 VP1 cap ORF 1434-GCTAC(junction)CTGGA-1443

(SEQ ID NO: 204)
AAV1 VP1 cap ORF 1502-TTTAC(junction)CTGGA-1510

(SEQ ID NO: 205)
AAV1 VP1 cap ORF 1803-ATTAC(junction)CTGGC-1812

(SEQ ID NO: 206)
AAV3 VP1 cap ORF 1803-CTTAC(junction)CTGGC-1812

(SEQ ID NO: 207)
AAV1 VP1 cap ORF 1835-TGTAC(junction)CTGCA-1844

(SEQ ID NO: 208)
AAV1 VP1 cap ORF 2189-GTTAC(junction)CTTAC-2198

(SEQ ID NO: 209)
AAV9 VP1 cap ORF 2189-GATAC(junction)CTGAC-2198

(SEQ ID NO: 210)
AAV1 VP1 cap ORF 2194-CTTAC(junction)CCGTC-2203

(SEQ ID NO: 211)
AAV3 VP1 cap ORF 2194-CTCAC(junction)ACGAA-2203

Splice acceptor
                                         (SEQ ID NO: 212)
AAV1 VP1 cap ORF 305-AGCGT(junction)CTGCA-314

(SEQ ID NO: 213)
AAV1 VP1 cap ORF 414-GGCTC(junction)CTGGA-423

(SEQ ID NO: 213)
AAV3 VP1 cap ORF 414-GGCTC(junction)CTGGA-423

(SEQ ID NO: 214)
AAV1 VP1 cap ORF 495-GCCCG(junction)CTAAA-504
```

-continued

AAV9 VP1 cap ORF 495-GCCCG(junction)CTAAA-504 (SEQ ID NO: 214)

AAV3 VP1 cap ORF 1133-TCACC(junction)CTGAA-1142 (SEQ ID NO: 215)

AAV1 VP1 cap ORF 1181-ACTGC(junction)CTGGA-1190 (SEQ ID NO: 216)

AAV1 VP1 cap ORF 1331-ATTAC(junction)CTGAA-1340** (SEQ ID NO: 202)

AAV3 VP1 cap ORF 1328-ACTAC(junction)CTGAA-1337** (SEQ ID NO: 217)

AAV1 VP1 cap ORF 1464-CGTTT(junction)CTAAA-1473 (SEQ ID NO: 218)

AAV1 VP1 cap ORF 1653-AAACA(junction)CTGCA-1662 (SEQ ID NO: 219)

AAV1 VP1 cap ORF 2054-GGGAG(junction)CTGCA-2063 (SEQ ID NO: 220)

AAV3 VP1 cap ORF 2054-GGGAG(junction)CTACA-2063. (SEQ ID NO: 463)

EXAMPLES

The following examples are for illustration only. In light of this disclosure, those of skill in the art will recognize that variations of these examples and other embodiments of the disclosed subject matter are enabled without undue experimentation.

Figure 2A:
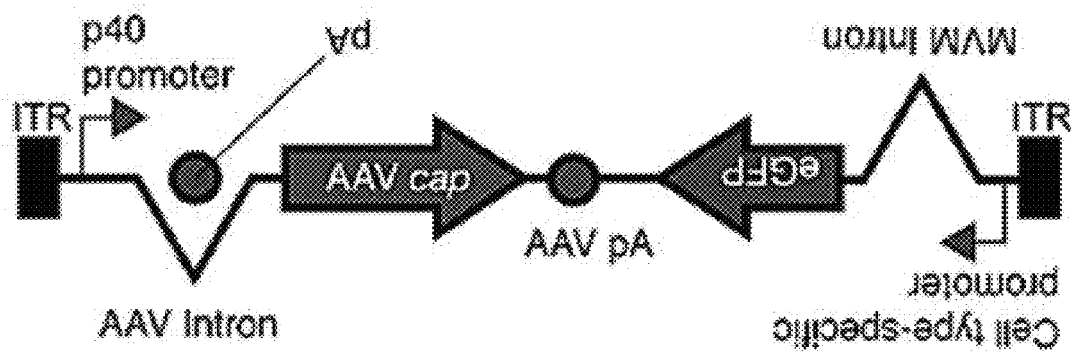
FIGS. 2A-2B: Principle of TRADE.
Figure 2B:
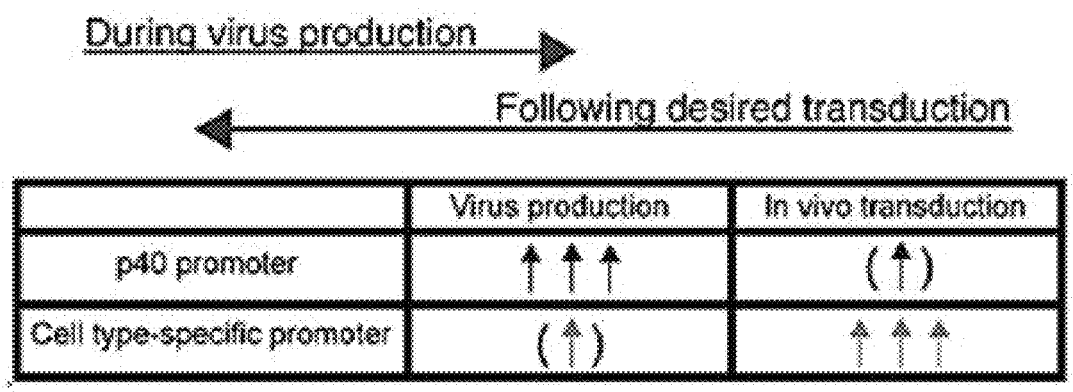

We applied the TRADE system in both C57BL/6J mice and a rhesus macaque in order to identify novel AAV capsids that efficiently transduce brain neurons following systemic delivery. The TRADE system utilizes a plasmid construct containing an overlapping bicistronic AAV genome flanked by ITR sequences (FIG. 2A). In the sense direction, the AAV2 p40 promoter drives expression of the AAV cap gene to facilitate efficient production of viral particles (FIG. 2B). In the antisense direction, a cell type-specific enhancer-promoter (e.g. the human synapsin I (hSynI) enhancer-promoter) drives expression of transcripts encoding GFP and the antisense cap sequence (FIG. 2B), terminating at a polyadenylation signal (poly A) embedded in the intron present in the AAV2 genome. Utilizing the TRADE construct as a cloning backbone, we generated an AAV library based on the liver-detargeted AAV9-N272A (PCT/US2017/068050) cap gene platform that contained random 8-mer peptides with glycine-serine linkers (5'-GGGS; 3'-GGGGS) substituted at the position Q588 in the AAV9 capsid. In vivo selection in a specific cell type (e.g. neurons) was performed by recovering capsid sequences as antisense cap ORF mRNA from brain tissue by RT-PCR. This method ensures that recovered sequences are only derived from AAV variants that are capable of mediating RNA expression in infected cells of our interest. When the hSynI enhancer-promoter is used, only sequences of AAV capsids that are capable of transducing neurons can be retrieved, thus enabling neuron-specific selection of AAV capsids.

Figure 3A:
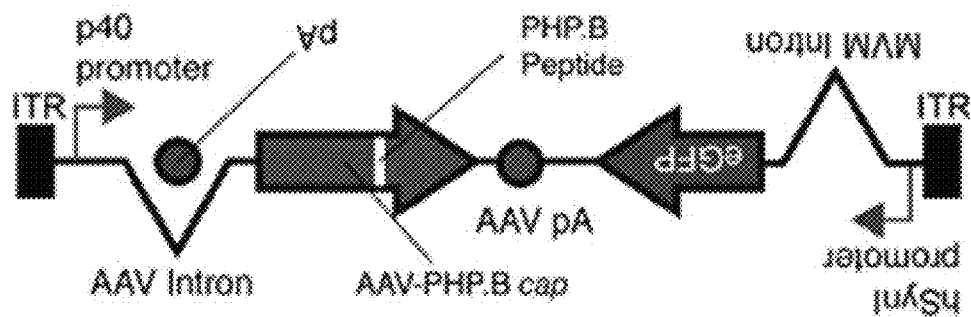
FIGS. 3A-3G: Validation of the TRADE system targeting brain neurons.
Figure 3B:
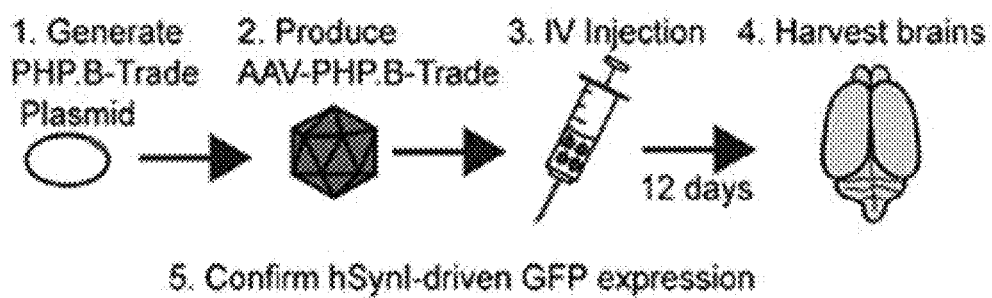
Figure 3C:
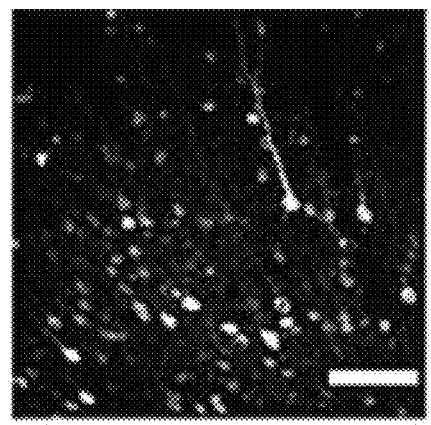
Figure 3D:
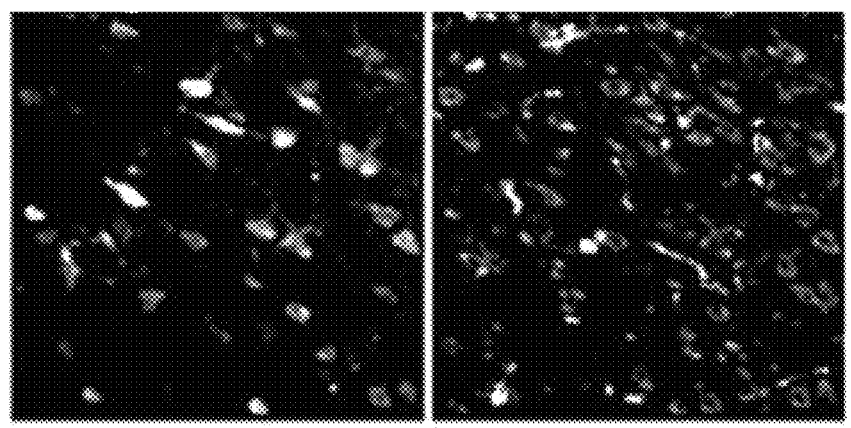
Figure 3E:
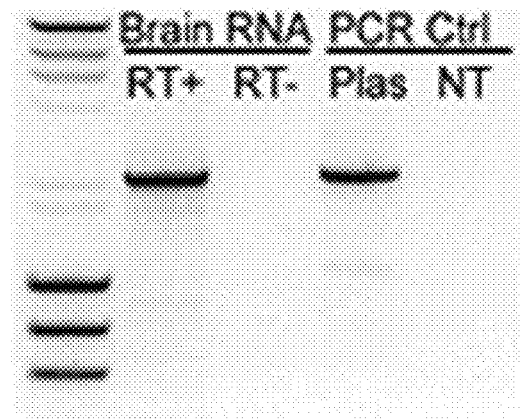
Figure 3F:
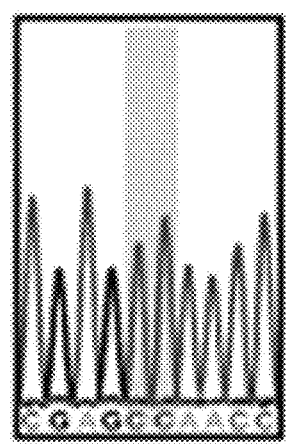
Figure 3G:
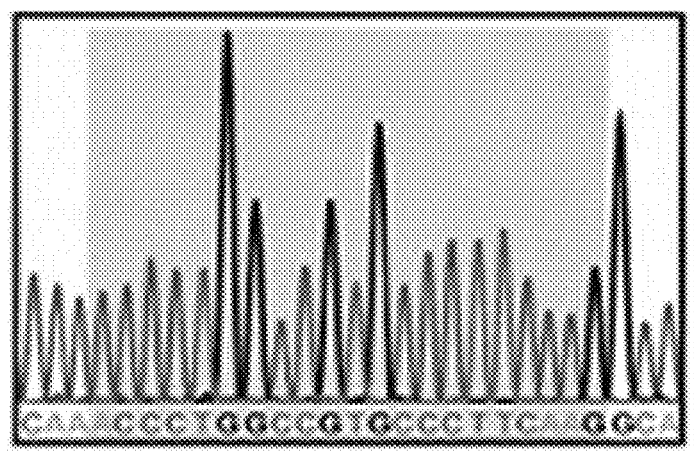

We first tested the ability of the TRADE system to recover the sequence of the AAV cap gene from cell type-specific antisense mRNA using an AAV-PHP.B-hSynI-GFP-TRADE vector (FIGS. 3A-3G). A hSynI enhancer-promoter-driven GFP expression cassette was incorporated in the AAV-PHP.B capsid gene-containing AAV vector genome in the TRADE configuration (FIG. 3A). This vector genome was packaged into the AAV-PHP.B capsid, and the resulting AAV vector was injected intravenously into two 8-week-old male C57BL/6J mice (FIG. 3B). Twelve days after injection, brain tissue was harvested. Tissue fixed with 4% paraformaldehyde was analyzed by immunofluorescence microscopy. Unfixed tissue was utilized for RNA extraction and RT-PCR analysis. We confirmed that eGFP was expressed only in neurons (FIG. 3C and FIG. 3D), indicating that the antisense mRNA transcribed from the cap gene is expressed in a cell type-specific manner. We recovered antisense mRNA of the cap gene efficiently by RT-PCR (FIG. 3E). Sanger sequencing of a splice junction unique to the antisense mRNA confirmed that RT-PCR products were indeed derived from the hSynI enhancer-promoter-driven antisense mRNA (FIG. 3F). In addition, Sanger sequencing confirmed the sequence of the PHP.B peptide insertion (FIG. 3F). Together, these observations established the ability of the TRADE system to successfully recover the AAV cap sequence from the hSynI enhancer-promoter-driven antisense mRNA expressed in AAV vector-transduced brain neurons.

Figure 14A:
Figure 14B:
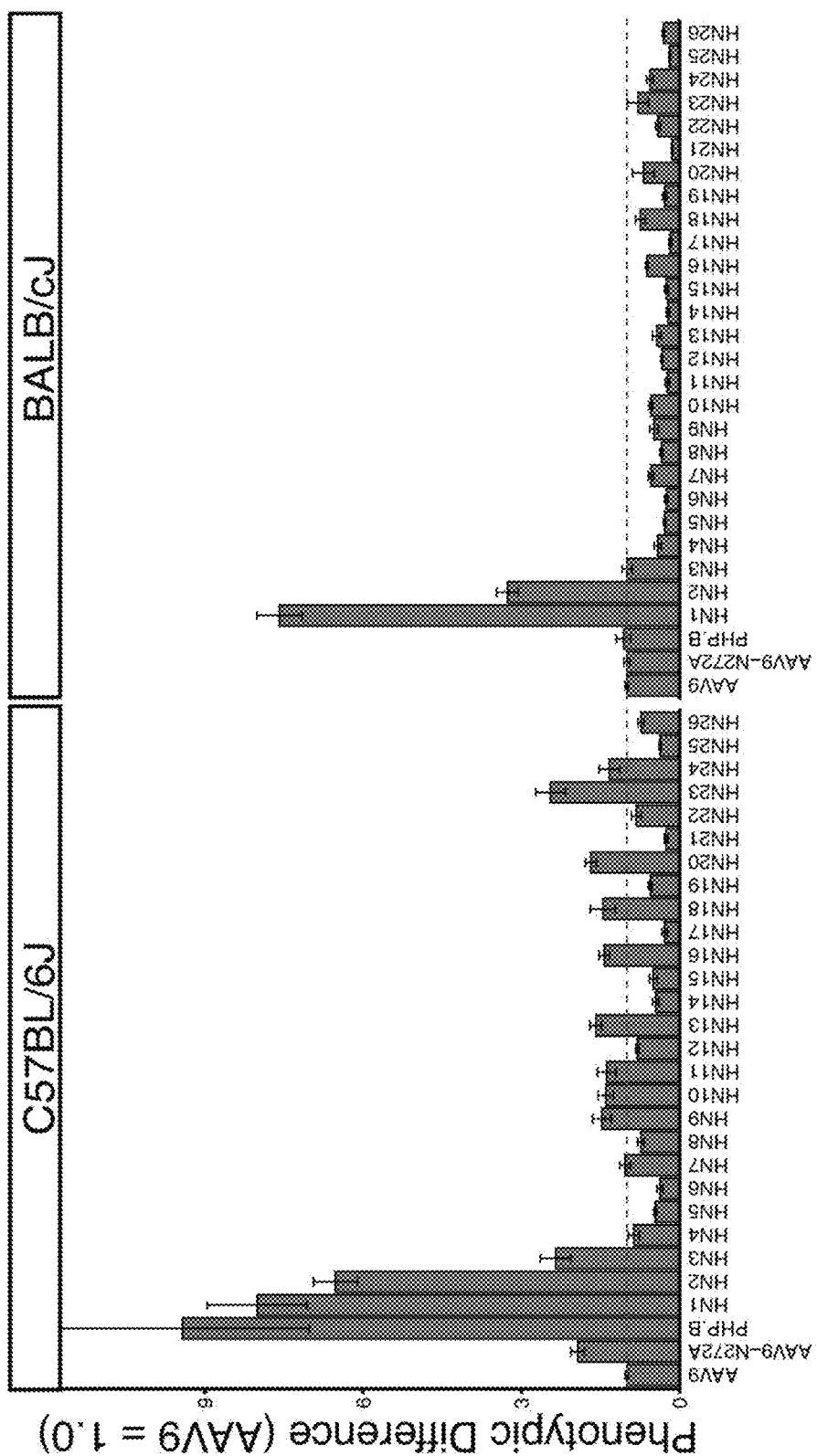
Figure 14C:
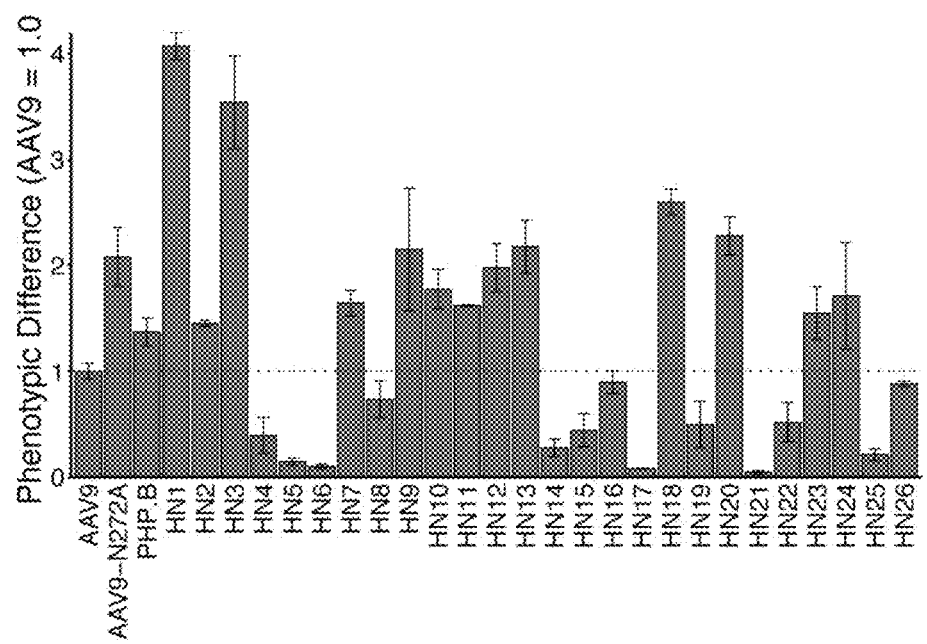
Figure 14D:
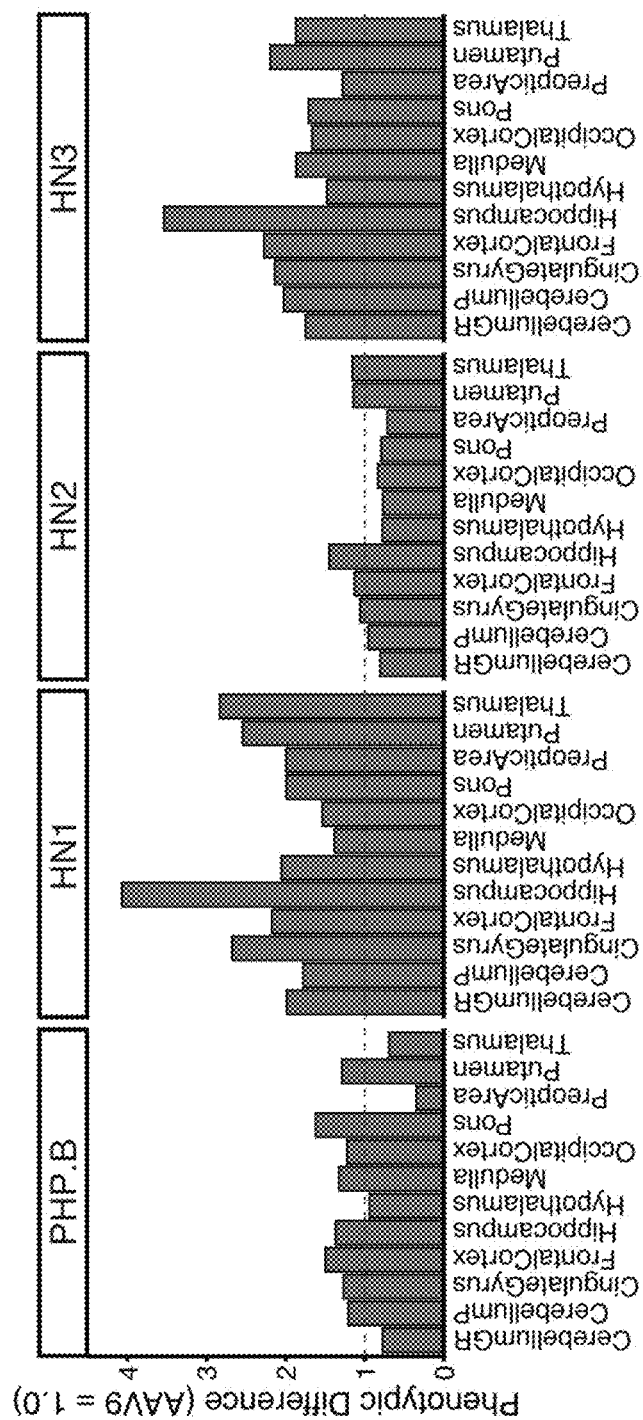
Figure 17A:
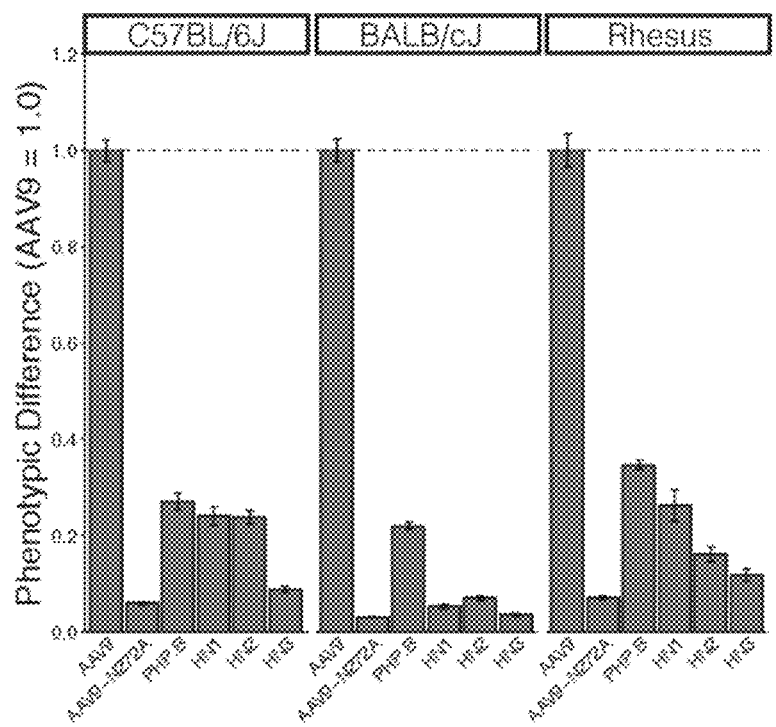
Figure 17B:
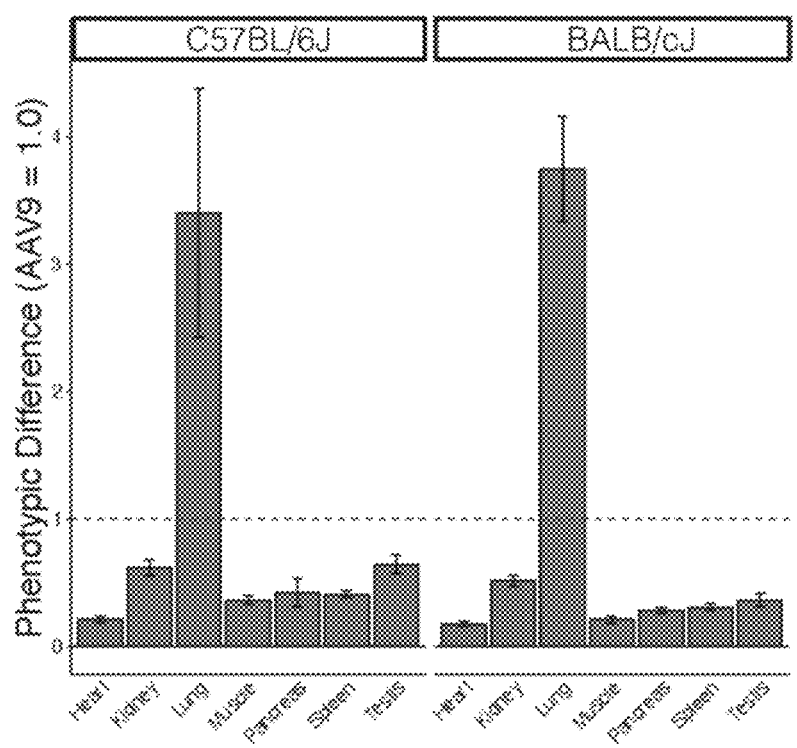
Figure 17C:
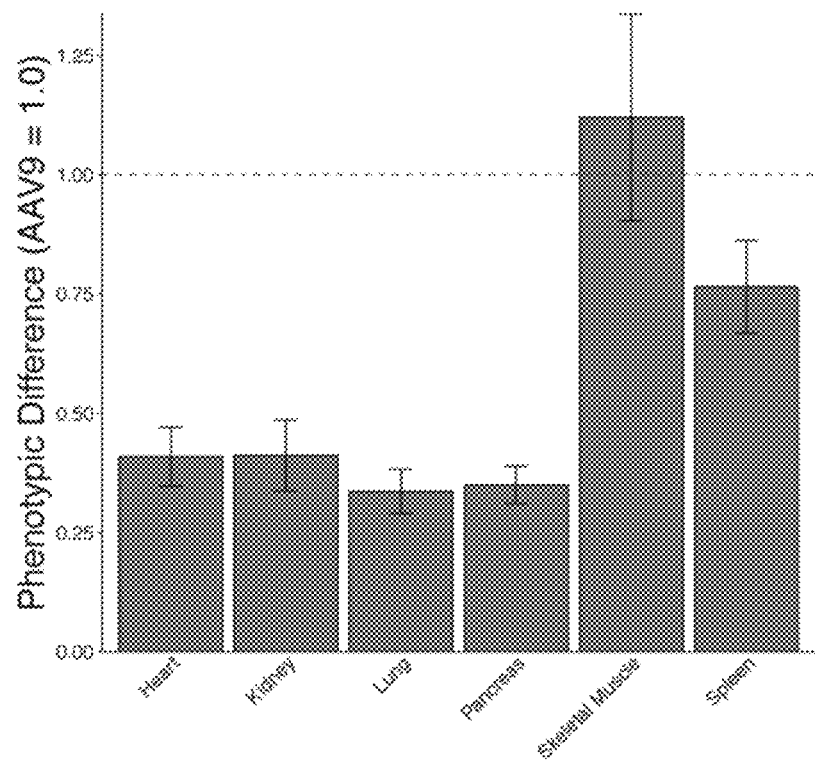
Figure 17D:
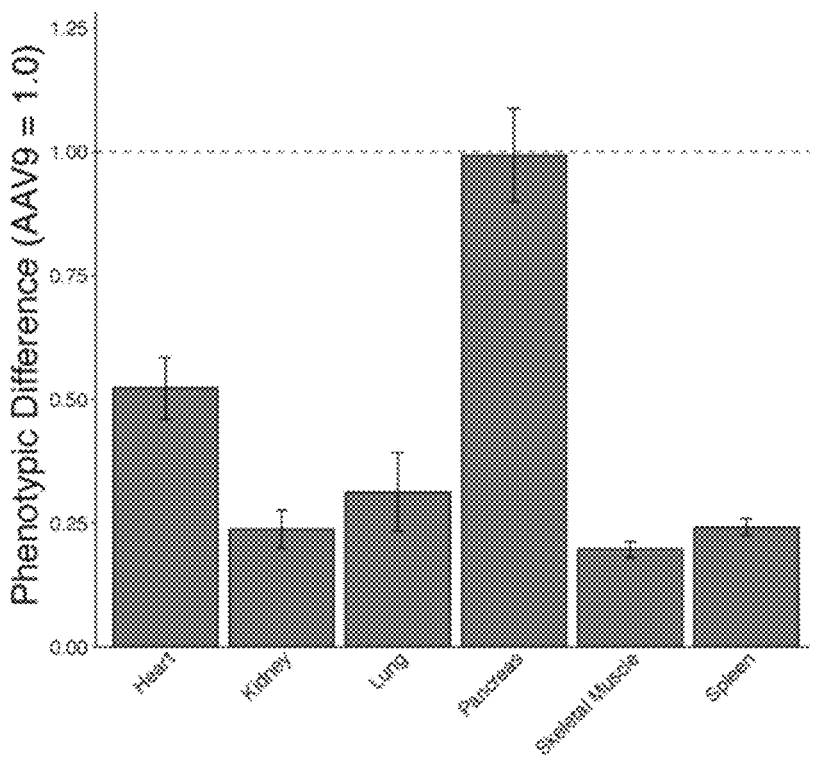

With the successful establishment of the TRADE system, we performed two AAV capsid directed evolution experiments; one used 8-week-old male C57BL/6J mice and the other used one 8-month-old male rhesus macaque. We produced an AAV9-N272A-hSynI-GFP-TRADE-Lib library composed of AAV9-derived mutant capsids that have a GGGS(N8)GGGGS (SEQ ID NO:2) peptide insertion at the position of Q588 where $N_8$ represents a random 8-mer peptide encoded by $(NNK)_8$. For the peptide insertion, Q588 was substituted with each peptide sequence. The diversity of the AAV library was at least $10^7$. In the mouse directed evolution experiment, we infused the AAV library via the tail vein at a dose of $3\times10^{11}$ vector genomes (vg) per mouse. For the second round of selection, we injected the AAV library at a dose of $1\times10^{12}$, $1\times10^{11}$, $1\times10^{10}$, or $1\times10^9$ vector genomes (vg) using two mice. For the third round of selection, we injected the AAV library at a dose of $1\times10^{11}$ vg using two mice. We harvested brain tissues twelve days after injection, and separated them into three regions, i.e., the cerebrum, the cerebellum and the brain stem. Only the cerebrum samples were used for the directed evolution experiments. We extracted total RNA from the cerebrum, reverse-transcribed the RNA using an oligo dT primer, and amplified the peptide region including the flanking regions by a pair of the cap gene-specific PCR primers. The RT-PCR products were then used to create the next AAV9-N272A-hSynI-TRADE-Lib plasmid library, which was subsequently used to produce the next AAV9-N272A-hSynI-TRADE-Lib virus library. For the second and third round selection, we packaged an AAV9-N272A-hSynI-TRADE-Lib genome that was devoid of the GFP ORF. In the non-human primate directed evolution experiment, we infused the AAV9-N272A-hSynI-GFP-TRADE-Lib library via the saphenous vein at a dose of $2.0\times10^{12}$ vg per kg. Twelve days post-injection, the whole brain was harvested and sliced using a brain matrix, treated with RNAlater (Thermo Fisher Scientific), and stored frozen. Total RNA was then extracted from the following brain regions: frontal cortex, occipital cortex, cerebellum (Purkinje and granular layers), medulla, pons, frontal cortex, hypothalamus, thalamus, cingulate gyrus, caudate nucleus, putamen, hippocampus, and preoptic area. We retrieved the peptide sequences by RT-PCR in the same manner as described above except that we performed nested PCR to obtain PCR products sufficient for the downstream Illumina and Sanger sequencing procedures. For some samples, we cloned the first PCR products directly into a plasmid backbone without performing nested PCR for Sanger sequencing. Following three rounds of selection in mice (Table 1) and one round of selection in non-human primate, we identified a number of potentially transduction-enhancing peptides inserted into the AAV9 capsids (Table 2). We then generated a barcoded AAV library and utilized DNA/RNA Barcode-Seq technology, previously developed in the Nakai lab (Adachi et al. *Nat Commun* 5, 3075 (2014); and PCT/US2017/068050), to compare the transduction efficiency, tropism/biodistribution, and pharmacokinetics of 26 selected novel AAV variants (Table 3) following intravenous administration in two commonly used mouse lines (C57BL/6J and BALB/cJ) and one rhesus macaque. As a result, we have found: (1) Some of the novel variants identified by TRADE technology, in particular AAV9-N272A-TTNLAKNS (HN1) and AAV9-N272A-QQNGTRPS (HN2), performed up to 8 times better than AAV9 in the brain of C57BL/6J mice (FIG. 14B and FIG. 14C). For HNx designation, please refer to Table 3. (2) As previously reported by Hordeaux et al. (Hordeaux et al. 2018), AAV-PHP.B transduced the brain of BALB/cJ mice only at a level comparable to or lower than that of AAV9 (FIG. 14B and FIG. 14C), demonstrating a mouse strain dependency for AAV-PHP.B's robust neurotropic enhancement. (3) In contrast, AAV9-N272A-TTNLAKNS (HN1) and AAV9-N272A-QQNGTRPS (HN2) retained robust neuronal transduction in BALB/cJ mice showing up to 7 times better transduction than AAV9 (FIG. 14B). (4) In a rhesus macaque, many of the novel AAV mutants showed enhanced neuronal transduction, up to 4-fold greater than AAV9 in certain brain regions, while AAV-PHP.B transduced non-human primate brain similarly to or lower than AAV9. In particular, AAV9-N272A-TTNLAKNS (HN1) transduced the non-human primate brain best in multiple brain regions (FIG. 14C and FIG. 14D). (5) All of the AAV9-N272A-derived variants including HN1, HN2 and HN3 showed varying degrees of liver-detargeting properties in mice and rhesus macaques (FIG. 17A). (6) AAV9-N272A-TTNLAKNS (HN1) and AAV9-N272A-QQNGTRPS (HN2) can transduce cells with the hSynI enhancer-promoter transcriptional activity in the lung up to 17 times better than AAV9 in mice (FIG. 17B, Tables 4 and 6). (7) AAV9-N272A-TTNLAKNS (HN1) exhibits vector genome dissemination to peripheral organs to a lesser degree compared to AAV9 (FIG. 17C and FIG. 17D). The AAV Barcode-Seq data are summarized in Tables 4 to 9. Representative data presented in Tables 4 to 9 are also shown in a graph format in FIG. 14B, FIG. 14C and FIG. 17A, FIG. 17B, FIG. 17C, and FIG. 17D.

TABLE 1

Peptide sequences identified by the hSyn1-TRADE system using an AAV9-N272N-GGGS(N₈)GGGGS library targeting mouse brain neurons.

| 1st round | | 2nd round | | 3rd round | |
|---|---|---|---|---|---|
| ADKPPGLS | SEQ ID NO: 3 | APTNFAHP | SEQ ID NO: 97 | AGAAYTPA (2) | SEQ ID NO: 150 |
| AGEDGSSR | SEQ ID NO: 4 | AQTNLAAG | SEQ ID NO: 98 | APSVSREK (2) | SEQ ID NO: 151 |
| ALGTATQR | SEQ ID NO: 5 | ASLPNLGQ | SEQ ID NO: 99 | DYMHKTGL | SEQ ID NO: 152 |
| ALNTALVE | SEQ ID NO: 6 | DYMHNTGL | SEQ ID NO: 100 | EEDAQLLI (2) | SEQ ID NO: 14 |
| AMVRLTHN | SEQ ID NO: 7 | DYMHTTGL | SEQ ID NO: 101 | ENKSAPLP | SEQ ID NO: 18 |
| ASRDPSAT | SEQ ID NO: 8 | ERNAWHAG | SEQ ID NO: 102 | GDYTVQRP | SEQ ID NO: 107 |
| DANDARQR | SEQ ID NO: 9 | ETQATPMP | SEQ ID NO: 103 | GGMNETTR | SEQ ID NO: 153 |
| DLARMAAA | SEQ ID NO: 10 | EWEDSARS | SEQ ID NO: 104 | GGSAFVTG | SEQ ID NO: 154 |
| DQGSITAH | SEQ ID NO: 11 | FTGDTDTL | SEQ ID NO: 105 | GGSPLAHP | SEQ ID NO: 21 |
| DRTPGVNV | SEQ ID NO: 12 | FTNRTSTT | SEQ ID NO: 106 | GNSHTGSS | SEQ ID NO: 155 |
| DTDTLSPG | SEQ ID NO: 13 | GDYTVQRP | SEQ ID NO: 107 | GPQEGSER (2) | SEQ ID NO: 109 |
| EEDAQLLI | SEQ ID NO: 14 | GGLRTDYG | SEQ ID NO: 108 | GQRGLPIA | SEQ ID NO: 27 |
| EKLNDWPT | SEQ ID NO: 15 | GGSPLAHP | SEQ ID NO: 21 | GSNHTQSL | SEQ ID NO: 110 |
| ELNSARQV | SEQ ID NO: 16 | GKQPVQPY | SEQ ID NO: 24 | HQVTSSGA (4) | SEQ ID NO: 33 |

TABLE 1-continued

Peptide sequences identified by the hSyn1-TRADE system using an AAV9-N272N-GGGS(N$_8$)GGGGS library targeting mouse brain neurons.

| 1st round | | 2nd round | | 3rd round | |
|---|---|---|---|---|---|
| ELQSFAGL | SEQ ID NO: 17 | GPQEGSER | SEQ ID NO: 109 | LEQQRGAS | SEQ ID NO: 113 |
| ENKSAPLP | SEQ ID NO: 18 | GSNHTQSL | SEQ ID NO: 110 | LERNRDSD | SEQ ID NO: 39 |
| ERTAVKGN | SEQ ID NO: 19 | GTPQTTKE | SEQ ID NO: 29 | LLVTARSH (3) | SEQ ID NO: 44 |
| GGIQTVVT | SEQ ID NO: 20 | HDRDTRQA | SEQ ID NO: 111 | MESQRANS (2) | SEQ ID NO: 117 |
| GGSPLAHP | SEQ ID NO: 21 | LDQNRRPQ | SEQ ID NO: 112 | MSGQGYQA (2) | SEQ ID NO: 50 |
| GGTAAQGV | SEQ ID NO: 22 | LEQQRGAS | SEQ ID NO: 113 | NSARTQLS | SEQ ID NO: 156 |
| GKMASGSL | SEQ ID NO: 23 | LERNRDSD | SEQ ID NO: 39 | PLTILNRH | SEQ ID NO: 157 |
| GKQPVQPY | SEQ ID NO: 24 | LGGNAQGL | SEQ ID NO: 114 | QGTRTNPP | SEQ ID NO: 158 |
| GNPHTGST | SEQ ID NO: 25 | LLVTTRSH | SEQ ID NO: 115 | QQNGTRPS (4) | SEQ ID NO: 128 |
| GPTLGGSG | SEQ ID NO: 26 | LVTNTTR | SEQ ID NO: 116 | QSGDSALN (3) | SEQ ID NO: 67 |
| GQRGLPIA | SEQ ID NO: 27 | MESQRANS | SEQ ID NO: 117 | QSSAMPRN (2) | SEQ ID NO: 159 |
| GREPRRLH | SEQ ID NO: 28 | MISQTLMA | SEQ ID NO: 118 | SATISLQV | SEQ ID NO: 136 |
| GTPQTTKE | SEQ ID NO: 29 | MMSQSLRA | SEQ ID NO: 119 | SHNSQPVA | SEQ ID NO: 160 |
| GVTERPNR | SEQ ID NO: 30 | NNVQSALN | SEQ ID NO: 120 | SHTNLRDT | SEQ ID NO: 137 |
| HLGDNLAR | SEQ ID NO: 31 | NSARTQLS | SEQ ID NO: 121 | SSGYLTAN | SEQ ID NO: 139 |
| HPGSGAGP | SEQ ID NO: 32 | PQWNRTPL | SEQ ID NO: 122 | TAQGAAFR (4) | SEQ ID NO: 161 |
| HQVTSSGA | SEQ ID NO: 33 | PRFNNSSL | SEQ ID NO: 123 | TPGLNNAR | SEQ ID NO: 162 |
| HVGSQMHA | SEQ ID NO: 34 | PRPTVVGT | SEQ ID NO: 60 | TSLGTPEA | SEQ ID NO: 163 |
| IG*TVPMQ | SEQ ID NO: 35 | PVDGGRHL | SEQ ID NO: 124 | TTNLAKNS (6) | SEQ ID NO: 164 |
| KFTRDGPY | SEQ ID NO: 36 | PWFNKSSL | SEQ ID NO: 125 | VVQGEQKR (4) | SEQ ID NO: 146 |
| KGPAEQGH | SEQ ID NO: 37 | QDMNSQRS | SEQ ID NO: 126 | WSPDAVEG | SEQ ID NO: 165 |
| LAHSPRLW | SEQ ID NO: 38 | QGASNSQL | SEQ ID NO: 127 | WSQDAVKG (2) | SEQ ID NO: 148 |
| LERNRDSD | SEQ ID NO: 39 | QQNGTRPS | SEQ ID NO: 128 | WTGGGSGT (3) | SEQ ID NO: 149 |
| LETHTSLT | SEQ ID NO: 40 | QRSAYPTS | SEQ ID NO: 129 | WTGGRHL | SEQ ID NO: 166 |
| LHDGKYST | SEQ ID NO: 41 | QRTPSITP | SEQ ID NO: 130 | | |

TABLE 1-continued

Peptide sequences identified by the hSyn1-TRADE system using an AAV9-N272N-GGGS(N$_8$)GGGGS library targeting mouse brain neurons.

| 1st round | | 2nd round | | 3rd round |
|---|---|---|---|---|
| LKATGRGK | SEQ ID NO: 42 | QWMKEQAG | SEQ ID NO: 131 | |
| LLPGSADG | SEQ ID NO: 43 | RDGRHPSE | SEQ ID NO: 132 | |
| LLVTARSH | SEQ ID NO: 44 | RGTVTVEQ | SEQ ID NO: 133 | |
| LPEVEPTN | SEQ ID NO: 45 | RPANHSTA | SEQ ID NO: 134 | |
| LPWENSSQ | SEQ ID NO: 46 | RQGDADTL | SEQ ID NO: 135 | |
| LQRNSDAN | SEQ ID NO: 47 | SATISLQV | SEQ ID NO: 136 | |
| LQSAPRAT | SEQ ID NO: 48 | SHTNLRDT | SEQ ID NO: 137 | |
| MLGSQVPT | SEQ ID NO: 49 | SRMGETPQ | SEQ ID NO: 138 | |
| MSGQGYQA | SEQ ID NO: 50 | SSGYLTAN | SEQ ID NO: 139 | |
| NPGRDFRD | SEQ ID NO: 51 | SSVVSQGP | SEQ ID NO: 79 | |
| NQPSDYVS | SEQ ID NO: 52 | TGNSPEQA | SEQ ID NO: 140 | |
| NSVGSADK | SEQ ID NO: 53 | THSQGRLA | SEQ ID NO: 141 | |
| NVQRTQRG | SEQ ID NO: 54 | TPIVGSNV | SEQ ID NO: 142 | |
| PAQLNGPR | SEQ ID NO: 55 | TPPKSPSM | SEQ ID NO: 143 | |
| PERERLPR | SEQ ID NO: 56 | TRMDERSP | SEQ ID NO: 144 | |
| PGNGSHTM | SEQ ID NO: 57 | TTATTSIT | SEQ ID NO: 145 | |
| PIPGTPQP | SEQ ID NO: 58 | VVQGEQKR | SEQ ID NO: 146 | |
| PMSVPASN | SEQ ID NO: 59 | WNDRSGER | SEQ ID NO: 147 | |
| PRPTVVGT | SEQ ID NO: 60 | WSQDAVKG | SEQ ID NO: 148 | |
| PRTNRGPE | SEQ ID NO: 61 | WTGGGSGT | SEQ ID NO: 149 | |
| PVANPTTA | SEQ ID NO: 62 | | | |
| PVLGGPPK | SEQ ID NO: 63 | | | |
| QGSRQGSS | SEQ ID NO: 64 | | | |
| QMAETPIS | SEQ ID NO: 65 | | | |

TABLE 1-continued

Peptide sequences identified by the hSyn1-TRADE system using an AAV9-N272N-GGGS(N$_8$)GGGGS library targeting mouse brain neurons.

| 1st round | 2nd round | 3rd round |
|---|---|---|
| QMLGIGRS SEQ ID NO: 66 | | |
| QSGDSALN SEQ ID NO: 67 | | |
| RAGLTSSE SEQ ID NO: 68 | | |
| RLDNTGVG SEQ ID NO: 69 | | |
| RMPGKPYS SEQ ID NO: 70 | | |
| RVAGASQP SEQ ID NO: 71 | | |
| RVESSQLE SEQ ID NO: 72 | | |
| SARTGASE SEQ ID NO: 73 | | |
| SERNRASM SEQ ID NO: 74 | | |
| SIDVRMAA SEQ ID NO: 75 | | |
| SRDGHILR SEQ ID NO: 76 | | |
| SRQVVLPG SEQ ID NO: 77 | | |
| SSRGYTST SEQ ID NO: 78 | | |
| SSVVSQGP SEQ ID NO: 79 | | |
| SVAESGRE SEQ ID NO: 80 | | |
| TALTANTQ SEQ ID NO: 81 | | |
| TESSVGNL SEQ ID NO: 82 | | |
| TGREGANL SEQ ID NO: 83 | | |
| TLSEPPKK SEQ ID NO: 84 | | |
| TNAVSGKS SEQ ID NO: 85 | | |
| TRAPTIHL SEQ ID NO: 86 | | |
| TRESTDRG SEQ ID NO: 87 | | |

TABLE 1-continued

Peptide sequences identified by the hSyn1-TRADE system using an AAV9-N272N-GGGS($N_8$)GGGGS library targeting mouse brain neurons.

| 1st round | | 2nd round | 3rd round |
|---|---|---|---|
| TVAAAPNL | SEQ ID NO: 88 | | |
| TYHNNTPR | SEQ ID NO: 89 | | |
| VSNSTRTS | SEQ ID NO: 90 | | |
| VTLQIDTK | SEQ ID NO: 91 | | |
| WMSRPGPT | SEQ ID NO: 92 | | |
| WPYRGLTQ | SEQ ID NO: 93 | | |
| WRRQGSRA | SEQ ID NO: 94 | | |
| YAQRFAKM | SEQ ID NO: 95 | | |
| YNSPRQTV | SEQ ID NO: 96 | | |

The table lists peptide insertions on AAV9-N272A after each of three rounds of selection. The numbers in parentheses indicate the frequency of each peptide among a total of 69 peptides identified after the three round of selection. Peptides with no number were found only once. The sequences of the peptide region were determined by Sanger sequencing. Actual peptide sequences were randomized octapeptides flanked by glycine-serine linkers such that position Q588 was substituted with GGGS($N_8$)GGGGS. For example,
"-TNHQSA GGGSTTNLAKNSGGGGS AQAQTG-" for TTNLAKNS and
"-TNHQSA GGGSQQNGTRPSGGGGS AQAQTG-" for QQNGTRPS.

TABLE 2

Peptide sequences identified by the hSyn1-TRADE system using an AAV9-N272A-GGGS($N_8$)GGGGS library targeting rhesus macaque brain neurons.
1st round

| | |
|---|---|
| AVAGDRLL | SEQ ID NO: 167 |
| DLLTRSVS | SEQ ID NO: 168 |
| EWKTQLAL | SEQ ID NO: 169 |
| GNINVVPH | SEQ ID NO: 170 |
| GSPAASSW | SEQ ID NO: 171 |
| KHSLTLES | SEQ ID NO: 172 |
| KPVSTDTF | SEQ ID NO: 173 |
| LDRSGSTG | SEQ ID NO: 174 |
| LGAQNHVV | SEQ ID NO: 175 |
| LMATDYGP | SEQ ID NO: 176 |
| LRATDYGP | SEQ ID NO: 177 |
| MERTEPLG | SEQ ID NO: 178 |
| NDGLRLHL | SEQ ID NO: 179 |
| NLSAHSHA | SEQ ID NO: 180 |
| NLSAHSHD | SEQ ID NO: 181 |
| RALDLVTR | SEQ ID NO: 182 |
| SAGMARNS | SEQ ID NO: 183 |
| SGQRVGSA | SEQ ID NO: 184 |
| SGQRVGSD | SEQ ID NO: 185 |
| TAQGAAFR | SEQ ID NO: 161 |
| TGRPEQPK | SEQ ID NO: 186 |
| THSPIKLP | SEQ ID NO: 187 |
| TQFSQAQR | SEQ ID NO: 188 |
| VGDSANLR | SEQ ID NO: 189 |

The sequences of the peptide region were determined either by Illumina sequencing or Sanger sequencing. Actual peptide sequences were randomized octapeptides flanked by glycine-serine linkers such that position Q588 was substituted with GGGS($N_8$)GGGGS. These peptides were recovered from frontal cortex, occipital cortex, hypothalamus and thalamus.

TABLE 3

A list of the 29 AAV capsids contained in the DNA/RNA-barcoded dsAAV-hSyn1-GFP-BCLib library used for phenotype determination of each AAV strain.

| AAV strain (AAV capsid) | Abbreviation | Number of viral clones in the AAV library | Note |
|---|---|---|---|
| AAV9 | AAV9 | 15 | Reference |
| AAV9-N272A | AAV9-N272A | 5 | Reference |
| AAV-PHP.B | AAV-PHP.B | 2 | Reference |
| AAV9-N272A-TTNLAKNS (peptide insertion site SEQ ID NO: 164) | HN1 | 2 | TRADE variant (C57BL/6J) |
| AAV9-N272A-QQNGTRPS (peptide insertion site SEQ ID NO: 128) | HN2 | 2 | TRADE variant (C57BL/6J) |
| AAV9-N272A-SGQRVGSD (peptide insertion site SEQ ID NO: 185) | HN3 | 2 | TRADE variant (rhesus macaque) |
| AAV9-N272A-AVAGDRLL (peptide insertion site SEQ ID NO: 167) | HN4 | 2 | TRADE variant (rhesus macaque) |
| AAV9-N272A-DLLTRSVS (peptide insertion site SEQ ID NO: 168) | HN5 | 2 | TRADE variant (rhesus macaque) |
| AAV9-N272A-EWKTQLAL (peptide insertion site SEQ ID NO: 169) | HN6 | 2 | TRADE variant (rhesus macaque) |
| AAV9-N272A-GNINVVPH (peptide insertion site SEQ ID NO: 170) | HN7 | 2 | TRADE variant (rhesus macaque) |
| AAV9-N272A-GSPAASSW (peptide insertion site SEQ ID NO: 171) | HN8 | 2 | TRADE variant (rhesus macaque) |
| AAV9-N272A-KHSLTLES (peptide insertion site SEQ ID NO: 172) | HN9 | 2 | TRADE variant (rhesus macaque) |
| AAV9-N272A-KPVSTDTF (peptide insertion site SEQ ID NO: 173) | HN10 | 2 | TRADE variant (rhesus macaque) |
| AAV9-N272A-LDRSGSTG (peptide insertion site SEQ ID NO: 174) | HN11 | 2 | TRADE variant (rhesus macaque) |
| AAV9-N272A-LGAQNHVV (peptide insertion site SEQ ID NO: 175) | HN12 | 2 | TRADE variant (rhesus macaque) |
| AAV9-N272A-LRATDYGP (peptide insertion site SEQ ID NO: 177) | HN13 | 2 | TRADE variant (rhesus macaque) |
| AAV9-N272A-MERTEPLG (peptide insertion site SEQ ID NO: 178) | HN14 | 2 | TRADE variant (rhesus macaque) |
| AAV9-N272A-NDGLRLHL (peptide insertion site SEQ ID NO: 179) | HN15 | 2 | TRADE variant (rhesus macaque) |
| AAV9-N272A-NLSAHSHD (peptide insertion site SEQ ID NO: 181) | HN16 | 2 | TRADE variant (rhesus macaque) |
| AAV9-N272A-RALDLVTR (peptide insertion site SEQ ID NO: 182) | HN17 | 2 | TRADE variant (rhesus macaque) |

TABLE 3-continued

A list of the 29 AAV capsids contained in the DNA/RNA-barcoded dsAAV-hSyn1-
GFP-BCLib library used for phenotype determination of each AAV strain.

| AAV strain (AAV capsid) | Abbreviation | Number of viral clones in the AAV library | Note |
| --- | --- | --- | --- |
| AAV9-N272A-SAGMARNS (peptide insertion site SEQ ID NO: 183) | HN18 | 2 | TRADE variant (rhesus macaque) |
| AAV9-N272A-TAQGAAFR (peptide insertion site SEQ ID NO: 161) | HN19 | 2 | TRADE variant (rhesus macaque) |
| AAV9-N272A-TGRPEQPK (peptide insertion site SEQ ID NO: 186) | HN20 | 2 | TRADE variant (rhesus macaque) |
| AAV9-N272A-THSPIKLP (peptide insertion site SEQ ID NO: 187) | HN21 | 2 | TRADE variant (rhesus macaque) |
| AAV9-N272A-TQFSQAQR (peptide insertion site SEQ ID NO: 188) | HN22 | 2 | TRADE variant (rhesus macaque) |
| AAV9-N272A-VGDSANLR (peptide insertion site SEQ ID NO: 189) | HN23 | 2 | TRADE variant (rhesus macaque) |
| AAV9-N272A-HQVTSSGA (peptide insertion site SEQ ID NO: 33) | HN24 | 2 | TRADE variant (mouse) |
| AAV9-N272A-LLVTARSH (peptide insertion site SEQ ID NO: 44) | HN25 | 2 | TRADE variant (mouse) |
| AAV9-N272A-VVQGEQKR (peptide insertion site SEQ ID NO: 146) | HN26 | 2 | TRADE variant (mouse) |

The novel AAV9-hSyn1-TRADE-derived capsid variants were selected from those identified following three rounds of selection in mice (Table 1) and one round of selection in a rhesus macaque (Table 2). Each recovered AAV variant was assigned an abbreviation, HNx. A DNA/RNA-barcoded dsAAV-hSyn1-GFP-BCLib library containing was constructed such that each AAV variant packaged a unique dsAAV-hSyn1-GFP-BC viral genome expressing AAV variant-specific RNA barcodes. The number of unique AAV barcode clones for each variant, including critical reference variants, is presented in this table.

TABLE 4

Brain neuronal transduction efficiency and biodistribution of the TRADE-identified
AAV variants in C57BL/6J mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
| --- | --- | --- | --- | --- | --- | --- | --- | --- | --- | --- |
| AAV9 | 1.00 | 1.00 | 1.00 | 1.00 | 1.00 | 1.00 | 1.00 | 1.00 | 1.00 | 1.00 |
| AAV9-N272A | 1.93 | 0.22 | 0.82 | 2.11 | 0.06 | 0.51 | 0.17 | 0.25 | 4.49 | 1.42 |
| AAV-PHP.B | 9.42 | 0.64 | 0.92 | 2.35 | 0.27 | 0.81 | 0.36 | 0.62 | 2.69 | 1.45 |
| HN1 | 8.01 | 2.74 | 0.21 | 0.62 | 0.24 | 3.40 | 0.36 | 0.42 | 0.41 | 0.64 |
| HN2 | 6.52 | 1.19 | 0.36 | 0.56 | 0.24 | 2.55 | 0.32 | 0.33 | 0.66 | 0.91 |
| HN3 | 2.35 | 0.41 | 0.95 | 1.29 | 0.09 | 0.45 | 0.20 | 0.25 | 2.57 | 1.45 |
| HN4 | 0.87 | 0.15 | 0.65 | 2.96 | 0.02 | 0.48 | 0.11 | 0.21 | 4.02 | 1.22 |
| HN5 | 0.46 | 0.10 | 0.57 | 2.66 | 0.01 | 0.47 | 0.09 | 0.21 | 3.90 | 1.10 |
| HN6 | 0.37 | 0.22 | 0.64 | 3.13 | 0.01 | 0.52 | 0.08 | 0.27 | 4.27 | 1.22 |
| HN7 | 1.03 | 0.21 | 0.40 | 0.54 | 0.25 | 0.17 | 0.23 | 0.10 | 0.75 | 0.43 |
| HN8 | 0.74 | 0.11 | 0.61 | 2.61 | 0.02 | 0.45 | 0.09 | 0.16 | 3.27 | 1.06 |
| HN9 | 1.47 | 0.28 | 0.62 | 1.49 | 0.08 | 0.30 | 0.15 | 0.16 | 2.41 | 0.82 |
| HN10 | 1.40 | 0.18 | 0.64 | 1.48 | 0.04 | 0.24 | 0.12 | 0.16 | 2.64 | 0.97 |
| HN11 | 1.38 | 0.21 | 0.73 | 1.37 | 0.05 | 0.29 | 0.15 | 0.17 | 3.17 | 1.12 |
| HN12 | 0.80 | 0.17 | 0.26 | 0.42 | 0.24 | 0.16 | 0.20 | 0.06 | 0.49 | 0.21 |
| HN13 | 1.59 | 0.28 | 0.77 | 1.17 | 0.10 | 0.28 | 0.19 | 0.18 | 2.28 | 0.93 |
| HN14 | 0.45 | 0.05 | 0.47 | 1.31 | 0.01 | 0.20 | 0.07 | 0.14 | 1.86 | 0.65 |

TABLE 4-continued

Brain neuronal transduction efficiency and biodistribution of the TRADE-identified AAV variants in C57BL/6J mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
|---|---|---|---|---|---|---|---|---|---|---|
| HN15 | 0.50 | 0.21 | 0.68 | 3.48 | 0.01 | 0.58 | 0.10 | 0.24 | 4.70 | 1.30 |
| HN16 | 1.43 | 0.24 | 0.58 | 1.28 | 0.02 | 0.32 | 0.11 | 0.22 | 3.70 | 1.07 |
| HN17 | 0.29 | 0.07 | 0.50 | 2.80 | 0.01 | 0.46 | 0.08 | 0.19 | 3.73 | 1.05 |
| HN18 | 1.46 | 0.12 | 0.68 | 1.78 | 0.11 | 0.28 | 0.17 | 0.14 | 2.10 | 0.92 |
| HN19 | 0.56 | 0.10 | 0.57 | 3.07 | 0.01 | 0.52 | 0.09 | 0.18 | 3.98 | 1.16 |
| HN20 | 1.68 | 0.35 | 0.90 | 1.10 | 0.18 | 0.29 | 0.24 | 0.18 | 1.89 | 0.89 |
| HN21 | 0.26 | 0.08 | 0.50 | 2.53 | 0.01 | 0.46 | 0.06 | 0.14 | 3.44 | 1.01 |
| HN22 | 0.82 | 0.06 | 0.51 | 2.55 | 0.02 | 0.42 | 0.10 | 0.19 | 3.32 | 1.05 |
| HN23 | 2.45 | 0.26 | 0.72 | 1.02 | 0.05 | 0.30 | 0.15 | 0.21 | 2.25 | 1.12 |
| HN24 | 1.33 | 0.22 | 0.63 | 1.31 | 0.05 | 0.28 | 0.14 | 0.15 | 2.83 | 0.90 |
| HN25 | 0.37 | 0.12 | 0.64 | 3.25 | 0.02 | 0.53 | 0.09 | 0.22 | 4.35 | 1.23 |
| HN26 | 0.73 | 0.14 | 0.63 | 2.53 | 0.06 | 0.40 | 0.12 | 0.17 | 2.86 | 1.07 |

A DNA/RNA-barcoded dsAAV-hSynI-GFP-BC library (dsAAV-hSynI-GFP-BCLib) containing 26 novel AAV variants identified by TRADE and control AAV capsids was injected intravenously into 3 C57BL/6J mice at a dose of $5 \times 10^{11}$ vg per mouse (for the library, see Table 3). Two weeks post-injection, various tissues were harvested and analyzed for brain transduction by AAV RNA Barcode-Seq and biodistribution to peripheral organs by AAV DNA Barcode-Seq. All the values are normalized with those of AAV9 (AAV9 = 1.0).

TABLE 5

Pharmacokinetic profiles of TRADE-identified AAV variants in C57BL/6J mice following intravenous administration.

| | 1 m | 10 m | 30 m | 1 h | 4 h | 8 h | 24 h | 72 h |
|---|---|---|---|---|---|---|---|---|
| AAV9 | 1.00 | 1.00 | 1.00 | 1.00 | 1.00 | 1.00 | 1.00 | 1.00 |
| AAV9-N272A | 1.16 | 1.17 | 1.28 | 1.34 | 1.77 | 2.02 | 3.14 | 0.13 |
| AAV-PHP.B | 1.38 | 1.42 | 1.44 | 1.62 | 1.88 | 2.15 | 3.14 | 0.39 |
| HN1 | 0.87 | 0.47 | 0.29 | 0.29 | 0.27 | 0.31 | 0.37 | 0.02 |
| HN2 | 0.79 | 0.60 | 0.49 | 0.55 | 0.59 | 0.66 | 0.91 | 0.03 |
| HN3 | 1.12 | 1.15 | 1.21 | 1.32 | 1.65 | 1.88 | 3.05 | 0.04 |
| HN4 | 1.32 | 1.50 | 1.43 | 1.52 | 2.01 | 2.37 | 3.78 | 0.03 |
| HN5 | 1.14 | 1.30 | 1.37 | 1.42 | 1.84 | 2.03 | 3.37 | 0.02 |
| HN6 | 1.21 | 1.34 | 1.43 | 1.60 | 1.99 | 2.38 | 3.90 | 0.02 |
| HN7 | 0.92 | 0.88 | 0.93 | 0.93 | 1.09 | 1.21 | 1.22 | 0.03 |
| HN8 | 1.20 | 1.29 | 1.30 | 1.44 | 1.83 | 2.10 | 3.42 | 0.03 |
| HN9 | 0.94 | 0.91 | 0.97 | 0.99 | 1.26 | 1.36 | 1.97 | 0.04 |
| HN10 | 0.98 | 0.98 | 1.00 | 1.06 | 1.31 | 1.36 | 1.89 | 0.02 |
| HN11 | 1.00 | 1.04 | 1.04 | 1.14 | 1.39 | 1.48 | 2.11 | 0.02 |
| HN12 | 0.93 | 0.93 | 0.84 | 0.79 | 0.71 | 0.61 | 0.62 | 0.01 |
| HN13 | 0.95 | 0.90 | 0.95 | 0.95 | 1.20 | 1.28 | 1.60 | 0.03 |
| HN14 | 0.94 | 0.95 | 1.00 | 1.08 | 1.41 | 1.58 | 2.56 | 0.01 |
| HN15 | 1.39 | 1.56 | 1.67 | 1.66 | 2.20 | 2.76 | 4.26 | 0.03 |
| HN16 | 0.98 | 1.00 | 1.04 | 1.15 | 1.46 | 1.63 | 2.77 | 0.02 |
| HN17 | 1.32 | 1.28 | 1.27 | 1.31 | 1.94 | 2.13 | 4.03 | 0.04 |
| HN18 | 1.10 | 1.06 | 0.96 | 0.93 | 0.82 | 0.84 | 1.27 | 0.01 |
| HN19 | 1.39 | 1.39 | 1.51 | 1.49 | 2.04 | 2.50 | 4.09 | 0.03 |
| HN20 | 1.15 | 1.09 | 1.19 | 1.14 | 1.41 | 1.70 | 1.97 | 0.06 |
| HN21 | 1.25 | 1.19 | 1.34 | 1.38 | 1.90 | 1.99 | 3.30 | 0.02 |
| HN22 | 1.16 | 1.24 | 1.32 | 1.35 | 1.74 | 2.13 | 3.74 | 0.02 |
| HN23 | 1.03 | 1.02 | 1.04 | 1.14 | 1.43 | 1.64 | 2.56 | 0.03 |
| HN24 | 0.99 | 1.01 | 1.05 | 1.16 | 1.45 | 1.58 | 2.38 | 0.03 |
| HN25 | 1.29 | 1.40 | 1.44 | 1.49 | 1.93 | 2.49 | 3.74 | 0.03 |
| HN26 | 1.21 | 1.19 | 1.29 | 1.30 | 1.74 | 2.03 | 3.09 | 0.03 |

AAV DNA Barcode-Seq analysis was performed on the blood samples obtained from the mice injected with $1 \times 10^{13}$ vg/kg of the DNA/RNA-barcoded dsAAV-hSynI-GFP-BCLib library (see Table 3, n = 2) All the values are normalized with those of AAV9 (AAV9 = 1.0). All the values are normalized to AAV9 (AAV9 = 1.0).

TABLE 6

Brain neuronal transduction efficiency and biodistribution of the TRADE-identified AAV variants in BALB/cJ mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
|---|---|---|---|---|---|---|---|---|---|---|
| AAV9 | 1.00 | 1.00 | 1.00 | 1.00 | 1.00 | 1.00 | 1.00 | 1.00 | 1.00 | 1.00 |
| AAV9-N272A | 1.00 | 0.30 | 0.45 | 1.23 | 0.03 | 0.64 | 0.29 | 1.23 | 2.75 | 0.17 |
| AAV-PHP.B | 1.06 | 0.44 | 0.56 | 1.30 | 0.22 | 0.67 | 0.40 | 1.12 | 1.69 | 0.30 |

TABLE 6-continued

Brain neuronal transduction efficiency and biodistribution of the TRADE-identified AAV variants in BALB/cJ mice following intravenous administration.

| | Brain (RNA) | Lung (RNA) | Heart (DNA) | Kidney (DNA) | Liver (DNA) | Lung (DNA) | Muscle (DNA) | Pancreas (DNA) | Spleen (DNA) | Testis (DNA) |
|---|---|---|---|---|---|---|---|---|---|---|
| HN1 | 7.59 | 17.84 | 0.18 | 0.52 | 0.05 | 3.75 | 0.21 | 0.28 | 0.31 | 0.36 |
| HN2 | 3.26 | 4.71 | 0.31 | 0.52 | 0.07 | 3.13 | 0.25 | 0.39 | 0.69 | 0.44 |
| HN3 | 1.00 | 0.35 | 0.51 | 1.04 | 0.04 | 0.41 | 0.20 | 0.60 | 1.38 | 0.14 |
| HN4 | 0.41 | 0.41 | 0.29 | 1.58 | 0.01 | 0.44 | 0.16 | 1.18 | 2.50 | 0.09 |
| HN5 | 0.28 | 0.15 | 0.25 | 1.34 | 0.00 | 0.38 | 0.13 | 1.05 | 2.25 | 0.07 |
| HN6 | 0.25 | 0.06 | 0.30 | 1.60 | 0.01 | 0.45 | 0.17 | 1.17 | 2.69 | 0.07 |
| HN7 | 0.54 | 0.21 | 0.27 | 0.65 | 0.12 | 0.22 | 0.16 | 0.32 | 0.75 | 0.11 |
| HN8 | 0.34 | 0.03 | 0.28 | 1.53 | 0.01 | 0.38 | 0.14 | 0.94 | 2.10 | 0.07 |
| HN9 | 0.49 | 0.19 | 0.28 | 1.18 | 0.02 | 0.22 | 0.11 | 0.45 | 1.08 | 0.07 |
| HN10 | 0.54 | 0.19 | 0.33 | 1.25 | 0.01 | 0.30 | 0.14 | 0.50 | 1.82 | 0.08 |
| HN11 | 0.23 | 0.12 | 0.23 | 1.15 | 0.03 | 0.17 | 0.09 | 0.62 | 0.95 | 0.05 |
| HN12 | 0.34 | 0.13 | 0.19 | 0.98 | 0.03 | 0.12 | 0.07 | 0.23 | 0.48 | 0.04 |
| HN13 | 0.43 | 0.25 | 0.36 | 1.25 | 0.03 | 0.25 | 0.15 | 0.41 | 1.01 | 0.09 |
| HN14 | 0.22 | 0.08 | 0.20 | 0.93 | 0.02 | 0.14 | 0.08 | 0.38 | 0.68 | 0.04 |
| HN15 | 0.25 | 0.26 | 0.33 | 1.80 | 0.01 | 0.46 | 0.19 | 1.39 | 3.03 | 0.10 |
| HN16 | 0.62 | 0.25 | 0.32 | 0.93 | 0.01 | 0.41 | 0.16 | 0.71 | 1.55 | 0.10 |
| HN17 | 0.18 | 0.12 | 0.22 | 1.40 | 0.00 | 0.37 | 0.13 | 0.96 | 2.29 | 0.07 |
| HN18 | 0.75 | 0.16 | 0.40 | 1.46 | 0.04 | 0.29 | 0.15 | 0.59 | 1.36 | 0.08 |
| HN19 | 0.28 | 0.10 | 0.28 | 1.57 | 0.01 | 0.44 | 0.15 | 1.14 | 2.51 | 0.08 |
| HN20 | 0.69 | 0.11 | 0.42 | 0.56 | 0.08 | 0.31 | 0.13 | 0.53 | 0.85 | 0.12 |
| HN21 | 0.14 | 0.15 | 0.25 | 1.38 | 0.00 | 0.34 | 0.11 | 0.91 | 2.34 | 0.08 |
| HN22 | 0.41 | 0.09 | 0.22 | 1.33 | 0.01 | 0.36 | 0.12 | 1.01 | 2.09 | 0.07 |
| HN23 | 0.79 | 0.32 | 0.33 | 0.99 | 0.02 | 0.36 | 0.17 | 0.43 | 1.24 | 0.10 |
| HN24 | 0.56 | 0.25 | 0.34 | 1.17 | 0.02 | 0.34 | 0.14 | 0.53 | 1.33 | 0.08 |
| HN25 | 0.19 | 0.02 | 0.30 | 1.65 | 0.01 | 0.49 | 0.17 | 1.15 | 2.68 | 0.09 |
| HN26 | 0.31 | 0.11 | 0.33 | 1.52 | 0.02 | 0.35 | 0.17 | 0.84 | 1.77 | 0.09 |

A DNA/RNA-barcoded dsAAV-hSynl-GFP-BC library (dsAAV-hSynl-GFP-BCLib) containing 26 novel AAV variants identified by TRADE and control AAV capsids was injected intravenously into 3 BALB/cJ mice at a dose of $5 \times 10^{11}$ vg per mouse (for the library, see Table 3). Two weeks post-injection, various tissues were harvested and analyzed for brain transduction by AAV RNA Barcode-Seq and biodistribution to peripheral organs by AAV DNA Barcode-Seq. All the values are normalized with those of AAV9 (AAV9 = 1.0).

TABLE 7

Transduction efficiency of hSynl-TRADE-derived AAV variants in various brain regions of one rhesus macaque following intravenous administration as determined by AAV hSynl-RNA Barcode-Seq analysis

| | Cerebellum (Granular layer) | Cerebellum (Purkinje) | Cingulate Gyrus | Frontal Cortex | Hippocampus | Hypothalamus | Medulla | Occipital Cortex | Pons | Preoptic Area | Putamen | Thalamus |
|---|---|---|---|---|---|---|---|---|---|---|---|---|
| AAV9 | 1.00 | 1.00 | 1.00 | 1.00 | 1.00 | 1.00 | 1.00 | 1.00 | 1.00 | 1.00 | 1.00 | 1.00 |
| AAV9-N272A | 1.28 | 1.63 | 1.76 | 1.75 | 2.08 | 1.00 | 1.45 | 1.51 | 1.45 | 0.66 | 1.99 | 1.19 |
| AAV-PHP.B | 0.78 | 1.21 | 1.27 | 1.50 | 1.39 | 0.94 | 1.33 | 1.23 | 1.62 | 0.35 | 1.29 | 0.69 |
| HN1 | 1.99 | 1.78 | 2.68 | 2.18 | 4.07 | 2.05 | 1.39 | 1.54 | 1.99 | 1.99 | 2.54 | 2.84 |
| HN2 | 0.81 | 0.96 | 1.06 | 1.13 | 1.45 | 0.78 | 0.77 | 0.84 | 0.79 | 0.72 | 1.15 | 1.16 |
| HN3 | 1.75 | 2.03 | 2.14 | 2.28 | 3.54 | 1.48 | 1.87 | 1.67 | 1.71 | 1.28 | 2.20 | 1.87 |
| HN4 | 0.27 | 0.61 | 0.70 | 0.68 | 0.37 | 0.39 | 0.58 | 0.54 | 0.27 | 0.30 | 0.49 | 0.62 |
| HN5 | 0.15 | 0.27 | 0.35 | 0.22 | 0.15 | 0.01 | 0.27 | 0.17 | 0.27 | 0.22 | 0.31 | 0.15 |
| HN6 | 0.06 | 0.28 | 0.36 | 0.12 | 0.10 | 0.27 | 0.04 | 0.12 | 0.12 | 0.01 | 0.26 | 0.10 |
| HN7 | 0.96 | 1.40 | 1.44 | 1.45 | 1.64 | 1.13 | 1.48 | 1.18 | 1.01 | 0.87 | 1.39 | 1.29 |
| HN8 | 0.38 | 0.61 | 0.59 | 0.67 | 0.73 | 0.42 | 0.56 | 0.42 | 0.45 | 0.35 | 0.57 | 0.50 |
| HN9 | 1.17 | 1.45 | 1.91 | 1.66 | 2.15 | 0.92 | 1.65 | 1.30 | 1.27 | 1.10 | 1.96 | 1.48 |
| HN10 | 1.08 | 1.24 | 1.40 | 1.45 | 1.78 | 0.87 | 1.33 | 1.16 | 1.11 | 0.76 | 1.50 | 1.00 |
| HN11 | 0.96 | 1.22 | 1.37 | 1.42 | 1.62 | 1.00 | 1.28 | 1.15 | 1.12 | 0.65 | 1.41 | 1.19 |
| HN12 | 1.04 | 1.43 | 1.64 | 1.70 | 1.98 | 0.97 | 1.49 | 1.26 | 1.09 | 0.73 | 1.74 | 1.44 |
| HN13 | 1.77 | 1.74 | 1.86 | 1.82 | 2.17 | 1.20 | 2.38 | 1.54 | 1.97 | 1.36 | 2.14 | 1.77 |
| HN14 | 0.13 | 0.45 | 0.27 | 0.26 | 0.28 | 0.14 | 0.30 | 0.32 | 0.19 | 0.04 | 0.23 | 0.17 |
| HN15 | 0.38 | 0.43 | 0.19 | 0.46 | 0.44 | 0.04 | 0.28 | 0.19 | 0.23 | 0.63 | 0.36 | 0.09 |
| HN16 | 0.57 | 0.65 | 0.79 | 0.82 | 0.89 | 0.35 | 0.75 | 0.77 | 0.64 | 0.18 | 0.72 | 0.54 |
| HN17 | 0.05 | 0.18 | 0.24 | 0.14 | 0.08 | 0.28 | 0.16 | 0.11 | 0.07 | 0.01 | 0.19 | 0.03 |
| HN18 | 1.21 | 1.23 | 1.62 | 1.70 | 2.60 | 1.17 | 1.47 | 1.15 | 1.09 | 0.69 | 1.46 | 1.13 |
| HN19 | 0.24 | 0.24 | 0.21 | 0.59 | 0.50 | 0.13 | 0.14 | 0.26 | 0.26 | 0.01 | 0.31 | 0.17 |
| HN20 | 1.08 | 1.42 | 1.60 | 1.81 | 2.28 | 1.45 | 1.51 | 1.22 | 1.41 | 1.32 | 2.27 | 1.34 |
| HN21 | 0.19 | 0.11 | 0.05 | 0.15 | 0.04 | 0.49 | 0.27 | 0.19 | 0.08 | 0.01 | 0.10 | 0.14 |
| HN22 | 0.27 | 0.17 | 0.48 | 0.59 | 0.49 | 0.24 | 0.24 | 0.27 | 0.19 | 0.01 | 0.23 | 0.12 |
| HN23 | 0.60 | 1.01 | 1.21 | 1.11 | 1.55 | 0.61 | 1.23 | 0.92 | 0.95 | 0.49 | 1.25 | 0.76 |
| HN24 | 0.99 | 1.18 | 1.19 | 1.33 | 1.71 | 0.70 | 1.17 | 1.06 | 1.04 | 0.57 | 1.39 | 1.21 |

TABLE 7-continued

Transduction efficiency of hSynI-TRADE-derived AAV variants in various brain regions of one rhesus macaque following intravenous administration as determined by AAV hSynI-RNA Barcode-Seq analysis

| | Cerebellum (Granular layer) | Cerebellum (Purkinje) | Cingulate Gyrus | Frontal Cortex | Hippocampus | Hypothalamus | Medulla | Occipital Cortex | Pons | Preoptic Area | Putamen | Thalamus |
|---|---|---|---|---|---|---|---|---|---|---|---|---|
| HN25 | 0.13 | 0.14 | 0.06 | 0.32 | 0.21 | 0.12 | 0.23 | 0.24 | 0.07 | 0.01 | 0.28 | 0.08 |
| HN26 | 0.35 | 0.52 | 0.42 | 0.60 | 0.88 | 0.40 | 0.50 | 0.44 | 0.36 | 0.27 | 0.61 | 0.28 |

AAV RNA Barcode-Seq analysis was performed on RNAs extracted from various brain regions of one rhesus macaque (n = 1) intravenously injected with 2.0 × $10^{13}$ vg/kg of a DNA/RNA-barcoded dsAAV-hSynI-GFP-BCLib library that expresses RNA barcodes under the control of the hSynI enhancer-promoter. All the values are normalized with those of AAV9 (AAV9 = 1.0).

TABLE 8

Pharmacokinetic profiles of hSynI-TRADE-derived AAV variants in rhesus macaque following intravenous administration.

| | 1 m | 10 m | 30 m | 1 h | 4 h | 8 h | 24 h | 72 h |
|---|---|---|---|---|---|---|---|---|
| AAV9 | 1.00 | 1.00 | 1.00 | 1.00 | 1.00 | 1.00 | 1.00 | 1.00 |
| AAV9-N272A | 0.95 | 0.96 | 1.06 | 1.05 | 1.24 | 1.79 | 2.64 | 1.18 |
| AAV-PHP.B | 1.00 | 1.10 | 1.16 | 1.11 | 1.27 | 1.99 | 2.94 | 1.69 |
| HN1 | 0.78 | 0.66 | 0.71 | 0.65 | 0.67 | 0.88 | 0.65 | 0.30 |
| HN2 | 0.69 | 0.72 | 0.69 | 0.62 | 0.75 | 0.92 | 1.24 | 0.25 |
| HN3 | 0.85 | 0.86 | 0.96 | 0.77 | 1.12 | 1.70 | 2.60 | 0.60 |
| HN4 | 1.07 | 1.07 | 1.15 | 1.15 | 1.30 | 1.88 | 3.39 | 2.15 |
| HN5 | 0.99 | 0.98 | 1.14 | 1.06 | 1.19 | 1.62 | 2.83 | 1.39 |
| HN6 | 1.13 | 1.09 | 1.18 | 1.09 | 1.32 | 1.97 | 3.32 | 1.90 |
| HN7 | 0.75 | 0.78 | 0.81 | 0.79 | 0.95 | 1.33 | 1.78 | 0.27 |
| HN8 | 1.05 | 1.06 | 1.02 | 1.07 | 1.27 | 1.82 | 3.02 | 1.67 |
| HN9 | 0.83 | 0.76 | 0.87 | 0.78 | 0.92 | 1.36 | 1.91 | 0.29 |
| HN10 | 0.84 | 0.87 | 0.90 | 0.87 | 1.14 | 1.32 | 2.32 | 0.28 |
| HN11 | 0.88 | 0.89 | 0.90 | 0.86 | 1.20 | 1.55 | 2.42 | 0.61 |
| HN12 | 0.81 | 0.80 | 0.86 | 0.80 | 0.99 | 1.41 | 1.90 | 0.27 |
| HN13 | 0.76 | 0.71 | 0.82 | 0.76 | 0.90 | 1.31 | 1.86 | 0.29 |
| HN14 | 0.76 | 0.75 | 0.83 | 0.78 | 0.99 | 1.40 | 2.21 | 0.18 |
| HN15 | 1.31 | 1.07 | 1.27 | 1.23 | 1.36 | 2.37 | 4.46 | 2.03 |
| HN16 | 0.76 | 0.80 | 0.91 | 0.84 | 0.98 | 1.41 | 1.90 | 0.26 |
| HN17 | 1.02 | 1.07 | 1.21 | 1.00 | 1.29 | 1.88 | 2.91 | 1.84 |
| HN18 | 0.88 | 0.88 | 0.96 | 0.90 | 1.10 | 1.57 | 2.44 | 0.58 |
| HN19 | 1.08 | 1.04 | 1.15 | 1.14 | 1.26 | 2.04 | 3.69 | 2.05 |
| HN20 | 0.89 | 0.82 | 0.88 | 0.81 | 0.91 | 1.62 | 2.28 | 0.39 |
| HN21 | 1.00 | 1.00 | 1.11 | 0.98 | 1.20 | 1.54 | 2.41 | 2.10 |
| HN22 | 0.96 | 0.97 | 1.09 | 1.03 | 1.24 | 1.74 | 2.90 | 1.82 |
| HN23 | 0.76 | 0.76 | 0.86 | 0.80 | 0.97 | 1.50 | 2.14 | 0.35 |
| HN24 | 0.93 | 1.00 | 0.96 | 1.00 | 1.41 | 1.48 | 2.31 | 1.41 |
| HN25 | 1.05 | 1.16 | 1.08 | 1.19 | 1.18 | 2.00 | 3.52 | 1.54 |
| HN26 | 1.03 | 0.98 | 1.08 | 1.07 | 1.18 | 1.77 | 2.72 | 1.56 |

AAV DNA Barcode-Seq analysis was performed on the blood samples obtained from a single rhesus macaque injected with 2 × $10^{13}$ vg/kg of the DNA/RNA-barcoded dsAAV-hSynI-GFP-BCLib library (the same animal as in Table 7). All the values are normalized with those of AAV9 (AAV9 = 1.0).

TABLE 9

Biodistribution of hSynI-TRADE-derived AAV variants to peripheral tissues of a rhesus macaque following intravenous administration as determined by AAV DNA Barcode-Seq analysis

| | Liver | Heart | Lung | Kidney | Pancreas | Spleen | Gastrocnemius muscle | Soleus muscle | Intestine | Bone marrow | Smooth muscle (Stomach) |
|---|---|---|---|---|---|---|---|---|---|---|---|
| AAV9 | 1.00 | 1.00 | 1.00 | 1.00 | 1.00 | 1.00 | 1.00 | 1.00 | 1.00 | 1.00 | 1.00 |
| AAV9-N272A | 0.07 | 0.20 | 0.79 | 1.29 | 2.91 | 4.67 | 0.26 | 0.50 | 0.64 | 0.06 | 0.82 |
| AAV-PHP.B | 0.35 | 0.42 | 1.09 | 1.22 | 2.55 | 2.14 | 0.54 | 0.77 | 0.40 | 0.43 | 0.80 |
| HN1 | 0.26 | 0.41 | 0.34 | 0.41 | 0.35 | 0.76 | 1.04 | 1.12 | 0.24 | 0.33 | 0.33 |
| HN2 | 0.16 | 0.17 | 0.35 | 0.32 | 0.51 | 0.71 | 0.32 | 0.52 | 0.11 | 0.07 | 0.30 |
| HN3 | 0.12 | 0.21 | 0.78 | 0.91 | 2.19 | 2.48 | 0.25 | 0.58 | 0.18 | 0.05 | 0.63 |
| HN4 | 0.02 | 0.08 | 0.78 | 1.12 | 2.25 | 3.42 | 0.17 | 0.41 | 0.15 | 0.03 | 0.39 |
| HN5 | 0.01 | 0.05 | 0.73 | 0.98 | 2.24 | 2.85 | 0.10 | 0.30 | 0.07 | 0.01 | 0.37 |
| HN6 | 0.01 | 0.05 | 0.92 | 1.11 | 2.15 | 3.50 | 0.11 | 0.40 | 0.12 | 0.01 | 0.30 |
| HN7 | 0.27 | 0.19 | 0.36 | 0.43 | 0.47 | 0.51 | 0.18 | 0.23 | 0.16 | 0.12 | 0.37 |
| HN8 | 0.04 | 0.08 | 0.71 | 0.98 | 2.28 | 2.57 | 0.12 | 0.38 | 0.11 | 0.02 | 0.44 |
| HN9 | 0.12 | 0.13 | 0.32 | 0.36 | 0.71 | 0.79 | 0.13 | 0.31 | 0.11 | 0.04 | 0.29 |

TABLE 9-continued

Biodistribution of hSynI-TRADE-derived AAV variants to peripheral tissues of a rhesus macaque following intravenous administration as determined by AAV DNA Barcode-Seq analysis

| | Liver | Heart | Lung | Kidney | Pancreas | Spleen | Gastrocnemius muscle | Soleus muscle | Intestine | Bone marrow | Smooth muscle (Stomach) |
|---|---|---|---|---|---|---|---|---|---|---|---|
| HN10 | 0.08 | 0.13 | 0.63 | 0.63 | 1.39 | 2.53 | 0.16 | 0.38 | 0.11 | 0.02 | 0.28 |
| HN11 | 0.06 | 0.16 | 0.63 | 0.74 | 1.62 | 1.68 | 0.18 | 0.44 | 0.16 | 0.03 | 0.47 |
| HN12 | 0.19 | 0.11 | 0.28 | 0.38 | 0.56 | 0.61 | 0.10 | 0.19 | 0.09 | 0.05 | 0.30 |
| HN13 | 0.18 | 0.23 | 0.58 | 0.44 | 0.88 | 1.12 | 0.21 | 0.38 | 0.18 | 0.06 | 0.49 |
| HN14 | 0.00 | 0.04 | 0.30 | 0.49 | 0.59 | 0.83 | 0.06 | 0.28 | 0.05 | 0.01 | 0.34 |
| HN15 | 0.01 | 0.06 | 1.01 | 1.43 | 2.43 | 3.80 | 0.13 | 0.46 | 0.10 | 0.02 | 0.69 |
| HN16 | 0.02 | 0.07 | 0.37 | 1.00 | 0.70 | 0.87 | 0.08 | 0.17 | 0.06 | 0.02 | 0.28 |
| HN17 | 0.01 | 0.04 | 0.85 | 1.01 | 2.38 | 3.25 | 0.08 | 0.29 | 0.10 | 0.01 | 0.32 |
| HN18 | 0.15 | 0.13 | 0.36 | 0.52 | 0.90 | 1.17 | 0.13 | 0.31 | 0.09 | 0.01 | 0.33 |
| HN19 | 0.06 | 0.08 | 0.93 | 1.14 | 2.98 | 3.41 | 0.15 | 0.42 | 0.10 | 0.02 | 0.36 |
| HN20 | 0.36 | 0.22 | 0.34 | 0.50 | 0.88 | 0.96 | 0.21 | 0.48 | 0.14 | 0.05 | 0.31 |
| HN21 | 0.02 | 0.05 | 0.74 | 1.03 | 2.17 | 3.08 | 0.12 | 0.33 | 0.06 | 0.01 | 0.57 |
| HN22 | 0.06 | 0.07 | 0.72 | 0.89 | 1.73 | 2.68 | 0.14 | 0.31 | 0.09 | 0.02 | 0.25 |
| HN23 | 0.04 | 0.08 | 0.61 | 0.28 | 0.74 | 0.71 | 0.09 | 0.30 | 0.10 | 0.01 | 0.24 |
| HN24 | 0.06 | 0.14 | 0.66 | 0.74 | 1.99 | 1.98 | 0.18 | 0.43 | 0.13 | 0.03 | 0.50 |
| HN25 | 0.06 | 0.07 | 0.90 | 1.21 | 2.76 | 3.28 | 0.22 | 0.43 | 0.10 | 0.03 | 0.56 |
| HN26 | 0.17 | 0.10 | 0.64 | 0.90 | 1.84 | 2.38 | 0.12 | 0.35 | 0.12 | 0.02 | 0.56 |

AAV DNA Barcode-Seq analysis was performed on DNA extracted from various peripheral tissues of one rhesus macaque (n = 1, the same animal as presented in Table 7) intravenously injected with 2 × 10$^{13}$ vg/kg of a DNA/RNA-barcoded dsAAV-hSynI-GFP-BCLib library. All values are normalized to AAV9 (AAV9 = 1.0).

TABLE 9

Splice donor and splice acceptor sites identified in antisense AAV cap ORF transcripts.

| SEQ ID | AAV serotype | SD or SA | Exon-intron junction sequence (Introns are underlined) |
|---|---|---|---|
| SEQ ID NO: 199 | AAV1 | SD | 1009-CTTAC CAGCA-1018 |
| SEQ ID NO: 199 | AAV3 | SD | 1006-CTTAC CAGCA-1015 |
| SEQ ID NO: 200 | AAV1 | SD | 1228-TTTAC CTTCA-1237 |
| SEQ ID NO: 201 | AAV3 | SD | 1237-TATAC CTTCG-1246 |
| SEQ ID NO: 202 | AAV1 | SD | 1331-ATTAC CTGAA-1340 |
| SEQ ID NO: 203 | AAV1 | SD | 1434-GCTAC CTGGA-1443 |
| SEQ ID NO: 204 | AAV1 | SD | 1502-TTTAC CTGGA-1510 |
| SEQ ID NO: 205 | AAV1 | SD | 1803-ATTAC CTGGC-1812 |
| SEQ ID NO: 206 | AAV3 | SD | 1803-CTTAC CTGGC-1812 |
| SEQ ID NO: 207 | AAV1 | SD | 1835-TGTAC CTGCA-1844 |
| SEQ ID NO: 208 | AAV1 | SD | 2189-GTTAC CTTAC-2198 |
| SEQ ID NO: 209 | AAV9 | SD | 2189-GATAC CTGAC-2198 |
| SEQ ID NO: 210 | AAV1 | SD | 2194-CTTAC CCGTC-2203 |
| SEQ ID NO: 211 | AAV3 | SD | 2194-CTCAC ACGAA-2203 |
| SEQ ID NO: 212 | AAV1 | SA | 305-AGCGT CTGCA-314 |
| SEQ ID NO: 213 | AAV1 | SA | 414-GGCTC CTGGA-423 |
| SEQ ID NO: 213 | AAV3 | SA | 414-GGCTC CTGGA-423 |
| SEQ ID NO: 214 | AAV1 | SA | 495-GCCCG CTAAA-504 |
| SEQ ID NO: 214 | AAV9 | SA | 495-GCCCG CTAAA-504 |
| SEQ ID NO: 215 | AAV3 | SA | 1133-TCACC CTGAA-1142 |
| SEQ ID NO: 216 | AAV1 | SA | 1181-ACTGC CTGGA-1190 |
| SEQ ID NO: 202 | AAV1 | SA | 1331-ATTAC CTGAA-1340 |
| SEQ ID NO: 217 | AAV3 | SA | 1328-ACTAC CTGAA-1337 |
| SEQ ID NO: 218 | AAV1 | SA | 1464-CGTTT CTAAA-1473 |
| SEQ ID NO: 219 | AAV1 | SA | 1653-AAACA CTGCA-1662 |
| SEQ ID NO: 220 | AAV1 | SA | 2054-GGGAG CTGCA-2063 |
| SEQ ID NO: 463 | AAV3 | SA | 2054-GGGAGCTACA-2063 |

Ten nucleotides around exon-intron junctions identified in antisense AAV cap mRNA are presented with the junction at the center. Letters with underlines represent intron sequences. Letters with no underline represent exon sequences. Numbers indicate nucleotide positions of the AAV cap ORF. SD, splice donor; SA, splice acceptor. Please note that SEQ ID NO: 199 of AAV1 and SEQ ID NO: 199 of AAV3 are corresponding to each other in sequence alignment. Likewise, SEQ ID NO: 213 of AAV1 and SEQ ID NO: 213 of AAV3 are corresponding to each other in sequence alignment.

In the course of the experiment, when the AAV9 cap gene ORF was expressed in an antisense orientation in HEK293 cells or Neuro2a cells, the majority of the antisense AAV9 cap gene mRNA-derived RT-PCR products were truncated by approximately 1.7 kb (FIG. 4), although this was not the case with the RNA recovered from the AAV-PHP.B-hSynI-GFP-TRADE-transduced mouse brain tissue (FIG. 3C, FIG. 3D). Sequencing of the truncated RT-PCR products revealed that a 1694 bp-long region was missing within the AAV9 cap ORF (FIG. 5). Without being bound by any particular theory, it appears that the truncation results from a splicing event, based on the observation that we could identify splice donor and acceptor sites in the PCR products that have the common features of exon-intron junctions. Intriguingly, a sequence alignment study revealed that the cryptic splice donor and acceptor sites with the common features of exon-intron junctions can also be identified in many naturally occurring AAV serotypes at the regions corresponding to the splice donor and acceptor sites identified in the AAV9 cap gene and they are highly conserved (FIGS. 6A-6F). This indicates that splicing could potentially take place in the cap ORF-derived antisense mRNA of not only AAV9 but also many other AAV strains. To date, we have found that splicing occurs on the AAV3 cap ORF-derived antisense mRNA when it is expressed under the control of a human liver-specific promoter (LSP) in HepG2 cells. Although full characterization has not yet been completed, a preliminary RT-PCR using an antisense mRNA-specific RT primer yielded truncated RT-PCR products in addition to the full-length, non-spliced product. The sequencing analysis of two truncated RT-PCR products revealed that there were multiple splicing events on the antisense mRNA (FIGS. 7A-7B). A sequencing alignment study has identified additional potential splice donor and acceptor sites (FIGS. 8A-8F and FIGS. 9A-9C). We also found splicing events in the antisense mRNA derived from the AAV1 cap ORF when antisense mRNA was transcribed by the hSynI enhancer-promoter in HEK293 cells or Neuro2a cells (FIG. 10). Many of the identified splice donor sites (GT/CA) and splice acceptor sites (AG/TC) are highly conserved across different serotypes, indicating the possibility that these sites are also utilized as splicing donor and acceptor sites in the AAV serotypes that have yet to be investigated. Indeed, we have found that splicing of antisense mRNA transcripts of the AAV1, AAV3 and AAV9 cap ORFs uses several common splice donor and acceptor sites (FIG. 10). To date, we have not yet observed splicing of antisense mRNA transcripts of the AAV5 cap ORF. For serotypes other than AAV1, 3, 5 and 9, splicing events in antisense mRNA of the AAV cap ORFs have not yet been investigated.

Potential splicing of the cap ORF-derived antisense mRNA is scientifically intriguing, but may hinder the TRADE system when the full-length cap ORF sequence needs to be recovered from antisense mRNA. To overcome this potential issue, we introduced silent mutations that presumably disrupt the conserved sequences at exon-intron junctions and branching points. To demonstrate proof of principle of this approach, we introduced silent mutations into the AAV9 cap ORF contained in the plasmid, pAAV9-N272A-PHP.B-hSyn1-GFP-TRADE, that disrupt the splice acceptor (SA) consensus sequence (pAAV9NS1 construct), the splice donor (SD) consensus sequence (pAAV9NS2 construct), and both the splice acceptor and donor consensus sequences (pAAV9NS3 construct). Please note that NS stands for "non-spliced." The method we use to disrupt these consensus sequences is described below.

We codon-optimize the AAV cap ORF sequence for human cell expression.

To identify potential splice donor and acceptor sites on antisense mRNA derived from the cap ORFs, we develop and use our proprietary database of potential splice donor and acceptor sites on antisense mRNA based on our experimental and bioinformatics observations (i.e., FIGS. 5, 6A-6F, 7A-7B, 8A-8F, 9A-9C and 10).

We destroy the GT (splice donor) and/or AG (splice acceptor) consensus sequence by changing at least one nucleotide using the codon-optimized sequence. If the codon-optimized sequence is not applicable, we use an alternative nucleotide(s) that can destroy the consensus sequence.

We remove a stretch of T's upstream of the splice acceptor sites by introducing silence mutations based on the codon-optimized sequence. If the codon-optimized sequence is not sufficient to destroy a stretch of T's, we use alternative nucleotides.

We also avoid G at the exon termini as much as possible.

Using several programs that can predict branching points (e.g., Human Splicing Finder (Desmet, Hamroun et al. 2009)), we identify potential branching points and replace them with the codon-optimized sequence. If the degree of nucleotide changes attainable by this method is not sufficient, we introduce alternative nucleotides to disrupt potential branching points.

With this method, we have created AAV9NS1 (SA, destroyed), AAV9NS2 (SD, destroyed) and AAV9NS3 (both SD and SA, destroyed) cap ORFs (FIGS. 9A-9C). We expressed these ORFs in an antisense orientation under the control of the hSynI enhancer-promoter in Neuro2a cells by transient plasmid transfection, and analyzed the antisense transcripts by RT-PCR. This experiment revealed that the splicing could be effectively suppressed in all of the NS1, NS2 and NS3 cap ORFs (FIG. 10). It should be noted that even if splicing takes place on the cap ORF-derived antisense mRNA, it would still be possible to recover the relatively small peptide insertion region of the cap ORF by RT-PCR from pre-mRNA.

The TRADE method described herein uses antisense mRNA for viral protein evolution to establish the proof-of-principle and to show successful reduction of the method to practice. The TRADE system can also utilize mRNA in a sense orientation as long as the viruses can be produced and potential expression of viral proteins in target cells during the directed evolution procedure does not hinder successful evolution of novel capsids.

What is claimed is:

1. A nucleic acid molecule comprising an adeno-associated virus (AAV) cap gene sequence in an antisense orientation, wherein the AAV cap gene sequence in the antisense orientation comprises a messenger ribonucleic acid (mRNA) splicing suppression mutation.

2. The nucleic acid molecule of claim 1, wherein the nucleic acid molecule further comprises a regulatory sequence.

3. The nucleic acid molecule of claim 2, wherein the regulatory sequence drives expression of the AAV cap gene sequence in the antisense orientation.

4. The nucleic acid molecule of claim 3, wherein the regulatory sequence is a promoter sequence.

5. The nucleic acid molecule of claim 4, wherein the promoter is a cell type-specific promoter, a tissue-specific promoter, or a ubiquitous promoter.

6. The nucleic acid molecule of claim 1, wherein the AAV cap gene sequence is a wild-type AAV cap gene sequence.

7. The nucleic acid molecule of claim 1, wherein the AAV cap gene sequence is an AAV1, AAV2, AAV3, AAV4, AAV5, AAV6, AAV7, AAV8, AAV9, AAV10, AAV11, AAV12, AAV13, or other natural AAV isolate cap gene sequence.

8. The nucleic acid molecule of claim 1, wherein the AAV cap gene sequence is an engineered AAV cap gene sequence.

9. The nucleic acid molecule of claim 1, wherein the AAV cap gene sequence is one of a library of diverse AAV cap gene sequences.

10. The nucleic acid molecule of claim 1, wherein the messenger ribonucleic acid (mRNA) splicing suppression mutation comprises a mutation within an exon-intron junction, wherein the exon-intron junction comprises a sequence as set forth in any one of SEQ ID NOs: 199-220 or 463.

11. The nucleic acid molecule of claim 1, wherein the AAV cap gene sequence in the antisense orientation comprises two or more messenger ribonucleic acid (mRNA) splicing suppression mutations.

12. A nucleic acid molecule comprising:
(a) a first nucleic acid sequence comprising a first regulatory sequence and an adeno-associated virus (AAV) cap gene sequence in a sense orientation;
(b) a second nucleic acid sequence comprising a second regulatory sequence and the AAV cap gene sequence in an antisense orientation, wherein the AAV cap gene sequence in the antisense orientation comprises a messenger ribonucleic acid (mRNA) splicing suppression mutation.

13. The nucleic acid molecule of claim 12, wherein the second regulatory sequence drives expression of an antisense transcript.

14. The nucleic acid molecule of claim 12, wherein the second regulatory sequence is a cell type-specific promoter, a tissue-specific promoter, or a ubiquitous promoter.

15. The nucleic acid molecule of claim of claim 13, wherein the first regulatory sequence drives expression of the AAV cap gene sequence in the sense orientation.

16. The nucleic acid molecule of claim 12, wherein the AAV cap gene sequence is an AAV1, AAV2, AAV3, AAV4, AAV5, AAV6, AAV7, AAV8, AAV9, AAV10, AAV11, AAV12, AAV13, or other natural AAV isolate cap gene sequence.

17. The nucleic acid molecule of claim 12, wherein the AAV cap gene sequence is an engineered AAV cap gene sequence.

18. The nucleic acid molecule of claim 12, wherein the AAV cap gene sequence is one of a library of diverse AAV cap gene sequences.

19. The nucleic acid molecule of claim 12, wherein the messenger ribonucleic acid (mRNA) splicing suppression mutation comprises a mutation within an exon-intron junction, wherein the exon-intron junction comprises a sequence as set forth in any one of SEQ ID NOs: 199-220 or 463.

20. The nucleic acid molecule of claim 12, wherein the AAV cap gene sequence in the antisense orientation comprises two or more messenger ribonucleic acid (mRNA) splicing suppression mutations.

* * * * *

SEQUENCE LISTING

```
<160> NUMBER OF SEQ ID NOS: 463

<210> SEQ ID NO 1
<211> LENGTH: 45
<212> TYPE: DNA
<213> ORGANISM: Artificial Sequence
<220> FEATURE:
<223> OTHER INFORMATION: synthesized
<220> FEATURE:
<221> NAME/KEY: Intron
<222> LOCATION: (1)..(27)

<400> SEQUENCE: 1 gaacccgcc ccattggcac gcgttacctg actcgtaatc tgtaa            45
```

```
<210> SEQ ID NO 2
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: PEPTIDE
<222> LOCATION: (5)..(12)
<223> OTHER INFORMATION: any amino acid

<400> SEQUENCE: 2

Gly Gly Gly Ser Xaa Xaa Xaa Xaa Xaa Xaa Xaa Xaa Gly Gly Gly Gly
1               5                   10                  15

Ser

<210> SEQ ID NO 3
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 3

Ala Asp Lys Pro Pro Gly Leu Ser
1               5

<210> SEQ ID NO 4
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 4

Ala Gly Glu Asp Gly Ser Ser Arg
1               5

<210> SEQ ID NO 5
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 5

Ala Leu Gly Thr Ala Thr Gln Arg
1               5

<210> SEQ ID NO 6
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 6
```

```
Ala Leu Asn Thr Ala Leu Val Glu
1               5

<210> SEQ ID NO 7
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 7

Ala Met Val Arg Leu Thr His Asn
1               5

<210> SEQ ID NO 8
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 8

Ala Ser Arg Asp Pro Ser Ala Thr
1               5

<210> SEQ ID NO 9
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 9

Asp Ala Asn Asp Ala Arg Gln Arg
1               5

<210> SEQ ID NO 10
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 10

Asp Leu Ala Arg Met Ala Ala Ala
1               5

<210> SEQ ID NO 11
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 11
```

```
Asp Gln Gly Ser Ile Thr Ala His
1               5

<210> SEQ ID NO 12
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 12

Asp Arg Thr Pro Gly Val Asn Val
1               5

<210> SEQ ID NO 13
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 13

Asp Thr Asp Thr Leu Ser Pro Gly
1               5

<210> SEQ ID NO 14
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 14

Glu Glu Asp Ala Gln Leu Leu Ile
1               5

<210> SEQ ID NO 15
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 15

Glu Lys Leu Asn Asp Trp Pro Thr
1               5

<210> SEQ ID NO 16
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)
```

```
<400> SEQUENCE: 16

Glu Leu Asn Ser Ala Arg Gln Val
1               5

<210> SEQ ID NO 17
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 17

Glu Leu Gln Ser Phe Ala Gly Leu
1               5

<210> SEQ ID NO 18
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 18

Glu Asn Lys Ser Ala Pro Leu Pro
1               5

<210> SEQ ID NO 19
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 19

Glu Arg Thr Ala Val Lys Gly Asn
1               5

<210> SEQ ID NO 20
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 20

Gly Gly Ile Gln Thr Val Val Thr
1               5

<210> SEQ ID NO 21
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)
```

```
<400> SEQUENCE: 21

Gly Gly Ser Pro Leu Ala His Pro
1               5

<210> SEQ ID NO 22
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 22

Gly Gly Thr Ala Ala Gln Gly Val
1               5

<210> SEQ ID NO 23
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 23

Gly Lys Met Ala Ser Gly Ser Leu
1               5

<210> SEQ ID NO 24
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 24

Gly Lys Gln Pro Val Gln Pro Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 25

Gly Asn Pro His Thr Gly Ser Thr
1               5

<210> SEQ ID NO 26
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
```

```
<222> LOCATION: (1)..(8)

<400> SEQUENCE: 26

Gly Pro Thr Leu Gly Gly Ser Gly
1               5

<210> SEQ ID NO 27
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 27

Gly Gln Arg Gly Leu Pro Ile Ala
1               5

<210> SEQ ID NO 28
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 28

Gly Arg Glu Pro Arg Arg Leu His
1               5

<210> SEQ ID NO 29
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 29

Gly Thr Pro Gln Thr Thr Lys Glu
1               5

<210> SEQ ID NO 30
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 30

Gly Val Thr Glu Arg Pro Asn Arg
1               5

<210> SEQ ID NO 31
<211> LENGTH: 8
<212> TYPE: PRT
<213> ORGANISM: Artificial Sequence
<220> FEATURE:
<223> OTHER INFORMATION: peptide
<220> FEATURE:
```

```
<221> NAME/KEY: PEPTIDE
<222> LOCATION: (1)..(8)

<400> SEQUENCE: 31

His Leu Gly Asp Asn Leu Ala Arg
1               5

<210> SEQ ID NO 32
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 32

His Pro Gly Ser Gly Ala Gly Pro
1               5

<210> SEQ ID NO 33
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 33

His Gln Val Thr Ser Ser Gly Ala
1               5

<210> SEQ ID NO 34
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 34

His Val Gly Ser Gln Met His Ala
1               5

<210> SEQ ID NO 35
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)
<220> FEATURE:
<221> NAME/KEY: UNSURE
<222> LOCATION: (3)..(3)

<400> SEQUENCE: 35

Ile Gly Xaa Thr Val Pro Met Gln
1               5

<210> SEQ ID NO 36
<211> LENGTH: 8
<212> TYPE: PRT
```

```
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 36

Lys Phe Thr Arg Asp Gly Pro Tyr
1               5

<210> SEQ ID NO 37
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 37

Lys Gly Pro Ala Glu Gln Gly His
1               5

<210> SEQ ID NO 38
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 38

Leu Ala His Ser Pro Arg Leu Trp
1               5

<210> SEQ ID NO 39
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 39

Leu Glu Arg Asn Arg Asp Ser Asp
1               5

<210> SEQ ID NO 40
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 40

Leu Glu Thr His Thr Ser Leu Thr
1               5

<210> SEQ ID NO 41
<211> LENGTH: 8
```

```
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 41

Leu His Asp Gly Lys Tyr Ser Thr
1               5

<210> SEQ ID NO 42
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 42

Leu Lys Ala Thr Gly Arg Gly Lys
1               5

<210> SEQ ID NO 43
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 43

Leu Leu Pro Gly Ser Ala Asp Gly
1               5

<210> SEQ ID NO 44
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 44

Leu Leu Val Thr Ala Arg Ser His
1               5

<210> SEQ ID NO 45
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 45

Leu Pro Glu Val Glu Pro Thr Asn
1               5

<210> SEQ ID NO 46
```

```
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 46

Leu Pro Trp Glu Asn Ser Ser Gln
1               5

<210> SEQ ID NO 47
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 47

Leu Gln Arg Asn Ser Asp Ala Asn
1               5

<210> SEQ ID NO 48
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 48

Leu Gln Ser Ala Pro Arg Ala Thr
1               5

<210> SEQ ID NO 49
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 49

Met Leu Gly Ser Gln Val Pro Thr
1               5

<210> SEQ ID NO 50
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 50

Met Ser Gly Gln Gly Tyr Gln Ala
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 51

Asn Pro Gly Arg Asp Phe Arg Asp
1               5

<210> SEQ ID NO 52
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 52

Asn Gln Pro Ser Asp Tyr Val Ser
1               5

<210> SEQ ID NO 53
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 53

Asn Ser Val Gly Ser Ala Asp Lys
1               5

<210> SEQ ID NO 54
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 54

Asn Val Gln Arg Thr Gln Arg Gly
1               5

<210> SEQ ID NO 55
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 55

Pro Ala Gln Leu Asn Gly Pro Arg
1               5
```

```
<210> SEQ ID NO 56
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 56

Pro Glu Arg Glu Arg Leu Pro Arg
1               5

<210> SEQ ID NO 57
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 57

Pro Gly Asn Gly Ser His Thr Met
1               5

<210> SEQ ID NO 58
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 58

Pro Ile Pro Gly Thr Pro Gln Pro
1               5

<210> SEQ ID NO 59
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 59

Pro Met Ser Val Pro Ala Ser Asn
1               5

<210> SEQ ID NO 60
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 60

Pro Arg Pro Thr Val Val Gly Thr
1               5
```

```
<210> SEQ ID NO 61
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 61

Pro Arg Thr Asn Arg Gly Pro Glu
1               5

<210> SEQ ID NO 62
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 62

Pro Val Ala Asn Pro Thr Thr Ala
1               5

<210> SEQ ID NO 63
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 63

Pro Val Leu Gly Gly Pro Pro Lys
1               5

<210> SEQ ID NO 64
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 64

Gln Gly Ser Arg Gln Gly Ser Ser
1               5

<210> SEQ ID NO 65
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 65

Gln Met Ala Glu Thr Pro Ile Ser
```

```
<210> SEQ ID NO 66
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 66

Gln Met Leu Gly Ile Gly Arg Ser
1               5

<210> SEQ ID NO 67
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 67

Gln Ser Gly Asp Ser Ala Leu Asn
1               5

<210> SEQ ID NO 68
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 68

Arg Ala Gly Leu Thr Ser Ser Glu
1               5

<210> SEQ ID NO 69
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 69

Arg Leu Asp Asn Thr Gly Val Gly
1               5

<210> SEQ ID NO 70
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 70
```

```
Arg Met Pro Gly Lys Pro Tyr Ser
1               5

<210> SEQ ID NO 71
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 71

Arg Val Ala Gly Ala Ser Gln Pro
1               5

<210> SEQ ID NO 72
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 72

Arg Val Glu Ser Ser Gln Leu Glu
1               5

<210> SEQ ID NO 73
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 73

Ser Ala Arg Thr Gly Ala Ser Glu
1               5

<210> SEQ ID NO 74
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 74

Ser Glu Arg Asn Arg Ala Ser Met
1               5

<210> SEQ ID NO 75
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 75
```

Ser Ile Asp Val Arg Met Ala Ala
1               5

<210> SEQ ID NO 76
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 76

Ser Arg Asp Gly His Ile Leu Arg
1               5

<210> SEQ ID NO 77
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 77

Ser Arg Gln Val Val Leu Pro Gly
1               5

<210> SEQ ID NO 78
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 78

Ser Ser Arg Gly Tyr Thr Ser Thr
1               5

<210> SEQ ID NO 79
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 79

Ser Ser Val Val Ser Gln Gly Pro
1               5

<210> SEQ ID NO 80
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

```
<400> SEQUENCE: 80

Ser Val Ala Glu Ser Gly Arg Glu
1               5

<210> SEQ ID NO 81
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 81

Thr Ala Leu Thr Ala Asn Thr Gln
1               5

<210> SEQ ID NO 82
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 82

Thr Glu Ser Ser Val Gly Asn Leu
1               5

<210> SEQ ID NO 83
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 83

Thr Gly Arg Glu Gly Ala Asn Leu
1               5

<210> SEQ ID NO 84
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 84

Thr Leu Ser Glu Pro Pro Lys Lys
1               5

<210> SEQ ID NO 85
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)
```

```
<400> SEQUENCE: 85

Thr Asn Ala Val Ser Gly Lys Ser
1               5

<210> SEQ ID NO 86
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 86

Thr Arg Ala Pro Thr Ile His Leu
1               5

<210> SEQ ID NO 87
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 87

Thr Arg Glu Ser Thr Asp Arg Gly
1               5

<210> SEQ ID NO 88
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 88

Thr Val Ala Ala Ala Pro Asn Leu
1               5

<210> SEQ ID NO 89
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 89

Thr Tyr His Asn Asn Thr Pro Arg
1               5

<210> SEQ ID NO 90
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
```

<222> LOCATION: (1)..(8)

<400> SEQUENCE: 90

Val Ser Asn Ser Thr Arg Thr Ser
1               5

<210> SEQ ID NO 91
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 91

Val Thr Leu Gln Ile Asp Thr Lys
1               5

<210> SEQ ID NO 92
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 92

Trp Met Ser Arg Pro Gly Pro Thr
1               5

<210> SEQ ID NO 93
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 93

Trp Pro Tyr Arg Gly Leu Thr Gln
1               5

<210> SEQ ID NO 94
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 94

Trp Arg Arg Gln Gly Ser Arg Ala
1               5

<210> SEQ ID NO 95
<211> LENGTH: 8
<212> TYPE: PRT
<213> ORGANISM: Artificial Sequence
<220> FEATURE:
<223> OTHER INFORMATION: peptide
<220> FEATURE:

```
<221> NAME/KEY: PEPTIDE
<222> LOCATION: (1)..(8)

<400> SEQUENCE: 95

Tyr Ala Gln Arg Phe Ala Lys Met
1               5

<210> SEQ ID NO 96
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 96

Tyr Asn Ser Pro Arg Gln Thr Val
1               5

<210> SEQ ID NO 97
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 97

Ala Pro Thr Asn Phe Ala His Pro
1               5

<210> SEQ ID NO 98
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 98

Ala Gln Thr Asn Leu Ala Ala Gly
1               5

<210> SEQ ID NO 99
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 99

Ala Ser Leu Pro Asn Leu Gly Gln
1               5

<210> SEQ ID NO 100
<211> LENGTH: 8
<212> TYPE: PRT
<213> ORGANISM: Artificial Sequence
<220> FEATURE:
<223> OTHER INFORMATION: peptide
```

```
<220> FEATURE:
<221> NAME/KEY: PEPTIDE
<222> LOCATION: (1)..(8)

<400> SEQUENCE: 100

Asp Tyr Met His Asn Thr Gly Leu
1               5

<210> SEQ ID NO 101
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 101

Asp Tyr Met His Thr Thr Gly Leu
1               5

<210> SEQ ID NO 102
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 102

Glu Arg Asn Ala Trp His Ala Gly
1               5

<210> SEQ ID NO 103
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 103

Glu Thr Gln Ala Thr Pro Met Pro
1               5

<210> SEQ ID NO 104
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 104

Glu Trp Glu Asp Ser Ala Arg Ser
1               5

<210> SEQ ID NO 105
<211> LENGTH: 8
<212> TYPE: PRT
<213> ORGANISM: Artificial Sequence
<220> FEATURE:
```

```
<223> OTHER INFORMATION: peptide
<220> FEATURE:
<221> NAME/KEY: PEPTIDE
<222> LOCATION: (1)..(8)

<400> SEQUENCE: 105

Phe Thr Gly Asp Thr Asp Thr Leu
1               5

<210> SEQ ID NO 106
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 106

Phe Thr Asn Arg Thr Ser Thr Thr
1               5

<210> SEQ ID NO 107
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 107

Gly Asp Tyr Thr Val Gln Arg Pro
1               5

<210> SEQ ID NO 108
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 108

Gly Gly Leu Arg Thr Asp Tyr Gly
1               5

<210> SEQ ID NO 109
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 109

Gly Pro Gln Glu Gly Ser Glu Arg
1               5

<210> SEQ ID NO 110
<211> LENGTH: 8
<212> TYPE: PRT
<213> ORGANISM: Artificial Sequence
```

```
<220> FEATURE:
<223> OTHER INFORMATION: peptide
<220> FEATURE:
<221> NAME/KEY: PEPTIDE
<222> LOCATION: (1)..(8)

<400> SEQUENCE: 110

Gly Ser Asn His Thr Gln Ser Leu
1               5

<210> SEQ ID NO 111
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 111

His Asp Arg Asp Thr Arg Gln Ala
1               5

<210> SEQ ID NO 112
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 112

Leu Asp Gln Asn Arg Arg Pro Gln
1               5

<210> SEQ ID NO 113
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 113

Leu Glu Gln Gln Arg Gly Ala Ser
1               5

<210> SEQ ID NO 114
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 114

Leu Gly Gly Asn Ala Gln Gly Leu
1               5

<210> SEQ ID NO 115
<211> LENGTH: 8
<212> TYPE: PRT
```

```
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 115

Leu Leu Val Thr Thr Arg Ser His
1               5

<210> SEQ ID NO 116
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(7)

<400> SEQUENCE: 116

Leu Val Thr Asn Thr Thr Arg
1               5

<210> SEQ ID NO 117
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 117

Met Glu Ser Gln Arg Ala Asn Ser
1               5

<210> SEQ ID NO 118
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 118

Met Ile Ser Gln Thr Leu Met Ala
1               5

<210> SEQ ID NO 119
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 119

Met Met Ser Gln Ser Leu Arg Ala
1               5

<210> SEQ ID NO 120
<211> LENGTH: 8
```

```
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 120

Asn Asn Val Gln Ser Ala Leu Asn
1               5

<210> SEQ ID NO 121
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 121

Asn Ser Ala Arg Thr Gln Leu Ser
1               5

<210> SEQ ID NO 122
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 122

Pro Gln Trp Asn Arg Thr Pro Leu
1               5

<210> SEQ ID NO 123
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 123

Pro Arg Phe Asn Asn Ser Ser Leu
1               5

<210> SEQ ID NO 124
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 124

Pro Val Asp Gly Gly Arg His Leu
1               5

<210> SEQ ID NO 125
```

```
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 125

Pro Trp Phe Asn Lys Ser Ser Leu
1               5

<210> SEQ ID NO 126
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 126

Gln Asp Met Asn Ser Gln Arg Ser
1               5

<210> SEQ ID NO 127
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 127

Gln Gly Ala Ser Asn Ser Gln Leu
1               5

<210> SEQ ID NO 128
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 128

Gln Gln Asn Gly Thr Arg Pro Ser
1               5

<210> SEQ ID NO 129
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 129

Gln Arg Ser Ala Tyr Pro Thr Ser
1               5
```

```
<210> SEQ ID NO 130
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 130

Gln Arg Thr Pro Ser Ile Thr Pro
1               5

<210> SEQ ID NO 131
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 131

Gln Trp Met Lys Glu Gln Ala Gly
1               5

<210> SEQ ID NO 132
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 132

Arg Asp Gly Arg His Pro Ser Glu
1               5

<210> SEQ ID NO 133
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 133

Arg Gly Thr Val Thr Val Glu Gln
1               5

<210> SEQ ID NO 134
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 134

Arg Pro Ala Asn His Ser Thr Ala
1               5
```

<210> SEQ ID NO 135
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 135

Arg Gln Gly Asp Ala Asp Thr Leu
1               5

<210> SEQ ID NO 136
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 136

Ser Ala Thr Ile Ser Leu Gln Val
1               5

<210> SEQ ID NO 137
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 137

Ser His Thr Asn Leu Arg Asp Thr
1               5

<210> SEQ ID NO 138
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 138

Ser Arg Met Gly Glu Thr Pro Gln
1               5

<210> SEQ ID NO 139
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 139

Ser Ser Gly Tyr Leu Thr Ala Asn
1               5

```
<210> SEQ ID NO 140
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 140

Thr Gly Asn Ser Pro Glu Gln Ala
1               5

<210> SEQ ID NO 141
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 141

Thr His Ser Gln Gly Arg Leu Ala
1               5

<210> SEQ ID NO 142
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 142

Thr Pro Ile Val Gly Ser Asn Val
1               5

<210> SEQ ID NO 143
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 143

Thr Pro Pro Lys Ser Pro Ser Met
1               5

<210> SEQ ID NO 144
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 144

Thr Arg Met Asp Glu Arg Ser Pro
```

```
1               5

<210> SEQ ID NO 145
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 145

Thr Thr Ala Thr Thr Ser Ile Thr
1               5

<210> SEQ ID NO 146
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 146

Val Val Gln Gly Glu Gln Lys Arg
1               5

<210> SEQ ID NO 147
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 147

Trp Asn Asp Arg Ser Gly Glu Arg
1               5

<210> SEQ ID NO 148
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 148

Trp Ser Gln Asp Ala Val Lys Gly
1               5

<210> SEQ ID NO 149
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 149
```

```
Trp Thr Gly Gly Gly Ser Gly Thr
1               5

<210> SEQ ID NO 150
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 150

Ala Gly Ala Ala Tyr Thr Pro Ala
1               5

<210> SEQ ID NO 151
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 151

Ala Pro Ser Val Ser Arg Glu Lys
1               5

<210> SEQ ID NO 152
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 152

Asp Tyr Met His Lys Thr Gly Leu
1               5

<210> SEQ ID NO 153
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 153

Gly Gly Met Asn Glu Thr Thr Arg
1               5

<210> SEQ ID NO 154
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 154
```

```
Gly Gly Ser Ala Phe Val Thr Gly
1               5

<210> SEQ ID NO 155
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 155

Gly Asn Ser His Thr Gly Ser Ser
1               5

<210> SEQ ID NO 156
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 156

Asn Ser Ala Arg Thr Gln Leu Ser
1               5

<210> SEQ ID NO 157
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 157

Pro Leu Thr Ile Leu Asn Arg His
1               5

<210> SEQ ID NO 158
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 158

Gln Gly Thr Arg Thr Asn Pro Pro
1               5

<210> SEQ ID NO 159
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)
```

```
<400> SEQUENCE: 159

Gln Ser Ser Ala Met Pro Arg Asn
1               5

<210> SEQ ID NO 160
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 160

Ser His Asn Ser Gln Pro Val Ala
1               5

<210> SEQ ID NO 161
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 161

Thr Ala Gln Gly Ala Ala Phe Arg
1               5

<210> SEQ ID NO 162
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 162

Thr Pro Gly Leu Asn Asn Ala Arg
1               5

<210> SEQ ID NO 163
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 163

Thr Ser Leu Gly Thr Pro Glu Ala
1               5

<210> SEQ ID NO 164
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)
```

<400> SEQUENCE: 164

Thr Thr Asn Leu Ala Lys Asn Ser
1               5

<210> SEQ ID NO 165
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 165

Trp Ser Pro Asp Ala Val Glu Gly
1               5

<210> SEQ ID NO 166
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(7)

<400> SEQUENCE: 166

Trp Thr Gly Gly Arg His Leu
1               5

<210> SEQ ID NO 167
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 167

Ala Val Ala Gly Asp Arg Leu Leu
1               5

<210> SEQ ID NO 168
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 168

Asp Leu Leu Thr Arg Ser Val Ser
1               5

<210> SEQ ID NO 169
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE

<222> LOCATION: (1)..(8)

<400> SEQUENCE: 169

Glu Trp Lys Thr Gln Leu Ala Leu
1               5

<210> SEQ ID NO 170
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 170

Gly Asn Ile Asn Val Val Pro His
1               5

<210> SEQ ID NO 171
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 171

Gly Ser Pro Ala Ala Ser Ser Trp
1               5

<210> SEQ ID NO 172
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 172

Lys His Ser Leu Thr Leu Glu Ser
1               5

<210> SEQ ID NO 173
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 173

Lys Pro Val Ser Thr Asp Thr Phe
1               5

<210> SEQ ID NO 174
<211> LENGTH: 8
<212> TYPE: PRT
<213> ORGANISM: Artificial Sequence
<220> FEATURE:
<223> OTHER INFORMATION: peptide
<220> FEATURE:

```
<221> NAME/KEY: PEPTIDE
<222> LOCATION: (1)..(8)

<400> SEQUENCE: 174

Leu Asp Arg Ser Gly Ser Thr Gly
1               5

<210> SEQ ID NO 175
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 175

Leu Gly Ala Gln Asn His Val Val
1               5

<210> SEQ ID NO 176
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 176

Leu Met Ala Thr Asp Tyr Gly Pro
1               5

<210> SEQ ID NO 177
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 177

Leu Arg Ala Thr Asp Tyr Gly Pro
1               5

<210> SEQ ID NO 178
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 178

Met Glu Arg Thr Glu Pro Leu Gly
1               5

<210> SEQ ID NO 179
<211> LENGTH: 8
<212> TYPE: PRT
<213> ORGANISM: Artificial Sequence
<220> FEATURE:
<223> OTHER INFORMATION: peptide
```

```
<220> FEATURE:
<221> NAME/KEY: PEPTIDE
<222> LOCATION: (1)..(8)

<400> SEQUENCE: 179

Asn Asp Gly Leu Arg Leu His Leu
1               5

<210> SEQ ID NO 180
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 180

Asn Leu Ser Ala His Ser His Ala
1               5

<210> SEQ ID NO 181
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 181

Asn Leu Ser Ala His Ser His Asp
1               5

<210> SEQ ID NO 182
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 182

Arg Ala Leu Asp Leu Val Thr Arg
1               5

<210> SEQ ID NO 183
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 183

Ser Ala Gly Met Ala Arg Asn Ser
1               5

<210> SEQ ID NO 184
<211> LENGTH: 8
<212> TYPE: PRT
<213> ORGANISM: Artificial Sequence
<220> FEATURE:
```

```
<223> OTHER INFORMATION: peptide
<220> FEATURE:
<221> NAME/KEY: PEPTIDE
<222> LOCATION: (1)..(8)

<400> SEQUENCE: 184

Ser Gly Gln Arg Val Gly Ser Ala
1               5

<210> SEQ ID NO 185
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 185

Ser Gly Gln Arg Val Gly Ser Asp
1               5

<210> SEQ ID NO 186
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 186

Thr Gly Arg Pro Glu Gln Pro Lys
1               5

<210> SEQ ID NO 187
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 187

Thr His Ser Pro Ile Lys Leu Pro
1               5

<210> SEQ ID NO 188
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: PEPTIDE
<222> LOCATION: (1)..(8)

<400> SEQUENCE: 188

Thr Gln Phe Ser Gln Ala Gln Arg
1               5

<210> SEQ ID NO 189
<211> LENGTH: 8
<212> TYPE: PRT
<213> ORGANISM: Artificial Sequence
```

-continued

```
<220> FEATURE:
<223> OTHER INFORMATION: peptide
<220> FEATURE:
<221> NAME/KEY: PEPTIDE
<222> LOCATION: (1)..(8)

<400> SEQUENCE: 189

Val Gly Asp Ser Ala Asn Leu Arg
1               5

<210> SEQ ID NO 190
<211> LENGTH: 10
<212> TYPE: DNA
<213> ORGANISM: adeno-associated virus

<400> SEQUENCE: 190
cgagccaacc                                                              10

<210> SEQ ID NO 191
<211> LENGTH: 27
<212> TYPE: DNA
<213> ORGANISM: adeno-associated virus

<400> SEQUENCE: 191
caaaccctgg ccgtgccctt caaggca                                           27

<210> SEQ ID NO 192
<211> LENGTH: 2211
<212> TYPE: DNA
<213> ORGANISM: adeno-associated virus

<400> SEQUENCE: 192
atggctgccg atggttatct tccagattgg ctcgaggaca accttagtga aggaattcgc        60
gagtggtggg ctttgaaacc tggagcccct caacccaagg caaatcaaca acatcaagac       120
aacgctcgag gtcttgtgct tccgggttac aaataccttg acccggcaa cggactcgac        180 aagggggagc cggtcaacgc agcagacgcg gcggccctcg agcacgacaa ggcctacgac       240
cagcagctca aggccggaga caacccgtac ctcaagtaca accacgccga cgccgagttc       300
caggagcggc tcaaagaaga tacgtctttt gggggcaacc tcgggcgagc agtcttccag       360
gccaaaaaga ggcttcttga acctcttggt ctggttgagg aagcggctaa gacggctcct       420
ggaaagaaga ggcctgtaga gcagtctcct caggaaccgg actcctccgc gggtattggc       480
aaatcgggtg cacagcccgc taaaaagaga ctcaatttcg gtcagactgg cgacacagag       540
tcagtcccag accctcaacc aatcggagaa cctcccgcag cccccactcagg tgtgggatct       600 cttacaatgg cttcaggtgg tggcgcacca gtggcagaca taacgaaggt gccgatgga       660 gtgggtagtt cctcgggaaa ttggcattgc gattcccaat ggctgggga cagagtcatc       720 accaccagca cccgaacctg ggcctgccc acctacaaca atcacctcta caagcaaatc       780
tccaacagca catctggagg atcttcaaat gacaacgcct acttcggcta cagcaccccc       840
tgggggtatt ttgacttcaa cagattccac tgccacttct caccacgtga ctggcagcga       900
ctcatcaaca caactgggg attccggcct aagcgactca acttcaagct cttcaacatt       960
caggtcaaag aggttacgga caacaatgga gtcaagacca tcgccaataa ccttaccagc      1020
acggtccagg tcttcacgga ctcagactat cagctcccgt acgtgctcgg gtcggctcac      1080
gagggctgcc tcccgccgtt cccagcggac gttttcatga ttcctcagta cgggtatctg      1140
acgcttaatg atggaagcca ggccgtgggt cgttcgtcct tttactgcct ggaatatttc      1200
```

```
ccgtcgcaaa tgctaagaac gggtaacaac ttccagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caagaaggaa gaggaccgtt tctttccttt gtctggatct    1620 ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa acacacctg tacctgcgga tcctccaacg     1980
gccttcaaca aggacaagct gaactctttc atcacccagt attctactgg ccaagtcagc    2040
gtggagatcg agtgggagct gcagaaggaa acagcaagc gctggaaccc ggagatccag     2100
tacacttcca actattacaa gtctaataat gttgaatttg ctgttaatac tgaaggtgta    2160
tatagtgaac cccgccccat tggcaccaga tacctgactc gtaatctgta a             2211

<210> SEQ ID NO 193
<211> LENGTH: 2211
<212> TYPE: DNA
<213> ORGANISM: adeno-associated virus

<400> SEQUENCE: 193
atggctgctg acggttatct tccagattgg ctcgaggaca acctttctga aggcattcgt      60
gagtggtggg ctctgaaacc tggagtccct caacccaaag cgaaccaaca acaccaggac     120
aaccgtcggg gtcttgtgct tccgggttac aaataccctcg acccggtaa cggactcgac     180 aaaggagagc cggtcaacga ggcggacgcg gcagccctcg aacacgacaa agcttacgac     240
cagcagctca aggccggtga caacccgtac ctcaagtaca accacgccga cgccgagttt     300
caggagcgtc ttcaagaaga tacgtctttt gggggcaacc ttggcagagc agtcttccag     360
gccaaaaaga ggatccttga gcctcttggt ctggttgagg aagcagctaa acggctcct     420 ggaaagaaga ggcctgtaga tcagtctcct caggaaccgg actcatcatc tggtgttggc     480
aaatcgggca acagcctgc cagaaaaaga ctaaatttcg gtcagactgg cgactcagag     540
tcagtcccag accctcaacc tctcggagaa ccaccagcag cccccacaag tttgggatct     600
aatacaatgg cttcaggcgg tggcgcacca atggcagaca ataacgaggg tgccgatgga    660
gtgggtaatt cctcaggaaa ttggcattgc gattcccaat ggctgggcga cagagtcatc    720
accaccagca ccagaacctg gcccctgccc acttacaaca accatctcta caagcaaatc    780
tccagccaat caggagcttc aaacgacaac cactactttg gctacagcac cccttggggg    840
tattttgact ttaacagatt ccactgccac ttctcaccac gtgactggca gcgactcatt    900
aacaacaact ggggattccg gcccaagaaa ctcagcttca gctcttcaa catccaagtt    960 aaagaggtca cgcagaacga tggcacgacg actattgcca ataacctac cagcacggtt   1020 caagtgttta cggactcgga gtatcagctc ccgtacgtgc tcgggtcggc gcaccaaggc   1080
tgtctcccgc cgtttccagc ggacgtcttc atggtccctc agtatggata cctcacctg    1140
```

```
aacaacggaa gtcaagcggt gggacgctca tccttttact gcctggagta cttcccttcg    1200
cagatgctaa ggactggaaa taacttccaa ttcagctata ccttcgagga tgtaccttt     1260 cacagcagct acgctcacag ccagagtttg gatcgcttga tgaatcctct tattgatcag    1320
tatctgtact acctgaacag aacgcaagga acaacctctg gaacaaccaa ccaatcacgg    1380
ctgcttttta gccaggctgg gcctcagtct atgtctttgc aggccagaaa ttggctacct    1440
gggccctgct accggcaaca gagactttca aagactgcta acgacaacaa caacagtaac    1500
tttccttgga cagcggccag caaatatcat ctcaatggcc gcgactcgct ggtgaatcca    1560
ggaccagcta tggccagtca aaggacgat gaagaaaaat ttttccctat gcacggcaat     1620
ctaatatttg gcaaagaagg gacaacggca agtaacgcag aattagataa tgtaatgatt    1680
acggatgaag aagagattcg taccaccaat cctgtggcaa cagagcagta tggaactgtg    1740
gcaaataact tgcagagctc aaatacagct cccacgacta gaactgtcaa tgatcagggg    1800
gccttacctg gcatggtgtg gcaagatcgt gacgtgtacc ttcaaggacc tatctgggca    1860
aagattcctc acacggatgg acactttcat ccttctcctc tgatgggagg ctttggactg    1920
aaacatccgc ctcctcaaat catgatcaaa aatactccgg taccggcaaa tcctccgacg    1980
actttcagcc cggccaagtt tgcttcattt atcactcagt actccactgg acaggtcagc    2040
gtggaaattg agtgggagct acagaaagaa aacagcaaac gttggaatcc agagattcag    2100
tacacttcca actacaacaa gtctgttaat gtggactta ctgtagacac taatggtgtt     2160
tatagtgaac ctcgccctat tggaaccgg tatctcacac gaaacttgta a              2211
```

<210> SEQ ID NO 194
<211> LENGTH: 41
<212> TYPE: DNA
<213> ORGANISM: adeno-associated virus

<400> SEQUENCE: 194

```
gcaagaaagg ccagcagccc gccagaaaga gactcaattt c                        41
```

<210> SEQ ID NO 195
<211> LENGTH: 131
<212> TYPE: DNA
<213> ORGANISM: adeno-associated virus

<400> SEQUENCE: 195

```
cgggtattgg caaatcgggt gcacagcccg ctaaaagag actcaatttc ggtcagactg      60
gcgacacaga gtcagtccca gaccctcaac caatcggaga acctcccgca gcccctcag    120 gtgtgggatc t                                                        131
```

<210> SEQ ID NO 196
<211> LENGTH: 63
<212> TYPE: DNA
<213> ORGANISM: adeno-associated virus

<400> SEQUENCE: 196

```
actgaaggtg tatatagtga accccgcccc attggcacca gatacctgac tcgtaatctg     60
taa                                                                   63
```

<210> SEQ ID NO 197
<211> LENGTH: 131
<212> TYPE: DNA
<213> ORGANISM: Artificial Sequence
<220> FEATURE:

```
<223> OTHER INFORMATION: Codon modified AAV9
<220> FEATURE:
<221> NAME/KEY: misc_feature
<222> LOCATION: (1)..(131)

<400> SEQUENCE: 197
cgggtattgg caaatcgggt gcacagcctg ccaagaagcg cctgaacttt ggccagaccg    60
gcgacacaga gagcgttccg gaccctcaac caatcggaga acctcccgca gcccccctcag   120 gtgtgggatc t                                                        131

<210> SEQ ID NO 198
<211> LENGTH: 63
<212> TYPE: DNA
<213> ORGANISM: Artificial Sequence
<220> FEATURE:
<223> OTHER INFORMATION: Codon modified AAV9
<220> FEATURE:
<221> NAME/KEY: misc_feature
<222> LOCATION: (1)..(63)

<400> SEQUENCE: 198
actgaaggtg tatatagtga accccgccca atcgggacaa gatatctgac aagaaacctg    60
taa                                                                  63

<210> SEQ ID NO 199
<211> LENGTH: 10
<212> TYPE: DNA
<213> ORGANISM: adeno-associated virus

<400> SEQUENCE: 199
cttaccagca                                                           10

<210> SEQ ID NO 200
<211> LENGTH: 10
<212> TYPE: DNA
<213> ORGANISM: adeno-associated virus

<400> SEQUENCE: 200
tttaccttca                                                           10

<210> SEQ ID NO 201
<211> LENGTH: 10
<212> TYPE: DNA
<213> ORGANISM: adeno-associated virus

<400> SEQUENCE: 201
tataccttcg                                                           10

<210> SEQ ID NO 202
<211> LENGTH: 10
<212> TYPE: DNA
<213> ORGANISM: adeno-associated virus

<400> SEQUENCE: 202
attacctgaa                                                           10

<210> SEQ ID NO 203
<211> LENGTH: 10
<212> TYPE: DNA
<213> ORGANISM: adeno-associated virus

<400> SEQUENCE: 203
gctacctgga                                                           10
```

```
<210> SEQ ID NO 204
<211> LENGTH: 10
<212> TYPE: DNA
<213> ORGANISM: adeno-associated virus

<400> SEQUENCE: 204
tttacctgga                                                          10

<210> SEQ ID NO 205
<211> LENGTH: 10
<212> TYPE: DNA
<213> ORGANISM: adeno-associated virus

<400> SEQUENCE: 205
attacctggc                                                          10

<210> SEQ ID NO 206
<211> LENGTH: 10
<212> TYPE: DNA
<213> ORGANISM: adeno-associated virus

<400> SEQUENCE: 206
cttacctggc                                                          10

<210> SEQ ID NO 207
<211> LENGTH: 10
<212> TYPE: DNA
<213> ORGANISM: adeno-associated virus

<400> SEQUENCE: 207
tgtacctgca                                                          10

<210> SEQ ID NO 208
<211> LENGTH: 10
<212> TYPE: DNA
<213> ORGANISM: adeno-associated virus

<400> SEQUENCE: 208
gttaccttac                                                          10

<210> SEQ ID NO 209
<211> LENGTH: 10
<212> TYPE: DNA
<213> ORGANISM: adeno-associated virus

<400> SEQUENCE: 209
gatacctgac                                                          10

<210> SEQ ID NO 210
<211> LENGTH: 10
<212> TYPE: DNA
<213> ORGANISM: adeno-associated virus

<400> SEQUENCE: 210
cttacccgtc                                                          10

<210> SEQ ID NO 211
<211> LENGTH: 10
<212> TYPE: DNA
<213> ORGANISM: adeno-associated virus

<400> SEQUENCE: 211
```
ctcacacgaa                                                          10

<210> SEQ ID NO 212
<211> LENGTH: 10
<212> TYPE: DNA
<213> ORGANISM: adeno-associated virus

<400> SEQUENCE: 212
agcgtctgca                                                          10

<210> SEQ ID NO 213
<211> LENGTH: 10
<212> TYPE: DNA
<213> ORGANISM: adeno-associated virus

<400> SEQUENCE: 213
ggctcctgga                                                          10

<210> SEQ ID NO 214
<211> LENGTH: 10
<212> TYPE: DNA
<213> ORGANISM: adeno-associated virus

<400> SEQUENCE: 214
gcccgctaaa                                                          10

<210> SEQ ID NO 215
<211> LENGTH: 10
<212> TYPE: DNA
<213> ORGANISM: adeno-associated virus

<400> SEQUENCE: 215
tcaccctgaa                                                          10

<210> SEQ ID NO 216
<211> LENGTH: 10
<212> TYPE: DNA
<213> ORGANISM: adeno-associated virus

<400> SEQUENCE: 216
actgcctgga                                                          10

<210> SEQ ID NO 217
<211> LENGTH: 10
<212> TYPE: DNA
<213> ORGANISM: adeno-associated virus

<400> SEQUENCE: 217
actacctgaa                                                          10

<210> SEQ ID NO 218
<211> LENGTH: 10
<212> TYPE: DNA
<213> ORGANISM: adeno-associated virus

<400> SEQUENCE: 218
cgtttctaaa                                                          10

<210> SEQ ID NO 219
<211> LENGTH: 10
<212> TYPE: DNA
<213> ORGANISM: adeno-associated virus

<400> SEQUENCE: 219
aaacactgca 10

<210> SEQ ID NO 220
<211> LENGTH: 10
<212> TYPE: DNA
<213> ORGANISM: adeno-associated virus

<400> SEQUENCE: 220
gggagctgca 10

<210> SEQ ID NO 221
<211> LENGTH: 736
<212> TYPE: PRT
<213> ORGANISM: adeno-associated virus

<400> SEQUENCE: 221

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
        180                 185                 190

Ala Ala Pro Ser Gly Val Gly Ser Leu Thr Met Ala Ser Gly Gly Gly
    195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
        260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
```

-continued

```
            305                 310                 315                 320
        Gln Val Lys Glu Val Thr Asp Asn Asn Gly Val Lys Thr Ile Ala Asn
                        325                 330                 335
        Asn Leu Thr Ser Thr Val Gln Val Phe Thr Asp Ser Asp Tyr Gln Leu
                        340                 345                 350
        Pro Tyr Val Leu Gly Ser Ala His Glu Gly Cys Leu Pro Phe Pro
                        355                 360                 365
        Ala Asp Val Phe Met Ile Pro Gln Tyr Gly Tyr Leu Thr Leu Asn Asp
                370                 375                 380
        Gly Ser Gln Ala Val Gly Arg Ser Ser Phe Tyr Cys Leu Glu Tyr Phe
        385                 390                 395                 400
        Pro Ser Gln Met Leu Arg Thr Gly Asn Asn Phe Gln Phe Ser Tyr Glu
                        405                 410                 415
        Phe Glu Asn Val Pro Phe His Ser Ser Tyr Ala His Ser Gln Ser Leu
                        420                 425                 430
        Asp Arg Leu Met Asn Pro Leu Ile Asp Gln Tyr Leu Tyr Tyr Leu Ser
                        435                 440                 445
        Lys Thr Ile Asn Gly Ser Gly Gln Asn Gln Gln Thr Leu Lys Phe Ser
                        450                 455                 460
        Val Ala Gly Pro Ser Asn Met Ala Val Gln Gly Arg Asn Tyr Ile Pro
        465                 470                 475                 480
        Gly Pro Ser Tyr Arg Gln Gln Arg Val Ser Thr Thr Val Thr Gln Asn
                        485                 490                 495
        Asn Asn Ser Glu Phe Ala Trp Pro Gly Ala Ser Ser Trp Ala Leu Asn
                        500                 505                 510
        Gly Arg Asn Ser Leu Met Asn Pro Gly Pro Ala Met Ala Ser His Lys
                        515                 520                 525
        Glu Gly Glu Asp Arg Phe Phe Pro Leu Ser Gly Ser Leu Ile Phe Gly
                        530                 535                 540
        Lys Gln Gly Thr Gly Arg Asp Asn Val Asp Ala Asp Lys Val Met Ile
        545                 550                 555                 560
        Thr Asn Glu Glu Glu Ile Lys Thr Thr Asn Pro Val Ala Thr Glu Ser
                        565                 570                 575
        Tyr Gly Gln Val Ala Thr Asn His Gln Ser Ala Gln Ala Gln Ala Gln
                        580                 585                 590
        Thr Gly Trp Val Gln Asn Gln Gly Ile Leu Pro Gly Met Val Trp Gln
                        595                 600                 605
        Asp Arg Asp Val Tyr Leu Gln Gly Pro Ile Trp Ala Lys Ile Pro His
        610                 615                 620
        Thr Asp Gly Asn Phe His Pro Ser Pro Leu Met Gly Gly Phe Gly Met
        625                 630                 635                 640
        Lys His Pro Pro Pro Gln Ile Leu Ile Lys Asn Thr Pro Val Pro Ala
                        645                 650                 655
        Asp Pro Pro Thr Ala Phe Asn Lys Asp Lys Leu Asn Ser Phe Ile Thr
                        660                 665                 670
        Gln Tyr Ser Thr Gly Gln Val Ser Val Glu Ile Glu Trp Glu Leu Gln
                        675                 680                 685
        Lys Glu Asn Ser Lys Arg Trp Asn Pro Glu Ile Gln Tyr Thr Ser Asn
                        690                 695                 700
        Tyr Tyr Lys Ser Asn Asn Val Glu Phe Ala Val Asn Thr Glu Gly Val
        705                 710                 715                 720
        Tyr Ser Glu Pro Arg Pro Ile Gly Thr Arg Tyr Leu Thr Arg Asn Leu
                        725                 730                 735
```

<210> SEQ ID NO 222
<211> LENGTH: 736
<212> TYPE: PRT
<213> ORGANISM: Artificial Sequence
<220> FEATURE:
<223> OTHER INFORMATION: synthesized
<220> FEATURE:
<221> NAME/KEY: PEPTIDE
<222> LOCATION: (1)..(736)

<400> SEQUENCE: 222

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Gly Gly Ser Ser Asn Asp Ala
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350
```

```
Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 223
<211> LENGTH: 41
<212> TYPE: DNA
<213> ORGANISM: adeno-associated virus
```

```
<400> SEQUENCE: 223
gcaagaaagg ccagcagccc gccagaaaga gactcaattt c                    41

<210> SEQ ID NO 224
<211> LENGTH: 41
<212> TYPE: DNA
<213> ORGANISM: adeno-associated virus

<400> SEQUENCE: 224
gcaagaaagg ccagcagccc gccggaaaga gactcaattt c                    41

<210> SEQ ID NO 225
<211> LENGTH: 41
<212> TYPE: DNA
<213> ORGANISM: adeno-associated virus

<400> SEQUENCE: 225
gcaagaaagg ccagcagccc gctagaaaga gactgaactt t                    41

<210> SEQ ID NO 226
<211> LENGTH: 41
<212> TYPE: DNA
<213> ORGANISM: adeno-associated virus

<400> SEQUENCE: 226
gcaagaaggg ccagcagccc gccagaaaga gactcaattt c                    41

<210> SEQ ID NO 227
<211> LENGTH: 41
<212> TYPE: DNA
<213> ORGANISM: adeno-associated virus

<400> SEQUENCE: 227
gcaagaaagg ccagcggccc gctaaaaaga gactgaactt t                    41

<210> SEQ ID NO 228
<211> LENGTH: 41
<212> TYPE: DNA
<213> ORGANISM: adeno-associated virus

<400> SEQUENCE: 228
gcaagaaagg ccagcagccc gctaaaaaga gactgaactt t                    41

<210> SEQ ID NO 229
<211> LENGTH: 41
<212> TYPE: DNA
<213> ORGANISM: adeno-associated virus

<400> SEQUENCE: 229
gcaagaaagg ccagcagccc gctaaaaaga gactgagctt t                    41

<210> SEQ ID NO 230
<211> LENGTH: 41
<212> TYPE: DNA
<213> ORGANISM: adeno-associated virus

<400> SEQUENCE: 230
gcaagaaagg ccaccagccc gcgagaaaga gactgaactt t                    41

<210> SEQ ID NO 231
<211> LENGTH: 41
<212> TYPE: DNA
<213> ORGANISM: adeno-associated virus
```

<400> SEQUENCE: 231
gcaagacagg ccagcagccc gcgaaaaaga gactcaactt t    41

<210> SEQ ID NO 232
<211> LENGTH: 41
<212> TYPE: DNA
<213> ORGANISM: adeno-associated virus

<400> SEQUENCE: 232
gcaagaaagg ccagcagccc gctaaaaaga agctcaactt t    41

<210> SEQ ID NO 233
<211> LENGTH: 41
<212> TYPE: DNA
<213> ORGANISM: adeno-associated virus

<400> SEQUENCE: 233
gcaagaaagg ccagcagccc gctaaaaaga gactcaactt t    41

<210> SEQ ID NO 234
<211> LENGTH: 41
<212> TYPE: DNA
<213> ORGANISM: adeno-associated virus

<400> SEQUENCE: 234
gcaagaaagg ccagcagccc gcgaaaaaga gactcaactt t    41

<210> SEQ ID NO 235
<211> LENGTH: 40
<212> TYPE: DNA
<213> ORGANISM: adeno-associated virus

<400> SEQUENCE: 235
gcaagtcagg ccagcagccc gcgaaaaaga gactgaattt    40

<210> SEQ ID NO 236
<211> LENGTH: 41
<212> TYPE: DNA
<213> ORGANISM: adeno-associated virus

<400> SEQUENCE: 236
gcaagtcagg ccggcagccc gcgaaaaaga gactgaattt t    41

<210> SEQ ID NO 237
<211> LENGTH: 41
<212> TYPE: DNA
<213> ORGANISM: adeno-associated virus

<400> SEQUENCE: 237
gcaagaaagg ccaacagccc gccagaaaaa gactcaattt t    41

<210> SEQ ID NO 238
<211> LENGTH: 41
<212> TYPE: DNA
<213> ORGANISM: adeno-associated virus

<400> SEQUENCE: 238
gcaagacagg ccagcagccc gctaaaaaga gactcaattt t    41

<210> SEQ ID NO 239
<211> LENGTH: 41
<212> TYPE: DNA

```
<213> ORGANISM: adeno-associated virus

<400> SEQUENCE: 239
gcaagaacgg ccagccgccc gctaaaaaga agctcaactt t                    41

<210> SEQ ID NO 240
<211> LENGTH: 41
<212> TYPE: DNA
<213> ORGANISM: adeno-associated virus

<400> SEQUENCE: 240
gcaaaaaagg ccagcagccc gctaaaaaga agctcaattt t                    41

<210> SEQ ID NO 241
<211> LENGTH: 40
<212> TYPE: DNA
<213> ORGANISM: adeno-associated virus

<400> SEQUENCE: 241
gaaaggcggg ccagcagcct gcaagaaaaa gatgaatttt                      40

<210> SEQ ID NO 242
<211> LENGTH: 40
<212> TYPE: DNA
<213> ORGANISM: adeno-associated virus

<400> SEQUENCE: 242
gaaaagcggg caaccagcct gcaagaaaaa gatgaatttc                      40

<210> SEQ ID NO 243
<211> LENGTH: 41
<212> TYPE: DNA
<213> ORGANISM: adeno-associated virus

<400> SEQUENCE: 243
gaaaagcggg ccagcagcct gcaagaaaga gattgaattt c                    41

<210> SEQ ID NO 244
<211> LENGTH: 41
<212> TYPE: DNA
<213> ORGANISM: adeno-associated virus

<400> SEQUENCE: 244
gaaaagcggg caaccagcct gcaagaaaga gattgaattt c                    41

<210> SEQ ID NO 245
<211> LENGTH: 41
<212> TYPE: DNA
<213> ORGANISM: adeno-associated virus

<400> SEQUENCE: 245
gaaaagcggg ccagcagcct gcgagaaaga gattgaattt t                    41

<210> SEQ ID NO 246
<211> LENGTH: 41
<212> TYPE: DNA
<213> ORGANISM: adeno-associated virus

<400> SEQUENCE: 246
gaaaagcggg ccagcagcct gcaagaaaaa gattgaattt c                    41

<210> SEQ ID NO 247
<211> LENGTH: 41
```

<212> TYPE: DNA
<213> ORGANISM: adeno-associated virus

<400> SEQUENCE: 247
gaaagtcggg caaccagcct gcaagaaaga gattgaattt c        41

<210> SEQ ID NO 248
<211> LENGTH: 41
<212> TYPE: DNA
<213> ORGANISM: adeno-associated virus

<400> SEQUENCE: 248
gaaaagcggg ccagcagcct gcaagaaaga gattgaattt t        41

<210> SEQ ID NO 249
<211> LENGTH: 41
<212> TYPE: DNA
<213> ORGANISM: adeno-associated virus

<400> SEQUENCE: 249
gaaaagcggg caaccagcct gcaagaaaaa gattgaattt t        41

<210> SEQ ID NO 250
<211> LENGTH: 41
<212> TYPE: DNA
<213> ORGANISM: adeno-associated virus

<400> SEQUENCE: 250
gaaaagcggg ccagcagcct gcgagaaaaa gattgaattt t        41

<210> SEQ ID NO 251
<211> LENGTH: 41
<212> TYPE: DNA
<213> ORGANISM: adeno-associated virus

<400> SEQUENCE: 251
gaaaagcggg ccagcagcct gcaagaaaaa gattgaattt t        41

<210> SEQ ID NO 252
<211> LENGTH: 41
<212> TYPE: DNA
<213> ORGANISM: adeno-associated virus

<400> SEQUENCE: 252
gaaaagcggg ccagcagcct gcaagaaaaa gattaaattt t        41

<210> SEQ ID NO 253
<211> LENGTH: 41
<212> TYPE: DNA
<213> ORGANISM: adeno-associated virus

<400> SEQUENCE: 253
gaaaagcggg ccagcggcct gcaagaaaaa gattaaattt t        41

<210> SEQ ID NO 254
<211> LENGTH: 41
<212> TYPE: DNA
<213> ORGANISM: adeno-associated virus

<400> SEQUENCE: 254
gaaaagcggg ccatcagcct gcgagaaaga gattgaattt t        41

<210> SEQ ID NO 255

<210> SEQ ID NO 255
<211> LENGTH: 41
<212> TYPE: DNA
<213> ORGANISM: adeno-associated virus

<400> SEQUENCE: 255
gaaaggcggg ccatcagcct gcgagaaaga gattgaattt t        41

<210> SEQ ID NO 256
<211> LENGTH: 41
<212> TYPE: DNA
<213> ORGANISM: adeno-associated virus

<400> SEQUENCE: 256
gaaaagcggg ccagcagcct gcaagaaaaa gactgaattt c        41

<210> SEQ ID NO 257
<211> LENGTH: 41
<212> TYPE: DNA
<213> ORGANISM: adeno-associated virus

<400> SEQUENCE: 257
gcaaatcggg caaacagcct gccagaaaaa gactaaattt c        41

<210> SEQ ID NO 258
<211> LENGTH: 41
<212> TYPE: DNA
<213> ORGANISM: adeno-associated virus

<400> SEQUENCE: 258
gcaaatcagg ccagcagccc gctagaaaaa gactgaattt t        41

<210> SEQ ID NO 259
<211> LENGTH: 41
<212> TYPE: DNA
<213> ORGANISM: adeno-associated virus

<400> SEQUENCE: 259
gcaaatcagg ccagcagccc gctaagaaaa gactcaattt t        41

<210> SEQ ID NO 260
<211> LENGTH: 41
<212> TYPE: DNA
<213> ORGANISM: adeno-associated virus

<400> SEQUENCE: 260
gcaaatcggg tgcacagccc gctaaaaaga gactcaattt c        41

<210> SEQ ID NO 261
<211> LENGTH: 41
<212> TYPE: DNA
<213> ORGANISM: adeno-associated virus

<400> SEQUENCE: 261
gcaaatcggg ttcacagccc gctaaaaaga aactcaattt c        41

<210> SEQ ID NO 262
<211> LENGTH: 41
<212> TYPE: DNA
<213> ORGANISM: adeno-associated virus

<400> SEQUENCE: 262
gcaaaaaagg caaacaacca gccaaaaaga gactcaactt t        41

<210> SEQ ID NO 263
<211> LENGTH: 41
<212> TYPE: DNA
<213> ORGANISM: adeno-associated virus

<400> SEQUENCE: 263
gcaaaaaagg caaacaacca gccagaaaga ggctcaactt t                 41

<210> SEQ ID NO 264
<211> LENGTH: 60
<212> TYPE: DNA
<213> ORGANISM: adeno-associated virus

<400> SEQUENCE: 264
gccaagaaaa agcaaaaaga cggcgaacca gccgactctg ctagaaggac actcgacttt    60

<210> SEQ ID NO 265
<211> LENGTH: 41
<212> TYPE: DNA
<213> ORGANISM: adeno-associated virus

<400> SEQUENCE: 265
gcaaaaaagg caagcagccg gctaaaaaga agctcgtttt c                 41

<210> SEQ ID NO 266
<211> LENGTH: 41
<212> TYPE: DNA
<213> ORGANISM: adeno-associated virus

<400> SEQUENCE: 266
gcaagaaagg caaacagcct gccagaaaga gactcaactt t                 41

<210> SEQ ID NO 267
<211> LENGTH: 38
<212> TYPE: DNA
<213> ORGANISM: adeno-associated virus

<400> SEQUENCE: 267
ccaagaaaaa caagaagcct cgcaaggaaa gaccttcc                     38

<210> SEQ ID NO 268
<211> LENGTH: 27
<212> TYPE: DNA
<213> ORGANISM: adeno-associated virus

<400> SEQUENCE: 268
aagaggactc caagccttcc acctcgt                                 27

<210> SEQ ID NO 269
<211> LENGTH: 26
<212> TYPE: DNA
<213> ORGANISM: adeno-associated virus

<400> SEQUENCE: 269
aagaggactc caagccttcc actcgt                                  26

<210> SEQ ID NO 270
<211> LENGTH: 35
<212> TYPE: DNA
<213> ORGANISM: adeno-associated virus

<400> SEQUENCE: 270
ttaagaagcc taaacctacc gaggaagtca gtgcg                        35

<210> SEQ ID NO 271
<211> LENGTH: 55
<212> TYPE: DNA
<213> ORGANISM: adeno-associated virus

<400> SEQUENCE: 271
tgtttactct gagcctcgcc ccattggcac tcgttacctc acccgtaatc tgtaa    55

<210> SEQ ID NO 272
<211> LENGTH: 55
<212> TYPE: DNA
<213> ORGANISM: adeno-associated virus

<400> SEQUENCE: 272
tgtttactct gagcctcgcc ccattggcac tcgttacccc acccgtaatc tgtaa    55

<210> SEQ ID NO 273
<211> LENGTH: 55
<212> TYPE: DNA
<213> ORGANISM: adeno-associated virus

<400> SEQUENCE: 273
tgtttactct gagcctcgcc ctattggcac tcgttacctc acccgtaatc tgtaa    55

<210> SEQ ID NO 274
<211> LENGTH: 54
<212> TYPE: DNA
<213> ORGANISM: adeno-associated virus

<400> SEQUENCE: 274
tgtttattct gagcctcgcc cattggtact cgttacctca cccgtaatct gtaa     54

<210> SEQ ID NO 275
<211> LENGTH: 55
<212> TYPE: DNA
<213> ORGANISM: adeno-associated virus

<400> SEQUENCE: 275
aacttattct gagcctcgcc ccattggtac tcgctacctc acccgtaatc tgtaa    55

<210> SEQ ID NO 276
<211> LENGTH: 55
<212> TYPE: DNA
<213> ORGANISM: adeno-associated virus

<400> SEQUENCE: 276
aacttattct gagcctcgcc ccattggtac tcgttacctc acccgtaatc tgtaa    55

<210> SEQ ID NO 277
<211> LENGTH: 55
<212> TYPE: DNA
<213> ORGANISM: adeno-associated virus

<400> SEQUENCE: 277
tacatattca gagcctcgcc ccattggtac tcgttatctg acacgtaatc tgtaa    55

<210> SEQ ID NO 278
<211> LENGTH: 55
<212> TYPE: DNA
<213> ORGANISM: adeno-associated virus

<400> SEQUENCE: 278
aacttattct gagcctcgcc ccattggtac tcgttatctg acacgtaatc tgtaa    55

```
<210> SEQ ID NO 279
<211> LENGTH: 55
<212> TYPE: DNA
<213> ORGANISM: adeno-associated virus

<400> SEQUENCE: 279
tacttattca gagcctcgcc ccattggcac tcgttatctc acccgtaatc tgtaa     55

<210> SEQ ID NO 280
<211> LENGTH: 55
<212> TYPE: DNA
<213> ORGANISM: adeno-associated virus

<400> SEQUENCE: 280
tacttattca gagcctcgcc ccattggcac ccgttacctc acccgtaacc tgtaa     55

<210> SEQ ID NO 281
<211> LENGTH: 54
<212> TYPE: DNA
<213> ORGANISM: adeno-associated virus

<400> SEQUENCE: 281
tgtgtattca gagcctcgcc cattggcacc agatacctga ctcgtaatct gtaa      54

<210> SEQ ID NO 282
<211> LENGTH: 55
<212> TYPE: DNA
<213> ORGANISM: adeno-associated virus

<400> SEQUENCE: 282
tacttattca gagcctcgcc ccattggcac ccgttacctc acccgtagcc tgtaa     55

<210> SEQ ID NO 283
<211> LENGTH: 55
<212> TYPE: DNA
<213> ORGANISM: adeno-associated virus

<400> SEQUENCE: 283
cacttattct gagcctcgcc ccatcggcac ccgttacctc acccgtaatc tgtaa     55

<210> SEQ ID NO 284
<211> LENGTH: 55
<212> TYPE: DNA
<213> ORGANISM: adeno-associated virus

<400> SEQUENCE: 284
tgtatatagc gaaccccgcc ccattggcac tcgttacctc acccgtaatc tgtaa     55

<210> SEQ ID NO 285
<211> LENGTH: 55
<212> TYPE: DNA
<213> ORGANISM: adeno-associated virus

<400> SEQUENCE: 285
tgtatatagt gaaccccgcc ccattggcac tcgttacctc acccgtaatc tgtaa     55

<210> SEQ ID NO 286
<211> LENGTH: 55
<212> TYPE: DNA
<213> ORGANISM: adeno-associated virus

<400> SEQUENCE: 286
```
cgtgtactct gaaccccgcc ccattggcac ccgttacctc acccgtaatc tgtaa            55

<210> SEQ ID NO 287
<211> LENGTH: 55
<212> TYPE: DNA
<213> ORGANISM: adeno-associated virus

<400> SEQUENCE: 287
tgtttactct gagcctcgcc ccattggtac tcgttacctc acccgtaatt tgtaa            55

<210> SEQ ID NO 288
<211> LENGTH: 55
<212> TYPE: DNA
<213> ORGANISM: adeno-associated virus

<400> SEQUENCE: 288
ggtttatagc gagcctcgcc ccattggcac ccgttacctc acccgcaacc tgtaa            55

<210> SEQ ID NO 289
<211> LENGTH: 55
<212> TYPE: DNA
<213> ORGANISM: adeno-associated virus

<400> SEQUENCE: 289
ggtttatact gagcctcgcc ccattggcac ccgttacctc acccgtaacc tgtaa            55

<210> SEQ ID NO 290
<211> LENGTH: 55
<212> TYPE: DNA
<213> ORGANISM: adeno-associated virus

<400> SEQUENCE: 290
tgtttatact gagcctcgcc ccattggcac tcgttacctc acccgtaatc tgtaa            55

<210> SEQ ID NO 291
<211> LENGTH: 55
<212> TYPE: DNA
<213> ORGANISM: adeno-associated virus

<400> SEQUENCE: 291
tgtttatact gagcctcgcc ccattggcac tcgttacctc ccccgtaatc tgtaa            55

<210> SEQ ID NO 292
<211> LENGTH: 55
<212> TYPE: DNA
<213> ORGANISM: adeno-associated virus

<400> SEQUENCE: 292
actttatact gagcctcgcc ccattggcac ccgttacctt acccgtcccc tgtaa            55

<210> SEQ ID NO 293
<211> LENGTH: 55
<212> TYPE: DNA
<213> ORGANISM: adeno-associated virus

<400> SEQUENCE: 293
actttatact gagcctcgcc ccattggcac ccgttacctc acccgtcccc tgtaa            55

<210> SEQ ID NO 294
<211> LENGTH: 55
<212> TYPE: DNA
<213> ORGANISM: adeno-associated virus

<400> SEQUENCE: 294
cgtgtattca gagcctcgcc ccattggcac cagatacctg actcgtaatc tgtaa            55

<210> SEQ ID NO 295
<211> LENGTH: 55
<212> TYPE: DNA
<213> ORGANISM: adeno-associated virus

<400> SEQUENCE: 295
cgtgtattca gagcctcgcc ccattggcac cagatacctg actcgtaatt tgtaa            55

<210> SEQ ID NO 296
<211> LENGTH: 55
<212> TYPE: DNA
<213> ORGANISM: adeno-associated virus

<400> SEQUENCE: 296
ggtgtattca gagcctcgcc ctattggcac cagatacctg actcgtaatc tgtaa            55

<210> SEQ ID NO 297
<211> LENGTH: 55
<212> TYPE: DNA
<213> ORGANISM: adeno-associated virus

<400> SEQUENCE: 297
tgtgtattca gagcctcgcc ccattggcac caggtacctg actcgtaatc tgtaa            55

<210> SEQ ID NO 298
<211> LENGTH: 55
<212> TYPE: DNA
<213> ORGANISM: adeno-associated virus

<400> SEQUENCE: 298
tgtgtattca gagcctcgcc ccattggcac cagatacctg actcgtaatc tgtaa            55

<210> SEQ ID NO 299
<211> LENGTH: 55
<212> TYPE: DNA
<213> ORGANISM: adeno-associated virus

<400> SEQUENCE: 299
tgtgtattca gagcctcgcc ccattggcgc cagatacctg actcgtaatc tgtaa            55

<210> SEQ ID NO 300
<211> LENGTH: 55
<212> TYPE: DNA
<213> ORGANISM: adeno-associated virus

<400> SEQUENCE: 300
tgtgtattca gagcctcgcc ccattggcac cagatacccg actcgtaatc tgtaa            55

<210> SEQ ID NO 301
<211> LENGTH: 55
<212> TYPE: DNA
<213> ORGANISM: adeno-associated virus

<400> SEQUENCE: 301
tgtgtattca gagcctcgcc ccattggcac cacatacctg actcgtaatc tgtaa            55

<210> SEQ ID NO 302
<211> LENGTH: 55
<212> TYPE: DNA
<213> ORGANISM: adeno-associated virus

```
<400> SEQUENCE: 302
cgtgtactca gagcctcgcc ccattggcac cagatacctg actcgtaatc tgtaa        55

<210> SEQ ID NO 303
<211> LENGTH: 56
<212> TYPE: DNA
<213> ORGANISM: adeno-associated virus

<400> SEQUENCE: 303
tgtgtattca gagcctcgcc ccattggcac cagatacctg actcgtaatc tgtaat       56

<210> SEQ ID NO 304
<211> LENGTH: 55
<212> TYPE: DNA
<213> ORGANISM: adeno-associated virus

<400> SEQUENCE: 304
tgtgtattca gagccttgcc ccattggcac cagatacctg actcgtaatc tgtaa        55

<210> SEQ ID NO 305
<211> LENGTH: 55
<212> TYPE: DNA
<213> ORGANISM: adeno-associated virus

<400> SEQUENCE: 305
tgtttatagt gaacctcgcc ctattggaac ccggtatctc acacgaaact tgtga        55

<210> SEQ ID NO 306
<211> LENGTH: 55
<212> TYPE: DNA
<213> ORGANISM: adeno-associated virus

<400> SEQUENCE: 306
tgtttatagt gaacctcgcc ctattggaac ccggtatctc acacgaaact tgtaa        55

<210> SEQ ID NO 307
<211> LENGTH: 55
<212> TYPE: DNA
<213> ORGANISM: adeno-associated virus

<400> SEQUENCE: 307
tgtttattct gaaccccgcc ctattggcac tcgttacctt acccggaact tgtaa        55

<210> SEQ ID NO 308
<211> LENGTH: 55
<212> TYPE: DNA
<213> ORGANISM: adeno-associated virus

<400> SEQUENCE: 308
tgtatatagt gaaccccgcc ccattggcac cagatacctg actcgtaatc tgtaa        55

<210> SEQ ID NO 309
<211> LENGTH: 55
<212> TYPE: DNA
<213> ORGANISM: adeno-associated virus

<400> SEQUENCE: 309
gaagtataca gagccgcggg ttattggctc tcgttatttg actaatcatt tgtaa        55

<210> SEQ ID NO 310
<211> LENGTH: 55
<212> TYPE: DNA
<213> ORGANISM: adeno-associated virus
```

<400> SEQUENCE: 310
caactaccac gaactccggg ctattgggtc ccgtttcctc acccaccact tgtaa    55

<210> SEQ ID NO 311
<211> LENGTH: 55
<212> TYPE: DNA
<213> ORGANISM: adeno-associated virus

<400> SEQUENCE: 311
gaaatacact gagcctaggg ctatcggtac ccgctacctc acccaccacc tgtaa    55

<210> SEQ ID NO 312
<211> LENGTH: 55
<212> TYPE: DNA
<213> ORGANISM: adeno-associated virus

<400> SEQUENCE: 312
agcctacaaa gagcccaggg ccattggatc ccgatacctc accaaccacc tctag    55

<210> SEQ ID NO 313
<211> LENGTH: 55
<212> TYPE: DNA
<213> ORGANISM: adeno-associated virus

<400> SEQUENCE: 313
atcctattcc gaacctcgtc ccatcggtac ccgttacctt accaaacctc tgtaa    55

<210> SEQ ID NO 314
<211> LENGTH: 55
<212> TYPE: DNA
<213> ORGANISM: adeno-associated virus

<400> SEQUENCE: 314
ggaatacaga accaccagac ctatcggaac ccgatacctt acccgacccc tttaa    55

<210> SEQ ID NO 315
<211> LENGTH: 55
<212> TYPE: DNA
<213> ORGANISM: adeno-associated virus

<400> SEQUENCE: 315
cgaatacaga accaccagag ccatcggaac ccgatacctc acccgacccc tttaa    55

<210> SEQ ID NO 316
<211> LENGTH: 55
<212> TYPE: DNA
<213> ORGANISM: adeno-associated virus

<400> SEQUENCE: 316
tggatatgta gaagatagat tgattggaac cagatatcta actcaaaatc tgtaa    55

<210> SEQ ID NO 317
<211> LENGTH: 106
<212> TYPE: DNA
<213> ORGANISM: adeno-associated virus

<400> SEQUENCE: 317
ctcgaacctc tcggtctggt tgaggaaggc gctaagacgg ctcctggaaa gaagagaccg    60
gtagagccgt caccacagcg ttcccccgac tcctccacgg gcatcg                  106

<210> SEQ ID NO 318

```
<211> LENGTH: 105
<212> TYPE: DNA
<213> ORGANISM: adeno-associated virus

<400> SEQUENCE: 318
ctcgaacctc tcggtctggt tgaggaagct gctaagacgg ctcctggaaa gaagagaccg      60
gtagaccgtc acctcagcgt tcccccgact cctccacggg catcg                    105

<210> SEQ ID NO 319
<211> LENGTH: 106
<212> TYPE: DNA
<213> ORGANISM: adeno-associated virus

<400> SEQUENCE: 319
ctcgaacctc tcggtctggt tgaggaaggc gctaagacgg ctcctgcaaa gaagagaccg      60
gtagagccgt cacctcagcg ttcccccgac tcctccacgg gcatcg                   106

<210> SEQ ID NO 320
<211> LENGTH: 106
<212> TYPE: DNA
<213> ORGANISM: adeno-associated virus

<400> SEQUENCE: 320
ctcgaacctc tcggtctggc tgaggaagct gctaagacgg ctcctggaaa gaagagaccg      60
gtagaaccgt cacctcagcg ttcccccgac tcctccacgg gcatcg                   106

<210> SEQ ID NO 321
<211> LENGTH: 106
<212> TYPE: DNA
<213> ORGANISM: adeno-associated virus

<400> SEQUENCE: 321
ctcgaacctc tcggtctggt tgaggaagct gctaagacgg ctcctggaaa gaagagaccg      60
gtagaaccgt cacctcagcg ttcccccgac tcctccacgg gcatcg                   106

<210> SEQ ID NO 322
<211> LENGTH: 107
<212> TYPE: DNA
<213> ORGANISM: adeno-associated virus

<400> SEQUENCE: 322
ctcgaacctc tcggtctggt tgaggaagct gctaagacgg ctcctggaaa gaagagaccg      60
gtagaaccgt cacctcagcg ttcccccgac tcctcccacg ggcatcg                  107

<210> SEQ ID NO 323
<211> LENGTH: 106
<212> TYPE: DNA
<213> ORGANISM: adeno-associated virus

<400> SEQUENCE: 323
ctcgaacctc tcggtccggt tgaggaagct gctaagacgg ctcctggaaa gaagagaccg      60
gtagaaccgc cacctcagcg ttcccccgac tcctccacgg gcatcg                   106

<210> SEQ ID NO 324
<211> LENGTH: 106
<212> TYPE: DNA
<213> ORGANISM: adeno-associated virus

<400> SEQUENCE: 324
ctcgaacctc tcggtctggt tgaggaagct gctaagacgg ctcctggaaa gaagagaccg      60
```

```
gtagaaccgt cacctcagcg ttcccccgac tcctccgcgg gcatcg          106
```

<210> SEQ ID NO 325
<211> LENGTH: 106
<212> TYPE: DNA
<213> ORGANISM: adeno-associated virus

<400> SEQUENCE: 325

```
ctcgaacctc tcggtctggt tgaggaagcg gctaagacgg ctcctggaaa gaagagaccg   60
gtagaaccgt cacctcagcg ttcccccgac tcctccacgg gcatcg                106
```

<210> SEQ ID NO 326
<211> LENGTH: 106
<212> TYPE: DNA
<213> ORGANISM: adeno-associated virus

<400> SEQUENCE: 326

```
ctcgaacctc tcggtctggt tgaggaaggc gctaagacgg ctcctggaaa gaagagaccg   60
gtagagccat cacctcagcg ttcccccgac tcctccacgg gcatcg                106
```

<210> SEQ ID NO 327
<211> LENGTH: 106
<212> TYPE: DNA
<213> ORGANISM: adeno-associated virus

<400> SEQUENCE: 327

```
ctcgaacctc tcggtctggt tgaggaaggc gctaagacgg ctcctggaaa gaagagaccg   60
gtagagccat caccccagcg ttctccagac tcctctacgg gcatcg                106
```

<210> SEQ ID NO 328
<211> LENGTH: 91
<212> TYPE: DNA
<213> ORGANISM: adeno-associated virus

<400> SEQUENCE: 328

```
ctcgaacctc tcggtctggt tgaggaaggc gctaagacgg ctcctggaaa gaagagaccc   60
atagaatccc ccgactcctc cacgggcatc g                                 91
```

<210> SEQ ID NO 329
<211> LENGTH: 106
<212> TYPE: DNA
<213> ORGANISM: adeno-associated virus

<400> SEQUENCE: 329

```
ctcgaacctc tcggtctggt tgaggaaggc gctaagacgg ctcctggaaa gaagagaccg   60
gtagagccat caccccagcg ttctccagac tccactacgg gcatcg                106
```

<210> SEQ ID NO 330
<211> LENGTH: 88
<212> TYPE: DNA
<213> ORGANISM: adeno-associated virus

<400> SEQUENCE: 330

```
ctcgagcctc tgggtctggt tgaggaaggc gctaagacgg ctcctggaaa gaagcggcca   60
gtagaaccgg actccagctc gggcatcg                                     88
```

<210> SEQ ID NO 331
<211> LENGTH: 103
<212> TYPE: DNA

<213> ORGANISM: adeno-associated virus

<400> SEQUENCE: 331
ctcgaacctc tcggtctggt tgaggaaggc gctaagacgg ctcctggaaa gaagagacca    60
gtagagcagt caccccaaga accagactcc tcctcgggca tcg                     103

<210> SEQ ID NO 332
<211> LENGTH: 103
<212> TYPE: DNA
<213> ORGANISM: adeno-associated virus

<400> SEQUENCE: 332
ctcgaacctc tcggtctggt tgaggaaggc gctaagacgg ctcctggaaa gaagagaccg    60
gtagagcagt cgccacaaga gccagactcc tcctcgggca tcg                     103

<210> SEQ ID NO 333
<211> LENGTH: 91
<212> TYPE: DNA
<213> ORGANISM: adeno-associated virus

<400> SEQUENCE: 333
ctcgaacctc tcggtctggt tgaggaagtc gctaagacgg ctcctggaaa gaagagaccc    60
atagaatccc ccgactcctc cacgggcatc g                                  91

<210> SEQ ID NO 334
<211> LENGTH: 91
<212> TYPE: DNA
<213> ORGANISM: adeno-associated virus

<400> SEQUENCE: 334
ctcgaacctc tcggtctggt tgaggaaggc gctaagacgg cttccggaaa gaagagaccc    60
atagaatccc ccgactcctc cacgggcatc g                                  91

<210> SEQ ID NO 335
<211> LENGTH: 91
<212> TYPE: DNA
<213> ORGANISM: adeno-associated virus

<400> SEQUENCE: 335
ctcgaacctc tcggtctggt tgaggaaggc gctaagacgg ctcctggaaa gaagagaccc    60
ataggctctc cagactcctc cacgggcatc g                                  91

<210> SEQ ID NO 336
<211> LENGTH: 91
<212> TYPE: DNA
<213> ORGANISM: adeno-associated virus

<400> SEQUENCE: 336
ctcgaacctc tcggtctggt tgaggaaggc gctaagacgg ctcctggaaa gaagagaccc    60
atagactctc cagactcctc cacgggcatc g                                  91

<210> SEQ ID NO 337
<211> LENGTH: 103
<212> TYPE: DNA
<213> ORGANISM: adeno-associated virus

<400> SEQUENCE: 337
ctcgaacctc tcggtctggt tgaggaaggc gctaagacgg ctcctggaaa gaaacgtccg    60
gtagagcagt cgccacaaga gccagactcc tcctcgggca tcg                     103

-continued

<210> SEQ ID NO 338
<211> LENGTH: 103
<212> TYPE: DNA
<213> ORGANISM: adeno-associated virus

<400> SEQUENCE: 338
ctcgaacctc tcggtctggt tgaggaaggc gctaagacgg ctcctccaaa gaaacgtccg      60
gtagagcagt cgccacaaga gccagactcc ccctcgggca tcg                       103

<210> SEQ ID NO 339
<211> LENGTH: 103
<212> TYPE: DNA
<213> ORGANISM: adeno-associated virus

<400> SEQUENCE: 339
ctcgaacctc tcggtctggt tgaggaaggc gctgagacgg ctcctggaaa gaaacgtccg      60
gtagagcagt cgccacaagg gccagactcc tcctcgggca tcg                       103

<210> SEQ ID NO 340
<211> LENGTH: 103
<212> TYPE: DNA
<213> ORGANISM: adeno-associated virus

<400> SEQUENCE: 340
ctcgaacctt ttggtctggt tgaggaaggt gctaagacgg ctcctggaaa gaaacgtccg      60
gtagagcagt cgccacaaga gccagactcc tcctcgggca ttg                       103

<210> SEQ ID NO 341
<211> LENGTH: 103
<212> TYPE: DNA
<213> ORGANISM: adeno-associated virus

<400> SEQUENCE: 341
cttgaacctc tgggcctggt tgaggaacct gttaagacgg ctccgggaaa aaagaggccg      60
gtagagcact ctcctgtcca gccagactcc tcctcgggaa ccg                       103

<210> SEQ ID NO 342
<211> LENGTH: 103
<212> TYPE: DNA
<213> ORGANISM: adeno-associated virus

<400> SEQUENCE: 342
cttgaacctc tgggcctggt tggggaacct gttaagacgg ctccgggaaa aaagaggccg      60
gtagagcact ctcctgtgga gccagactcc tcctcgggaa ccg                       103

<210> SEQ ID NO 343
<211> LENGTH: 102
<212> TYPE: DNA
<213> ORGANISM: adeno-associated virus

<400> SEQUENCE: 343
cttgaacctc tgggcctggt tggggaacct gtcaagacgg ctccaggaaa aagaggccgg      60
tagagcactc tcctgtggag ccagactcct cctcgggaac cg                        102

<210> SEQ ID NO 344
<211> LENGTH: 103
<212> TYPE: DNA
<213> ORGANISM: adeno-associated virus

<400> SEQUENCE: 344
cttgaacctc tgggcctggt tgaggaacct gttaagacgg ctccgggaaa aaagaggccg    60
gtagagcact ctcctgcgga gccagactcc tcctcgggaa ccg                     103

<210> SEQ ID NO 345
<211> LENGTH: 103
<212> TYPE: DNA
<213> ORGANISM: adeno-associated virus

<400> SEQUENCE: 345
cttgaacctc tgggcctggt tgaggaacct gttaagacgg ctccgggaaa aaagaggccg    60
gtagagcact ctcttgcgga gccagactcc tcctcgggaa ccg                     103

<210> SEQ ID NO 346
<211> LENGTH: 103
<212> TYPE: DNA
<213> ORGANISM: adeno-associated virus

<400> SEQUENCE: 346
cttgaacctc tgggcctggt tgaggagcct gttaagacgg ctccgggaaa aaagaggccg    60
gtagagcact ctcctgtgga gccagactcc tcctcgggaa ccg                     103

<210> SEQ ID NO 347
<211> LENGTH: 103
<212> TYPE: DNA
<213> ORGANISM: adeno-associated virus

<400> SEQUENCE: 347
cttgaacctc tgggcctggt tgaggaacct gttaagacgg ctccgggaaa aaagaggccg    60
gtagagcact ctcctgtgga gccagactcc tcctcgggaa cag                     103

<210> SEQ ID NO 348
<211> LENGTH: 103
<212> TYPE: DNA
<213> ORGANISM: adeno-associated virus

<400> SEQUENCE: 348
cttgaacctc tgggcctggt tgaggagcct gttaaaacgg ctccgggaaa aaagaggccg    60
gtagagcact ctcctgcgga gccagactcc tcctcgggaa ccg                     103

<210> SEQ ID NO 349
<211> LENGTH: 103
<212> TYPE: DNA
<213> ORGANISM: adeno-associated virus

<400> SEQUENCE: 349
ctggaacctc tgggcctggt tgaggagcct gttaagacgg ctccgggaaa aaagaggccg    60
gtagagcact ctcctgcaga gccagattcc tcctccggaa ctg                     103

<210> SEQ ID NO 350
<211> LENGTH: 103
<212> TYPE: DNA
<213> ORGANISM: adeno-associated virus

<400> SEQUENCE: 350
ctggaacctc tgagcctggt tgaggagcct gttaagacgg ctccgggaaa aaagaggccg    60
gtagagcact ctcccgcaga gccagattcc tcctccggaa ctg                     103

```
<210> SEQ ID NO 351
<211> LENGTH: 103
<212> TYPE: DNA
<213> ORGANISM: adeno-associated virus

<400> SEQUENCE: 351
cttgaacctc tgggcctggt tgaggaacct gttaaggcgg ctccgggaga aaagaggccg    60
gtagagcact ctcctgcgga gccagactcc tcctcgggaa ccg                    103

<210> SEQ ID NO 352
<211> LENGTH: 103
<212> TYPE: DNA
<213> ORGANISM: adeno-associated virus

<400> SEQUENCE: 352
cttgaacctc tgggcctggt tgaggaacct gttaagacgg ctccgggaga aaagaggccg    60
gtagagcact ctcctgcgga gccagactcc tcctcgggaa ccg                    103

<210> SEQ ID NO 353
<211> LENGTH: 103
<212> TYPE: DNA
<213> ORGANISM: adeno-associated virus

<400> SEQUENCE: 353
cttgaacctc tgggcttggt tggggagcct gttaaaacgg ctccgggaaa aaagaggccg    60
gtagagcact ctcctgtgga gccagactcc tcctcgggaa ccg                    103

<210> SEQ ID NO 354
<211> LENGTH: 102
<212> TYPE: DNA
<213> ORGANISM: adeno-associated virus

<400> SEQUENCE: 354
cttgaacctc tgggcttggt tgaggagcct gttaaaacgg ctccgggaaa aaagaggccg    60
gtagagcact ctcctgtgga gccagactcc tcctcggaac cg                     102

<210> SEQ ID NO 355
<211> LENGTH: 103
<212> TYPE: DNA
<213> ORGANISM: adeno-associated virus

<400> SEQUENCE: 355
cttgaacctc tgggcctggt tgaggagcct gttaaaacgg ctccgggaaa aaagaggccg    60
gtagagcact ctcctgtgga gccagactcc tcctcgggaa ccg                    103

<210> SEQ ID NO 356
<211> LENGTH: 103
<212> TYPE: DNA
<213> ORGANISM: adeno-associated virus

<400> SEQUENCE: 356
cttgaacctc tgggcctggt tgagggacct gttaagacgg ctccgggaaa aaagaggccg    60
gtagagcact ctcctgcgga gccagactcc tcctcgggaa ccg                    103

<210> SEQ ID NO 357
<211> LENGTH: 103
<212> TYPE: DNA
<213> ORGANISM: adeno-associated virus

<400> SEQUENCE: 357
```

```
cttgaacctc tgggcctggt tgaggaacct gttaaaacgg ctccgggaaa aaagaggccg    60
gtagagcact ctcctgtgga gccagactgg tggtgcccaa ccg                    103
```

<210> SEQ ID NO 358
<211> LENGTH: 103
<212> TYPE: DNA
<213> ORGANISM: adeno-associated virus

<400> SEQUENCE: 358

```
cttgaacctc tgggcctggt tgaggagcct gttaaaacgg ctccgggaaa aaagagaccg    60
gtagagcact ctcctgcgga gccagactcc tcctcgggaa ccg                    103
```

<210> SEQ ID NO 359
<211> LENGTH: 103
<212> TYPE: DNA
<213> ORGANISM: adeno-associated virus

<400> SEQUENCE: 359

```
cttgaacctc tgggcctggt tgaggaacct gttaagacgg ctccgggaaa aaagaggccg    60
gtagagcact ctcctgtgga gccagactcc tcctcgggaa ccg                    103
```

<210> SEQ ID NO 360
<211> LENGTH: 105
<212> TYPE: DNA
<213> ORGANISM: adeno-associated virus

<400> SEQUENCE: 360

```
cttgaacctc tgcggcctgg tttgaggaaa cctgttaaga cggctccggg aaaaaagagg    60
ccggtagagc actctcctgt tagccagact cctcctcggg aaccg                  105
```

<210> SEQ ID NO 361
<211> LENGTH: 103
<212> TYPE: DNA
<213> ORGANISM: adeno-associated virus

<400> SEQUENCE: 361

```
cttgaacctc tgggcctggt tgaggaacct gttaaaacgg ctccgggaaa aaagaggccg    60
gtagagcacc ctcctgtgga gccagactcc tcctcgggaa ccg                    103
```

<210> SEQ ID NO 362
<211> LENGTH: 103
<212> TYPE: DNA
<213> ORGANISM: adeno-associated virus

<400> SEQUENCE: 362

```
cttgagcctc ttggtctggt tgaggaagca gctaaaacgg ctcctggaaa gaaggggct    60 gtagatcagt ctcctcagga accggactca tcatctggtg ttg                    103
```

<210> SEQ ID NO 363
<211> LENGTH: 103
<212> TYPE: DNA
<213> ORGANISM: adeno-associated virus

<400> SEQUENCE: 363

```
cttgagcctc ttggtctggt tgaggaagca gctaaaacgg ctcctggaaa gaagaggcct    60
gtagatcagt ctcctcagga accggactca tcatctggtg ttg                    103
```

<210> SEQ ID NO 364
<211> LENGTH: 103

```
<212> TYPE: DNA
<213> ORGANISM: adeno-associated virus

<400> SEQUENCE: 364
cttgagcctc tgggtctggt tgaggaagcg gctaagacgg ctcctggaaa aaagagacct    60
gtagagcaat ctccagcaga accggactcc tcttcgggca tcg                    103

<210> SEQ ID NO 365
<211> LENGTH: 103
<212> TYPE: DNA
<213> ORGANISM: adeno-associated virus

<400> SEQUENCE: 365
ctcgagcctc ttggtctggt tgaggaagct gttaagacgg ctcctggaaa aaagagacct    60
atagagcagt ctcctgcaga accggactct tcctcgggca tcg                    103

<210> SEQ ID NO 366
<211> LENGTH: 103
<212> TYPE: DNA
<213> ORGANISM: adeno-associated virus

<400> SEQUENCE: 366
cttgaacctc ttggtctggt tgaggaagcg gctaagacgg ctcctggaaa gaagaggcct    60
gtagagcagt ctcctcagga accggactcc tccgcgggta ttg                    103

<210> SEQ ID NO 367
<211> LENGTH: 100
<212> TYPE: DNA
<213> ORGANISM: adeno-associated virus

<400> SEQUENCE: 367
ctcgaacctc tgggcctggt tgaagaaggt gctaagacgg ctcctggaaa gaagagaccg    60
ttagagtcac cacaagagcc cgactcctcc tcaggaatcg                        100

<210> SEQ ID NO 368
<211> LENGTH: 100
<212> TYPE: DNA
<213> ORGANISM: adeno-associated virus

<400> SEQUENCE: 368
ctcgaaccac tgggcctggt tgaagaaggt gctaagacgg ctcctggaaa gaagagaccg    60
ttagagtcac cacaagagcc cgactcctcc tcaggaatcg                        100

<210> SEQ ID NO 369
<211> LENGTH: 100
<212> TYPE: DNA
<213> ORGANISM: adeno-associated virus

<400> SEQUENCE: 369
ctcgaacctc tgggcctggt tgaagaaggt gctaaaacgg ctcctggaaa gaagagaccg    60
ttagagtcac cacaagagcc cgactcctcc tcgggcatcg                        100

<210> SEQ ID NO 370
<211> LENGTH: 111
<212> TYPE: DNA
<213> ORGANISM: adeno-associated virus

<400> SEQUENCE: 370
ctcgagcctc tgggtctggt tgaagagggc gttaaaacgg ctcctggaaa gaaacgccca    60
```
ttagaaaaga ctccaaatcg gccgaccaac ccggactctg ggaaggcccc g                111

<210> SEQ ID NO 371
<211> LENGTH: 102
<212> TYPE: DNA
<213> ORGANISM: adeno-associated virus

<400> SEQUENCE: 371
cttgaacctc ttggtctggt tgagcaagcg ggtgagacgg ctcctggaaa gaagagaccg       60
ttgattgatc cccccagcag cccgactcct ccacgggtat cg                         102

<210> SEQ ID NO 372
<211> LENGTH: 106
<212> TYPE: DNA
<213> ORGANISM: adeno-associated virus

<400> SEQUENCE: 372
ctcgaacctc ttggcctggt tgagacgccg gataaaacgg cgcctgcggc aaaaaagagg       60
cctctagagc agagtcctca agagccagac tcctcgagcg gagttg                     106

<210> SEQ ID NO 373
<211> LENGTH: 103
<212> TYPE: DNA
<213> ORGANISM: adeno-associated virus

<400> SEQUENCE: 373
ctcgaaccct ttggtctggt ggaagactca agacggctc cgaccggaga caagcggaaa       60
ggcgaagacg aacctcgttt gcccgacact tcttcacaga ctc                        103

<210> SEQ ID NO 374
<211> LENGTH: 97
<212> TYPE: DNA
<213> ORGANISM: adeno-associated virus

<400> SEQUENCE: 374
ctcgaacctt ttggcctggt tgaagagggt gctaagacgg cccctaccgg aaagcggata      60
gacgaccact ttccaaaaag aaagaaggct cggaccg                               97

<210> SEQ ID NO 375
<211> LENGTH: 88
<212> TYPE: DNA
<213> ORGANISM: adeno-associated virus

<400> SEQUENCE: 375
ttagagccat ttggcctagt agaagatcct gtcaacacgg cacctgcaaa aaaaaataca      60
gggaagctta ctgaccatta cccggtag                                         88

<210> SEQ ID NO 376
<211> LENGTH: 57
<212> TYPE: DNA
<213> ORGANISM: adeno-associated virus

<400> SEQUENCE: 376
cagcgtagat cgtgtgggag ctgcagaagg agaacagcaa gcgcaggaac ccagaat         57

<210> SEQ ID NO 377
<211> LENGTH: 60
<212> TYPE: DNA
<213> ORGANISM: adeno-associated virus

<400> SEQUENCE: 377
cagcgtggag atcgagtggg agctgcagaa ggagaacagc aagcgctgga acccagagat    60

<210> SEQ ID NO 378
<211> LENGTH: 60
<212> TYPE: DNA
<213> ORGANISM: adeno-associated virus

<400> SEQUENCE: 378
cagcgtggag atcgagtggg agctgcagaa ggagaacagc aagcgctgga gcccagagat    60

<210> SEQ ID NO 379
<211> LENGTH: 60
<212> TYPE: DNA
<213> ORGANISM: adeno-associated virus

<400> SEQUENCE: 379
cagcgtggag atcgagtggg agctgcagaa ggagaacagc aagtgctgga acccagagat    60

<210> SEQ ID NO 380
<211> LENGTH: 60
<212> TYPE: DNA
<213> ORGANISM: adeno-associated virus

<400> SEQUENCE: 380
cagcgtggaa atcgagtggg agctgcagaa ggaaaacagc aagcgctggg acccggagat    60

<210> SEQ ID NO 381
<211> LENGTH: 60
<212> TYPE: DNA
<213> ORGANISM: adeno-associated virus

<400> SEQUENCE: 381
cagcgtggaa atcgagtggg agctgcagaa ggagaacagc aaacgctgga acccagagat    60

<210> SEQ ID NO 382
<211> LENGTH: 61
<212> TYPE: DNA
<213> ORGANISM: adeno-associated virus

<400> SEQUENCE: 382
ccagcgtgga aatcgagtgg gagctgcaga aggagaacag caaacgttgg aacccagaga    60
t                                                                   61

<210> SEQ ID NO 383
<211> LENGTH: 60
<212> TYPE: DNA
<213> ORGANISM: adeno-associated virus

<400> SEQUENCE: 383
cagcgtggag atcgagtggg agctgcagaa ggagaacagc aagcgatgga acccagaaat    60

<210> SEQ ID NO 384
<211> LENGTH: 60
<212> TYPE: DNA
<213> ORGANISM: adeno-associated virus

<400> SEQUENCE: 384
cagcgtggaa atcgaatggg agctgcagaa agaaaacagc aagcgctgga acccagagat    60

<210> SEQ ID NO 385
<211> LENGTH: 60
<212> TYPE: DNA

```
<213> ORGANISM: adeno-associated virus

<400> SEQUENCE: 385
cagcgtggaa attgaatggg agctgcagaa agagaacagc aagcgctgga acccagagat      60

<210> SEQ ID NO 386
<211> LENGTH: 60
<212> TYPE: DNA
<213> ORGANISM: adeno-associated virus

<400> SEQUENCE: 386
cagcgtggaa attgaatggg agctgcagaa agaaaacagc aaacgctgga acccagagat      60

<210> SEQ ID NO 387
<211> LENGTH: 60
<212> TYPE: DNA
<213> ORGANISM: adeno-associated virus

<400> SEQUENCE: 387
cagcgtggag attgagtggg agctgcagaa ggagaacagc aagcgctgga atcccgagat      60

<210> SEQ ID NO 388
<211> LENGTH: 60
<212> TYPE: DNA
<213> ORGANISM: adeno-associated virus

<400> SEQUENCE: 388
cagcgtggaa attgaatggg agctgcagaa ggaaaacagc aagcgctgga accccgagat      60

<210> SEQ ID NO 389
<211> LENGTH: 60
<212> TYPE: DNA
<213> ORGANISM: adeno-associated virus

<400> SEQUENCE: 389
cagcgtggaa attgaatggg agctacagaa ggaaaacagc aagcgctgga accccgagat      60

<210> SEQ ID NO 390
<211> LENGTH: 60
<212> TYPE: DNA
<213> ORGANISM: adeno-associated virus

<400> SEQUENCE: 390
cagcgtggaa atcgagtggg agctgcagaa agaaaacagc aagcgctgga atccagagat      60

<210> SEQ ID NO 391
<211> LENGTH: 60
<212> TYPE: DNA
<213> ORGANISM: adeno-associated virus

<400> SEQUENCE: 391
cagcgtggaa atcgagtggg agctgcagaa agaaaacagc aaacgctgga atccagagat      60

<210> SEQ ID NO 392
<211> LENGTH: 60
<212> TYPE: DNA
<213> ORGANISM: adeno-associated virus

<400> SEQUENCE: 392
cagcgtggag atcgagtggg aactgcagaa agaaaacagc aaacactgga atccagagat      60

<210> SEQ ID NO 393
<211> LENGTH: 60
```

<212> TYPE: DNA
<213> ORGANISM: adeno-associated virus

<400> SEQUENCE: 393
cagcgtggag atcgagtggg aactgcagaa agagaacagc aaacgctgga atccagagat    60

<210> SEQ ID NO 394
<211> LENGTH: 60
<212> TYPE: DNA
<213> ORGANISM: adeno-associated virus

<400> SEQUENCE: 394
cagcgtggag atcgagtggg aactgcagaa agaaaacagc aaacgctgga atccagagat    60

<210> SEQ ID NO 395
<211> LENGTH: 60
<212> TYPE: DNA
<213> ORGANISM: adeno-associated virus

<400> SEQUENCE: 395
cagcgtggaa atcgagtggg agctgcagaa agaaaacagc aagcgctgga acccagaaat    60

<210> SEQ ID NO 396
<211> LENGTH: 60
<212> TYPE: DNA
<213> ORGANISM: adeno-associated virus

<400> SEQUENCE: 396
gagtgtggaa attgaatggg agctgcagaa agaaaacagc aagcgctgga atcccgaagt    60

<210> SEQ ID NO 397
<211> LENGTH: 60
<212> TYPE: DNA
<213> ORGANISM: adeno-associated virus

<400> SEQUENCE: 397
gagcgtggag attgaatggg agctgcagaa agaaaacagc aaacgctgga atcccgaagt    60

<210> SEQ ID NO 398
<211> LENGTH: 60
<212> TYPE: DNA
<213> ORGANISM: adeno-associated virus

<400> SEQUENCE: 398
cagcgtggag atcgagtggg agctgcagaa ggaaaacagc aaacgctgga atcccgaaat    60

<210> SEQ ID NO 399
<211> LENGTH: 60
<212> TYPE: DNA
<213> ORGANISM: adeno-associated virus

<400> SEQUENCE: 399
cagcgtggag atcgagtggg agctgcagaa ggagaacagc aaacgctgga atcccgaaat    60

<210> SEQ ID NO 400
<211> LENGTH: 60
<212> TYPE: DNA
<213> ORGANISM: adeno-associated virus

<400> SEQUENCE: 400
cagcgtggag atcgagtggg agctgcagaa ggagaacagc aaacgctgga atcccgagat    60

<210> SEQ ID NO 401

<211> LENGTH: 60
<212> TYPE: DNA
<213> ORGANISM: adeno-associated virus

<400> SEQUENCE: 401
cagcgtggag atcgagtggg agctacagaa ggagaacagc aaacgctgga atcccgagat       60

<210> SEQ ID NO 402
<211> LENGTH: 60
<212> TYPE: DNA
<213> ORGANISM: adeno-associated virus

<400> SEQUENCE: 402
cagcgtggag atcgagtggg agctgcagaa ggagaacagc aaacgctgga accccgagat       60

<210> SEQ ID NO 403
<211> LENGTH: 60
<212> TYPE: DNA
<213> ORGANISM: adeno-associated virus

<400> SEQUENCE: 403
cagcgtggag atcgagtggg agctgcagaa ggaggacagc aaacgctgga accccgagat       60

<210> SEQ ID NO 404
<211> LENGTH: 59
<212> TYPE: DNA
<213> ORGANISM: adeno-associated virus

<400> SEQUENCE: 404
cagcgtagag atcgagtggg agctgcagaa ggagaacagc aaacgctgga acccgagat        59

<210> SEQ ID NO 405
<211> LENGTH: 60
<212> TYPE: DNA
<213> ORGANISM: adeno-associated virus

<400> SEQUENCE: 405
cagcgtggag atcgagtggg agctgcagaa agagaacagc aaacgctgga atcccgaaat       60

<210> SEQ ID NO 406
<211> LENGTH: 60
<212> TYPE: DNA
<213> ORGANISM: adeno-associated virus

<400> SEQUENCE: 406
cagcgtggag attgagtggg agctgcagaa ggagaacagc aaacgctgga accccgagat       60

<210> SEQ ID NO 407
<211> LENGTH: 60
<212> TYPE: DNA
<213> ORGANISM: adeno-associated virus

<400> SEQUENCE: 407
cagcgtggag attgagtggg agctgcggaa ggagaacagc aaacgctgga accccgagat       60

<210> SEQ ID NO 408
<211> LENGTH: 60
<212> TYPE: DNA
<213> ORGANISM: adeno-associated virus

<400> SEQUENCE: 408
cagcgtggaa attgagtggg agctacagaa agaaaacagc aaacgttgga atccagagat       60

```
<210> SEQ ID NO 409
<211> LENGTH: 60
<212> TYPE: DNA
<213> ORGANISM: adeno-associated virus

<400> SEQUENCE: 409
cagcgtggaa atagagtggg agctgcagaa agaaaacagc aaacgctgga acccagaaat      60

<210> SEQ ID NO 410
<211> LENGTH: 60
<212> TYPE: DNA
<213> ORGANISM: adeno-associated virus

<400> SEQUENCE: 410
cagcgtggag atcgagtggg agctgcagaa ggaaaacagc aagcgctgga acccggagat      60

<210> SEQ ID NO 411
<211> LENGTH: 59
<212> TYPE: DNA
<213> ORGANISM: adeno-associated virus

<400> SEQUENCE: 411
cagcgtggag atcgagtggg agctgcagaa ggaaaacagc aagcgtggaa cccggagat       59

<210> SEQ ID NO 412
<211> LENGTH: 60
<212> TYPE: DNA
<213> ORGANISM: adeno-associated virus

<400> SEQUENCE: 412
cagcgtggag attgagtggg agctgcagaa ggaaaacagc aagcgctgga acccggagat      60

<210> SEQ ID NO 413
<211> LENGTH: 60
<212> TYPE: DNA
<213> ORGANISM: adeno-associated virus

<400> SEQUENCE: 413
cgctgttcag attgaatggg aaatcgaaaa ggaacgctcc aaacgctgga atcctgaagt      60

<210> SEQ ID NO 414
<211> LENGTH: 60
<212> TYPE: DNA
<213> ORGANISM: adeno-associated virus

<400> SEQUENCE: 414
cgctgttcag attgaatggg aaatcgaaaa ggaacgctcc aaacgccgga atcctgaagt      60

<210> SEQ ID NO 415
<211> LENGTH: 60
<212> TYPE: DNA
<213> ORGANISM: adeno-associated virus

<400> SEQUENCE: 415
tgccgttcag atcgactggg aaattcagaa ggagcattcc aaacgctgga atcccgaagt      60

<210> SEQ ID NO 416
<211> LENGTH: 60
<212> TYPE: DNA
<213> ORGANISM: adeno-associated virus

<400> SEQUENCE: 416
gtcggtgcag attgactggg agatccagaa ggagcggtcc aaacgctgga accccgaggt      60
```

<210> SEQ ID NO 417
<211> LENGTH: 60
<212> TYPE: DNA
<213> ORGANISM: adeno-associated virus

<400> SEQUENCE: 417
ggctgtcaaa atagaatggg aaatccagaa ggagcggtcc aagagatgga acccagaggt    60

<210> SEQ ID NO 418
<211> LENGTH: 60
<212> TYPE: DNA
<213> ORGANISM: adeno-associated virus

<400> SEQUENCE: 418
caccgtcgaa atcttttggg aactcaagaa ggaaacctcc aagcgctgga accccgaaat    60

<210> SEQ ID NO 419
<211> LENGTH: 60
<212> TYPE: DNA
<213> ORGANISM: adeno-associated virus

<400> SEQUENCE: 419
caccgtggag atggagtggg agctcaagaa ggaaaactcc aagaggtgga acccagagat    60

<210> SEQ ID NO 420
<211> LENGTH: 60
<212> TYPE: DNA
<213> ORGANISM: adeno-associated virus

<400> SEQUENCE: 420
caccgtggag atggaatggg agctcaaaaa ggaaaactcc aagaggtgga acccagagat    60

<210> SEQ ID NO 421
<211> LENGTH: 60
<212> TYPE: DNA
<213> ORGANISM: adeno-associated virus

<400> SEQUENCE: 421
tacagtagag atggtgtggg agctgagaaa agagaattca aagagatgga acccagaaat    60

<210> SEQ ID NO 422
<211> LENGTH: 59
<212> TYPE: DNA
<213> ORGANISM: adeno-associated virus

<400> SEQUENCE: 422
ggagccttac ctggcatggt ctggcagaac cgggacgtgt acctgcaggg tcctatttg     59

<210> SEQ ID NO 423
<211> LENGTH: 59
<212> TYPE: DNA
<213> ORGANISM: adeno-associated virus

<400> SEQUENCE: 423
ggagccttac ctggcatggt ctggcagaac cgggacgtgt acctgcaggg tcccatctg     59

<210> SEQ ID NO 424
<211> LENGTH: 59
<212> TYPE: DNA
<213> ORGANISM: adeno-associated virus

<400> SEQUENCE: 424
ggagccttac ctggtatggt ctggcagaac cgggacgtgt acctgcaggg tcccatctg     59

<210> SEQ ID NO 425
<211> LENGTH: 59
<212> TYPE: DNA
<213> ORGANISM: adeno-associated virus

<400> SEQUENCE: 425
ggagccttac ctggcatggt ctggcagaac cgagacgtgt acctgcaggg tcccatctg      59

<210> SEQ ID NO 426
<211> LENGTH: 59
<212> TYPE: DNA
<213> ORGANISM: adeno-associated virus

<400> SEQUENCE: 426
ggggccttac ctggtatggt ctggcaaaac cgggacgtgt acctgcaggg ccccatctg      59

<210> SEQ ID NO 427
<211> LENGTH: 59
<212> TYPE: DNA
<213> ORGANISM: adeno-associated virus

<400> SEQUENCE: 427
ggagccttac ctggcatggt ctggcagaac cgggacgtgt acctgcaggg tcctatctg      59

<210> SEQ ID NO 428
<211> LENGTH: 59
<212> TYPE: DNA
<213> ORGANISM: adeno-associated virus

<400> SEQUENCE: 428
ggggccttac ccgtatggt ctggcagaac cgggacgtgt acctgcaggg tcccatctg       59

<210> SEQ ID NO 429
<211> LENGTH: 59
<212> TYPE: DNA
<213> ORGANISM: adeno-associated virus

<400> SEQUENCE: 429
ggagttattc ctggtatggt ctggcagaac cgggacgtgt acctgcaggg ccctatttg      59

<210> SEQ ID NO 430
<211> LENGTH: 59
<212> TYPE: DNA
<213> ORGANISM: adeno-associated virus

<400> SEQUENCE: 430
ggggtgattc ccggcatggt gtggcagaat agagacgtgt acctgcaggg tcccatctg      59

<210> SEQ ID NO 431
<211> LENGTH: 59
<212> TYPE: DNA
<213> ORGANISM: adeno-associated virus

<400> SEQUENCE: 431
ggggctctgc ccggcatggt ctggcagaac cgggacgtgt acctgcaggg tcccatctg      59

<210> SEQ ID NO 432
<211> LENGTH: 59
<212> TYPE: DNA
<213> ORGANISM: adeno-associated virus

<400> SEQUENCE: 432
ggggctctgc ccggcatggt ctggcagaac cgggacgtgt gcctgcaggg tcccatctg      59

<210> SEQ ID NO 433
<211> LENGTH: 59
<212> TYPE: DNA
<213> ORGANISM: adeno-associated virus

<400> SEQUENCE: 433
ggagcactgc ctggcatggt ctggcagaac cgggacgtgt atctgcaggg tcccatctg      59

<210> SEQ ID NO 434
<211> LENGTH: 59
<212> TYPE: DNA
<213> ORGANISM: adeno-associated virus

<400> SEQUENCE: 434
ggagcattac ctggcatggt gtggcaagat agagacgtgt acctgcaggg tcccatttg      59

<210> SEQ ID NO 435
<211> LENGTH: 59
<212> TYPE: DNA
<213> ORGANISM: adeno-associated virus

<400> SEQUENCE: 435
ggagcattac ctggcatggt gtggcaaggt agagacgtgt acctgcaggg tcccatttg      59

<210> SEQ ID NO 436
<211> LENGTH: 59
<212> TYPE: DNA
<213> ORGANISM: adeno-associated virus

<400> SEQUENCE: 436
ggagccttac ctggaatggt gtggcaagac agagacgtat acctgcaggg tcctatttg      59

<210> SEQ ID NO 437
<211> LENGTH: 59
<212> TYPE: DNA
<213> ORGANISM: adeno-associated virus

<400> SEQUENCE: 437
ggcgttcttc caggcatggt ctggcaggac agagatgtgt accttcaggg gcccatctg      59

<210> SEQ ID NO 438
<211> LENGTH: 59
<212> TYPE: DNA
<213> ORGANISM: adeno-associated virus

<400> SEQUENCE: 438
ggcgttcttc caggcatggt ctggcaggac agagacgtgt acctgcaggg gcccatctg      59

<210> SEQ ID NO 439
<211> LENGTH: 58
<212> TYPE: DNA
<213> ORGANISM: adeno-associated virus

<400> SEQUENCE: 439
ggcgttcttc caggcatggt gtggcaggac agagacgtgt acctgcaggg gccatctg       58

<210> SEQ ID NO 440
<211> LENGTH: 59
<212> TYPE: DNA
<213> ORGANISM: adeno-associated virus

<400> SEQUENCE: 440

-continued ggcgttcttc caggcatggt ctggcaggac agagacgtgt acctgcaggg gcctatctg    59

<210> SEQ ID NO 441
<211> LENGTH: 59
<212> TYPE: DNA
<213> ORGANISM: adeno-associated virus

<400> SEQUENCE: 441
ggcgttcttc caggcatggt ctggcaggac agagacgtgc acctgcaggg gcctatctg    59

<210> SEQ ID NO 442
<211> LENGTH: 59
<212> TYPE: DNA
<213> ORGANISM: adeno-associated virus

<400> SEQUENCE: 442
ggcgttcttc caggcatggt ctggcaagac agagacgtgt acctgcaggg gcctatttg    59

<210> SEQ ID NO 443
<211> LENGTH: 59
<212> TYPE: DNA
<213> ORGANISM: adeno-associated virus

<400> SEQUENCE: 443
ggcgttcttc caggcatggt cgggcaagac agagacgtgt acctgcaggg gcctacttg    59

<210> SEQ ID NO 444
<211> LENGTH: 58
<212> TYPE: DNA
<213> ORGANISM: adeno-associated virus

<400> SEQUENCE: 444
ggcgttcttc caggcatggt ctggcaggac agagacgtgt acctgcgggg cccatctg    58

<210> SEQ ID NO 445
<211> LENGTH: 59
<212> TYPE: DNA
<213> ORGANISM: adeno-associated virus

<400> SEQUENCE: 445
ggagcgttac ctggtatggt gtggcaggat cgagacgtgt acctgcaggg acccatttg    59

<210> SEQ ID NO 446
<211> LENGTH: 59
<212> TYPE: DNA
<213> ORGANISM: adeno-associated virus

<400> SEQUENCE: 446
ggagcgttac ctggcatggt gtggcaggat cgagacgtgt acctgcaggg acccatttg    59

<210> SEQ ID NO 447
<211> LENGTH: 59
<212> TYPE: DNA
<213> ORGANISM: adeno-associated virus

<400> SEQUENCE: 447
ggagcgttac ctggtatggt gtggcaggat cgagatgtgt accttcaggg acccatttg    59

<210> SEQ ID NO 448
<211> LENGTH: 59
<212> TYPE: DNA
<213> ORGANISM: adeno-associated virus -continued

<400> SEQUENCE: 448
ggagcattac ctggtatggt gtggcaggat cgagacgtgt acctgcaggg acccatttg      59

<210> SEQ ID NO 449
<211> LENGTH: 59
<212> TYPE: DNA
<213> ORGANISM: adeno-associated virus

<400> SEQUENCE: 449
ggagcattac ctggtatggt gtggcaggat cgagacgtgt acctgcgggg acccatttg      59

<210> SEQ ID NO 450
<211> LENGTH: 59
<212> TYPE: DNA
<213> ORGANISM: adeno-associated virus

<400> SEQUENCE: 450
ggggccttac ctggcatggt gtggcaagat cgtgacgtgt accttcaagg acctatctg      59

<210> SEQ ID NO 451
<211> LENGTH: 58
<212> TYPE: DNA
<213> ORGANISM: adeno-associated virus

<400> SEQUENCE: 451
ggagcgttac ctggtatggt gtggcaggat cgagacgtgt actgcaggga cccatttg       58

<210> SEQ ID NO 452
<211> LENGTH: 59
<212> TYPE: DNA
<213> ORGANISM: adeno-associated virus

<400> SEQUENCE: 452
ggaatcttac ctggaatggt gtggcaggac cgcgatgtct atcttcaagg tcccatttg      59

<210> SEQ ID NO 453
<211> LENGTH: 59
<212> TYPE: DNA
<213> ORGANISM: adeno-associated virus

<400> SEQUENCE: 453
ggaatacttc cgggtatggt ttggcaggac agagatgtgt acctgcaagg acccatttg      59

<210> SEQ ID NO 454
<211> LENGTH: 59
<212> TYPE: DNA
<213> ORGANISM: adeno-associated virus

<400> SEQUENCE: 454
ggagtgcttc ctggcatggt gtggcaaaac agagacattt actaccaagg gccaatttg      59

<210> SEQ ID NO 455
<211> LENGTH: 59
<212> TYPE: DNA
<213> ORGANISM: adeno-associated virus

<400> SEQUENCE: 455
ggagtgctgc ctggcatggt gtggcaaaac agagacattt actaccaagg gccaatttg      59

<210> SEQ ID NO 456
<211> LENGTH: 59
<212> TYPE: DNA
<213> ORGANISM: adeno-associated virus

<400> SEQUENCE: 456
ggaattgttc ccggaatggt ctggcaaaac agagacatct actaccaggg ccctatttg      59

<210> SEQ ID NO 457
<211> LENGTH: 59
<212> TYPE: DNA
<213> ORGANISM: adeno-associated virus

<400> SEQUENCE: 457
ggagccgtgc ctggaatggt gtggcaaaac agagacattt actaccaggg tcccatttg      59

<210> SEQ ID NO 458
<211> LENGTH: 59
<212> TYPE: DNA
<213> ORGANISM: adeno-associated virus

<400> SEQUENCE: 458
ggcgtgtacc cggaatggt gtggcaggac agagacattt actaccaagg gcccatttg       59

<210> SEQ ID NO 459
<211> LENGTH: 60
<212> TYPE: DNA
<213> ORGANISM: adeno-associated virus

<400> SEQUENCE: 459
ggggcgcttc ccgggatggt gtggcaaaac agagacattt accctacagg gacccatttg     60

<210> SEQ ID NO 460
<211> LENGTH: 59
<212> TYPE: DNA
<213> ORGANISM: adeno-associated virus

<400> SEQUENCE: 460
gaaatcgtgc ccggcagcgt gtggatggag agggacgtgt acctccaagg acccatctg      59

<210> SEQ ID NO 461
<211> LENGTH: 58
<212> TYPE: DNA
<213> ORGANISM: adeno-associated virus

<400> SEQUENCE: 461
gaagtgcttc ctggcagcgt atggatggag agggacgtgt acctccagga cccatctg       58

<210> SEQ ID NO 462
<211> LENGTH: 59
<212> TYPE: DNA
<213> ORGANISM: adeno-associated virus

<400> SEQUENCE: 462
ggagctttac caggaatggt ttggcagaac agggatatat atctgcaggg acctattgg      59

<210> SEQ ID NO 463
<211> LENGTH: 10
<212> TYPE: DNA
<213> ORGANISM: adeno-associated virus

<400> SEQUENCE: 463
gggagctaca       10